US011925696B2

(12) United States Patent
Low et al.

(10) Patent No.: US 11,925,696 B2
(45) Date of Patent: Mar. 12, 2024

(54) CARBONIC ANHYDRASE IX TARGETING AGENTS AND METHODS

(71) Applicant: Purdue Research Foundation, West Lafayette, IN (US)

(72) Inventors: Philip S. Low, West Lafayette, IN (US); Pengcheng Lu, Hoover, AL (US)

(73) Assignee: Purdue Research Foundation, West Lafayette, IN (US)

(*) Notice: Subject to any disclaimer, the term of this patent is extended or adjusted under 35 U.S.C. 154(b) by 0 days.

(21) Appl. No.: 16/085,393

(22) PCT Filed: Mar. 16, 2017

(86) PCT No.: PCT/US2017/022785
§ 371 (c)(1),
(2) Date: Sep. 14, 2018

(87) PCT Pub. No.: WO2017/161170
PCT Pub. Date: Sep. 21, 2017

(65) Prior Publication Data
US 2019/0083663 A1 Mar. 21, 2019

Related U.S. Application Data

(60) Provisional application No. 62/309,264, filed on Mar. 16, 2016, provisional application No. 62/309,268, filed on Mar. 16, 2016.

(51) Int. Cl.
*A61K 51/04* (2006.01)
*A61K 47/60* (2017.01)
*A61K 47/65* (2017.01)
*A61K 49/00* (2006.01)

(52) U.S. Cl.
CPC .......... *A61K 51/0497* (2013.01); *A61K 47/60* (2017.08); *A61K 47/65* (2017.08); *A61K 49/0032* (2013.01); *A61K 49/0041* (2013.01); *A61K 51/04* (2013.01); *A61K 2123/00* (2013.01)

(58) Field of Classification Search
CPC ................. A61K 51/04; A61K 51/0497; A61K 49/0041; A61K 49/0032; A61K 2123/00; A61K 47/60; A61K 47/65; A61P 35/00
See application file for complete search history.

(56) References Cited

U.S. PATENT DOCUMENTS

| 7,862,798 | B2 | 1/2011 | Leamon et al. |
| 8,541,604 | B2 | 9/2013 | Bernardin et al. |
| 9,193,763 | B2 | 11/2015 | Low et al. |
| 10,221,159 | B2* | 3/2019 | Groves .................. A61P 37/00 |
| 10,857,234 | B2* | 12/2020 | Leamon ............... C07K 5/1021 |
| 2009/0043099 | A1 | 2/2009 | Reed et al. |
| 2009/0175794 | A1* | 7/2009 | Zimmerman ........ C07D 401/12 424/9.1 |
| 2010/0323973 | A1 | 12/2010 | Leamon et al. |
| 2011/0321183 | A1 | 12/2011 | Ploegh et al. |
| 2012/0270791 | A1 | 10/2012 | Leamon et al. |
| 2012/0309045 | A1 | 12/2012 | Knutson, Jr. et al. |
| 2013/0143164 | A1 | 6/2013 | Yabuki et al. |
| 2014/0058064 | A1 | 2/2014 | Vlahov et al. |
| 2014/0073761 | A1 | 3/2014 | Leamon et al. |
| 2014/0234216 | A1 | 8/2014 | Schibli et al. |
| 2015/0353580 | A1 | 12/2015 | Hutchison et al. |
| 2016/0016993 | A1 | 1/2016 | Vlahov et al. |
| 2019/0083631 | A1* | 3/2019 | Leamon ............... A61K 47/545 |

FOREIGN PATENT DOCUMENTS

| EP | 2455158 | 5/2012 |
| WO | 2009089383 A2 | 7/2009 |
| WO | 2011/098610 | 8/2011 |
| WO | 2012154885 | 11/2012 |
| WO | 2015113760 A1 | 8/2015 |
| WO | 2017/161144 | 9/2017 |
| WO | 2017/161170 | 9/2017 |
| WO | 2017/177149 | 10/2017 |

OTHER PUBLICATIONS

Bozdag et al., J. Med. Chem., 2014, 57, p. 9673-9686. (Year: 2014).*
Rami et al., New J. Chem., 2010, 34, p. 2139-2144. (Year: 2010).*
Aime et al., J. Chem. Soc. Dalton Trans., 1995, p. 2259-2266. (Year: 1995).*
"Ligand," https://science.jrank.org/pages/3925/Ligand-Structure-bonding.html, 2022. (Year: 2022).*
American Association of Cancer Research News Published Mar. 2015.
Asakawa et al., "Radiosynthesis to three {$^{11}$C}ureido-substituted benzenesulfonamides as PET probes for carbonic anhydrase IX in tumors," Biorganic & Medicinal Chem. Ltrs., 21:7017-7020 (2011).
Cecchi et al., "Carbonic anhydrase inhibitors. Design of fluorescent sulfonamides as probes of tumor-associated carbonic anhydrase IX that inhibit isozyme IX-mediated acidification of hypoxic tumors," Journal Of Medicinal Chemistry, 48(15): Jul. 6, 2005, pp. 4834-4841.
Extended European Search Report (EESR) issued in EP Appl. No. 17767563.4, (dated Sep. 19, 2019).
Extended European Search Report (EESR) issued in EP Appl. No. 17767541.0, (dated Nov. 5, 2019).
Krall, Nikolas et al., "A Small-Molecule Drug Conjugate for the Treatment of Carbonic Anhydrase IX Expressing Tumors," Angewandte Chemie International Edition, 53(16): Apr. 14, 2014, pp. 4231-4235.

(Continued)

*Primary Examiner* — Michael G. Hartley
*Assistant Examiner* — Leah H Schlientz
(74) *Attorney, Agent, or Firm* — Barnes & Thornburg LLP

(57) ABSTRACT

The present disclosure relates to compositions and methods of carbonic anhydrase IX inhibitors. The present disclosure also relates to targeting conjugates of carbonic anhydrase IX inhibitors. The present disclosure also relates to the use of targeting conjugates of carbonic anhydrase IX inhibitors in SPECT imaging methods.

10 Claims, 22 Drawing Sheets

(56) References Cited

OTHER PUBLICATIONS

Peng-Cheng et al., "Evaluation of a Carbonic Anhydrase IX-Targeted Near-Infrared Dye for Fluorescence-Guided Surgery of Hypoxic Tumors," Molecular Pharmaceutics (Apr. 4, 2016), 13(5): ISSN 1543-8384, pp. 1618-1625.
Peng-Cheng et al., "Evaluation of Nonpeptidic Ligand Conjugates for SPECT Imaging of Hypoxic and Carbonic Anhydrase IX-Expressing Cancers", Bioconjugate Chemistry, (Jun. 30, 2016), 27(7): ISSN 1043-1802, pp. 1762-1769.
Peng-Cheng et al., "Evaluation of Nonpeptidic Ligand Conjugates for the Treatment of Hypoxic and Carbonic Anhydrase IX-Expressing Cancers," Molecular Cancer Therapeutics (Mar. 2, 2017), 16(3): ISSN 1535-7163, pp. 453-460.
Rami et al., "Carbonic anhydrase inhibitors: Copper(II) complexes of polyamino-polycarboxylamido aromatic/heterocyclic sulphonamides are very potent inhibitors of the tumour-associated isoforms IX and XII", Bioorganic & Medicinal Chemistry Letters, 18(2): Jan. 15, 2008, pp. 836-841.
PCT International Search Report and Written Opinion for PCT/USZ017/022785, completed on May 9, 2017, 20 pages.

\* cited by examiner

CARBONIC ANHYDRASE IX TARGETING AGENTS AND METHODS

CROSS REFERENCE TO RELATED APPLICATIONS

This application is a national stage entry under 35 U.S.C. 371(c) of PCT International Patent Application No. PCT/US2017/022785, filed on Mar. 16, 2017, which claims the benefit under 35 U.S.C. § 119(e) of U.S. Provisional Patent Application No. 62/309,264, filed on Mar. 16, 2016, and U.S. Provisional Patent Application No. 62/309,268, filed on Mar. 16, 2016, the entire disclosures of which are incorporated herein by reference.

FIELD

The present disclosure relates to compositions and methods of carbonic anhydrase IX inhibitors. The present disclosure also relates to targeting conjugates of carbonic anhydrase IX inhibitors. The present disclosure also relates to the use of targeting conjugates of carbonic anhydrase IX inhibitors in SPECT imaging methods.

BACKGROUND

The microenvironment can greatly affect the phenotype of cancer cells within a tumor. One such microenvironmental effect is hypoxia due to poorly formed vasculature present within tumors (See for example Noman M Z, Hasmim M, Messai Y, Terry S, Kieda C, Janji B, Chouaib S. Hypoxia: a key player in anti-tumor immune response. A review in the Theme: Cellular Responses to Hypoxia. *Am J Physiol Cell Physiol.* 2015, 309(1):C569-0579). Studies have shown that 1% to 1.5% of all genes are regulated by hypoxia (Harris A L. Hypoxia—a key regulatory factor in tumour growth. *Nat Rev Cancer.* 2002. 2(1):38-47). Not surprisingly then, hypoxic cancer cells can exhibit markedly different patterns of gene expression. These changes can lead to differences in sensitivity towards chemotherapeutics when in a hypoxic microenvironment which in turn can lead to increased aggressiveness and recurrence of the cancer (Yamada S, Utsunomiya T, Morine Y, Imura S, Ikemoto T, Arakawa Y, Kanamoto M, Iwahashi S, Saito Y, Takasu C, Ishikawa D, Shimada M. Expressions of hypoxia-inducible factor-1 and epithelial cell adhesion molecule are linked with aggressive local recurrence of hepatocellular).

Due to the effects of hypoxia, efforts have been made to identify cancer specific hypoxia markers to exploit for selective imaging. One such marker, carbonic anhydrase IX (CA IX) is expressed via the activation of hypoxia-inducible factor-1 (HIF-1). CA IX is a member of a group of metalloproteins, usually containing Zinc that catalyze the reversible hydration of carbon dioxide (($CO_2 + H_2O \leftrightarrow HCO_3^- + H^+$). CAIX is among the most active CAs for the $CO_2$ hydration reaction, and contains four domains on the basis of sequence similarity: an N-terminal proteoglycan-like (PG) domain, a CA catalytic domain, a transmembrane segment (TM), and an intracytoplasmic (IC) portion. CA IX is expressed in many cancers including lung, colorectal, gastric, pancreatic, breast, cervical, bladder, ovarian, brain, head & neck and oral cavity cancers. Additionally, due to a mutation in the VHL gene that leads to constitutive HIF-1 activation, cancers such as clear cell carcinoma of the kidney have been shown to upregulate CA IX up to 150-fold over basal levels. In normal cells, however, CA IX is only expressed in epithelial cells of the stomach and gallbladder where it appears to be catalytically inactive.

As CA IX has been touted as an excellent target for the specific delivery of imaging agents, both small molecule- and antibody-conjugates have been created to image hypoxic tumors. For example, CA IX-specific ligands have been used to image moue xenograft models of colon, renal and cervical cancers. CA IX-specific antibodies have been used to image mouse xenograft models of clear cell renal, head & neck, colon and cervical cancers in addition to human patients with clear cell renal carcinomas.

Furthermore, while much effort has been made towards CA IX-targeted imaging agents, conversely, very little research has been conducted towards targeting therapeutics to CA IX expressing cancers. The few reports of CA IX-targeted therapies involve the use of anti-CA IX antibodies either directly labeled with a therapeutic radionuclide (Muselaers C H, Oosterwijk E, Bos D L, Oyen W J, Mulders P F, Boerman O C. Optimizaing lutetium 177-anti-carbonic anhydrase IX radioimmunotherapy in an intraperitoneal clear cell renal cell carcinoma xenograft model. *Mol Imaging.* 2014. 13:1-7) or conjugated to drug containing liposomes (Wong B C, Zhang H, Qin L, Chen H, Fang C, Lu A, Yang Z. Carbonic anhydrase IX-directed immunoliposomes for targeted drug delivery to human lung cancer cells in vitro. *Drug Des Devel Ther.* 2014, 8:993-1001). To our knowledge, the efficacy of a small molecule CA IX ligand directly conjugated to a highly potent anti-cancer drug has not been reported in an in vivo mouse xenograft model.

While small molecule conjugates have primarily used PET and fluorescence to image hypoxic tumors, there is a need for the development of further selective imaging agents. Furthermore, there is an unmet need for the development of CA IX targeted therapeutics.

SUMMARY

In some embodiments, the disclosure provides a conjugate comprising a CA IX ligand covalently bound through a linker to at least one agent selected from the group consisting of a therapeutic agent and an imaging agent; or a pharmaceutically acceptable salt thereof. In some embodiments, the disclosure provides a conjugate comprising a CA IX ligand covalently bound to at least one agent selected from the group consisting of a therapeutic agent and an imaging agent; or a pharmaceutically acceptable salt thereof. In some embodiments, the disclosure provides a conjugate of the formula B-L-A, wherein B is a binding ligand of carbonic anhydrase IX, L is an optional linker, and A is a therapeutic agent and an imaging agent. In some aspects of these embodiments, the CA IX ligand is an aryl sulfonamide containing compound. In some aspects of these embodiments, the CA IX ligand is of the formula

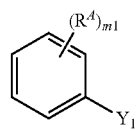

wherein
each $R^A$ is independently selected from the group consisting of H, halogen, $-OR^{1'}$, $-OC(O)R^{1'}$, $-OC(O)NR^{1'}R^{2'}$, $-OS(O)R^{1'}$, $-OS(O)_2R^{1'}$, $-SR^{1'}$, $-S(O)R^{1'}$, $-S(O)_2R^{1'}$, $-S(O)NR^{1'}R^{2'}$, $-S(O)_2NR^{1'}R^{2'}$, $-OS(O)NR^{1'}R^{2'}$, $-OS(O)_2NR^{1'}R^{2'}$, $-NR^{1'}R^{2'}$, $-NR^{1'}C(O)R^{1'}$, —NR$^1$C(O)OR$^{2'}$, —NR$^1$C(O)NR$^1$R$^{2'}$, —NR$^1$S(O)R$^{2'}$, —NR$^1$S(O)$_2$R$^{2'}$, —NR$^1$S(O)N R$^1$R$^{2'}$, —NR$^1$S(O)$_2$NR$^1$R$^{2'}$, —C(O)R$^{1'}$, —C(O)OR$^{1'}$, and —C(O)NR$^1$R$^{2'}$;

Y$_1$ is —OR$^B$, —SR$^B$, —NR$^B$R$^B$, —S(O)$_2$R$^B$, —NR$^B$C(O)R$^{B'}$ or —NR$^B$C(O)NR$^B$R$^{B'}$;

each R$^B$ and R$^{B'}$ is independently H, C$_1$-C$_{10}$ alkyl, C$_2$-C$_{10}$ alkenyl or phenyl; wherein each hydrogen atom in C$_1$-C$_{10}$ alkyl, C$_2$-C$_{10}$ alkenyl, and phenyl is optionally substituted with —CN, C$_1$-C$_6$ alkyl-(5- to 9-membered heteroaryl), —NR$^3$R$^4$, —NR$^{3'}$(CH$_2$)$_{m2}$NR$^{3'}$R$^{4'}$ or —C$_6$H$_4$OR$^{3'}$;

each R$^{3'}$ and R$^{4'}$ is independently H, —CH$_2$C(O)*, —CH$_2$C(O)OR$^{5'}$, —CH$_2$C(O)NR$^{5'}$R$^{6'}$, or a bond to the rest of the conjugate;

each R$^{5'}$ and R$^{6'}$ is independently H, C$_1$-C$_8$ alkyl, or phenyl, wherein each hydrogen atom in wherein each hydrogen atom in C$_1$-C$_{10}$ alkyl, C$_2$-C$_{10}$ alkenyl, and phenyl is optionally substituted with C$_1$-C$_6$ alkyl-(phenyl), —OR$^{1'}$, —OC(O)R$^{1'}$, —OC(O)NR$^1$R$^{2'}$, —OS(O)R$^{1'}$, —OS(O)$_2$R$^{1'}$, —SR$^{1'}$, —S(O)R$^{1'}$, —S(O)$_2$R$^{1'}$, —S(O)NR$^1$R$^{2'}$, —S(O)$_2$NR$^F$R$^2$, —OS(O)NR$^1$R$^{2'}$, —OS(O)$_2$NR$^1$R$^{2'}$, —NR$^1$R$^{2'}$, —NR$^1$C(O)R$^{1'}$, —NR$^1$C(O)OR$^{2'}$, —NR$^1$C(O)NR$^1$R$^{2'}$, —NR$^1$S(O)R$^{2'}$, —NR$^1$S(O)$_2$R$^{2'}$, —NR$^1$S(O)N R$^1$R$^{2'}$, —NR$^1$S(O)$_2$NR$^1$R$^{2'}$, —C(O)R$^{1'}$, —C(O)OR$^{1'}$, and —C(O)NR$^1$R$^{2'}$;

each R$^{1'}$ and R$^{2'}$ is independently selected from the group consisting of H, C$_1$-C$_6$ alkyl, C$_2$-C$_6$ alkenyl, C$_2$-C$_6$ alkynyl, and C$_3$-C$_9$ cycloalkyl;

m1 is 1, 2, 3, 4 or 5; and

* represents a covalent bond to the rest of the conjugate.

In some embodiments, at least one R$^A$ is a —S(O)$_2$NR$^1$R$^{2'}$. In some embodiments, m1 is 1, and R$^A$ is a —S(O)$_2$NR$^1$R$^2$.

In some embodiments, the CA IX ligand is selected from the group consisting of

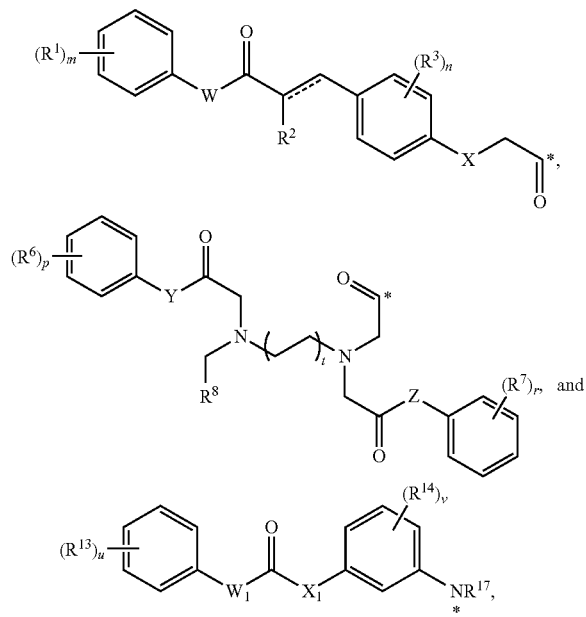

wherein each R$^1$ and R$^3$ is independently selected from the group consisting of H, —OR$^4$, —OC(O)R$^4$, —OC(O)NR$^4$R$^5$, —OS(O)R$^4$, —OS(O)$_2$R$^4$, —SR$^4$, —S(O)R$^4$, —S(O)$_2$R$^4$, —S(O)NR$^4$R$^5$, —S(O)$_2$NR$^4$R$^5$, —OS(O)NR$^4$R$^5$, —OS(O)$_2$NR$^4$R$^5$, —NR$^4$R$^5$, —NR$^4$C(O)R$^5$, —NR$^4$C(O)OR$^5$, —NR$^4$C(O)NR$^4$R$^5$, —NR$^4$S(O)R$^5$, —NR$^4$S(O)$_2$R$^5$, —NR$^4$S(O)NR$^4$R$^5$, —NR$^4$S(O)$_2$NR$^4$R$^5$, —C(O)R$^4$, —C(O)OR$^4$, and —C(O)NR$^4$R$^5$;

R$^2$ is selected from the group consisting of H, —CN, C$_1$-C$_6$ alkyl, C$_2$-C$_6$ alkenyl, and C$_2$-C$_6$ alkynyl;

W is —O—, —CH$_2$— or —NR$^{4'}$—;

X is —O—, —CH$_2$— or —NR$^{5'}$—;

each R$^4$, R$^5$, R$^{4'}$ and R$^{5'}$ is independently selected from the group consisting of H, C$_1$-C$_6$ alkyl, C$_2$-C$_6$ alkenyl, and C$_2$-C$_6$ alkynyl;

m is an integer from 1 to 4; and n is an integer from 0 to 2;

wherein each R$^6$ and R$^7$ is independently selected from the group consisting of H, —OR$^9$, —OC(O)R$^9$, —OC(O)NR$^9$R$^{10}$, —OS(O)R$^9$, —OS(O)$_2$R$^9$, —SR$^9$, —S(O)R$^9$, —S(O)$_2$R$^9$, —S(O)NR$^9$R$^{10}$, —S(O)$_2$NR$^9$R$^{10}$, —OS(O)NR$^9$R$^{10}$, —OS(O)$_2$NR$^9$R$^{10}$, —NR$^9$R$^{10}$, —NR$^9$C(O)R$^{10}$, —NR$^9$C(O)OR$^{10}$, —NR$^9$C(O)NR$^9$R$^{10}$, —NR$^9$S(O)R$^{10}$, —NR$^9$S(O)$_2$R$^{10}$, —NR$^9$S(O)NR$^9$R$^{10}$, —NR$^9$S(O)$_2$NR$^9$R$^{10}$, —C(O)R$^9$, —C(O)OR$^9$, and —C(O)NR$^9$R$^{10}$;

R$^8$ is selected from the group consisting of H, C$_1$-C$_6$ alkyl, C$_2$-C$_6$ alkenyl, and C$_2$-C$_6$ alkynyl, —C(O)R$^{11}$, —C(O)OR$^{11}$, and —C(O)NR$^{11}$R$^{12}$;

Y is —O—, —CH$_2$— or —NR$^{9'}$—;

Z is —O—, —CH$_2$— or —NR$^{10'}$—;

each R$^9$, R10, R$^{9'}$, R$^{10'}$ R$^{11}$ and R$^{12}$ is independently selected from the group consisting of H, C$_1$-C$_6$ alkyl, C$_2$-C$_6$ alkenyl, and C$_2$-C$_6$ alkynyl;

p is an integer from 1 to 4;

r is an integer from 0 to 4; and t is an integer from 1 to 3;

wherein each R$^{13}$ and R$^{14}$ is independently selected from the group consisting of H, —OR$^{15}$, —OC(O)R$^{15}$, —OC(O)NR$^{15}$R$^{16}$, —OS(O)R$^{15}$, —OS(O)$_2$R$^{15}$, —SR$^{15}$, —S(O)R$^{15}$, —S(O)$_2$R$^{15}$, —S(O)NR$^{15}$R$^{16}$, —S(O)$_2$NR$^{15}$R$^{16}$, —OS(O)NR$^{15}$R$^{16}$, —OS(O)$_2$NR$^{15}$R$^{16}$, —NR$^{15}$R$^{16}$, —NR$^{15}$C(O)R$^{16}$, —NR$^{15}$C(O)OR$^{16}$, —NR$^{15}$C(O)NR$^{15}$R$^{16}$, —NR$^{15}$S(O)R$^{16}$, —NR$^{15}$S(O)$_2$R$^{16}$, —NR$^{15}$S(O)NR$^{15}$R$^{16}$, —NR$^{15}$S(O)$_2$NR$^{15}$R$^{16}$, —C(O)R$^{15}$, —C(O)OR$^{15}$, and —C(O)NR$^{15}$R$^{16}$;

W$_1$ is —O—, —CH$_2$— or —NR$^{15'}$—;

X$_1$ is —O—, —CH$_2$— or —NR$^{16'}$—;

each R$^{15}$, R$^{16}$ R$^{15'}$, R$^{16'}$ and R$^{17}$ is independently selected from the group consisting of H, C$_1$-C$_6$ alkyl, C$_2$-C$_6$ alkenyl, and C$_2$-C$_6$ alkynyl;

u is an integer from 1 to 4; and is an integer from 0 to 2; and each * represents a covalent bond to the rest of the conjugate.

In other embodiments, the disclosure provide a method of imaging a population of cells in a subject, comprising a. administering to the subject an effective amount of a conjugate comprising a CA IX ligand covalently bound through a linker to at least one imaging agent; or a pharmaceutically acceptable salt thereof.

In other embodiments, the disclosure provide a method of imaging a population of cells in a subject, comprising a. administering to the subject an effective amount of a conjugate of the formula B-L-A, wherein B is a binding ligand of carbonic anhydrase IX, L is an optional linker, and A is an imaging agent. In some aspects of these embodiments, the CA IX ligand is an aryl sulfonamide containing compound. In some aspects of these embodiments, the CA IX ligand is of the formula

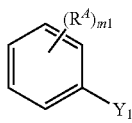

wherein $R^4$, $Y_1$ and m1 are as defined herein.

In some aspects of these embodiments, the CA IX ligand is selected from the group consisting of

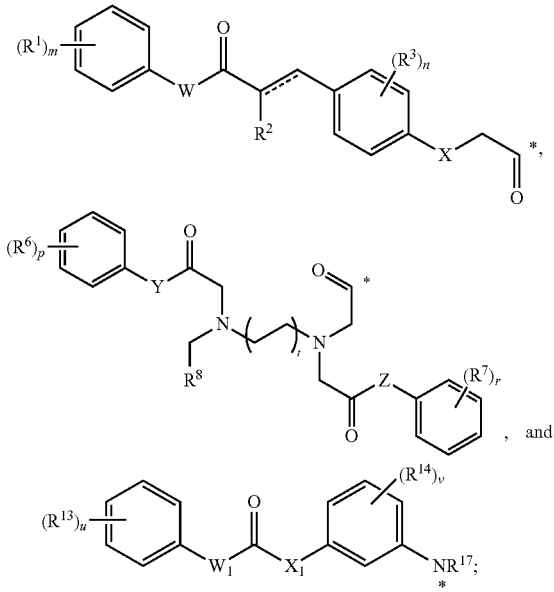

, and wherein $R^1$, $R^2$, $R^3$ $R^4$, $R^5$, $R^{4'}$, $R^{5'}$, $R^{4''}$, $R^{5''}$, $R^6$, $R^7$, $R^8$, $R^9$, $R^{10}$, $R^{9'}$, $R^{10'}$ $R^{9''}$, $R^{10''}$, $R^{11}$, $R^{12}$, $R^{13}$, $R^{14}$, $R^{15}$, $R^{16}$ $R^{15'}$, $R^{16'}$ $R^{15''}$, $R^{16''}$, $R^{17}$, W, $W_1$, X, $X_1$, Y, Z, m, n, p, r, t, u, and v are as described herein, and each * represents a covalent bond to the rest of the conjugate, or a pharmaceutically acceptable salt thereof. In some aspects of these embodiments, the imaging agent is a SPECT imaging agent, or a pharmaceutically acceptable salt thereof. In some aspects of these embodiments, the imaging agent is an imaging agent of the formula

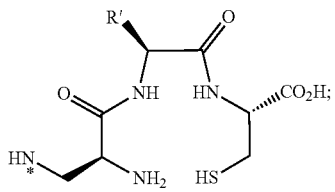

wherein R' is H, or R' is selected from the group consisting of $C_1$-$C_6$ alkyl, amino-$C_1$-$C_6$ alkyl, carboxy-$C_1$-$C_6$ alkyl, hydroxyl-$C_1$-$C_6$ alkyl, $C_1$-$C_6$heteroalkyl, $C_6$-$C_{10}$ aryl, $C_6$-$C_{10}$ aryl-$C_1$-$C_6$ alkyl alkyl and $C_5$-$C_{10}$ heteroaryl-$C_1$-$C_6$ alkyl; and * represents a covalent bond to the rest of the conjugate, and wherein a radionuclei is bound to the conjugate, or a pharmaceutically acceptable salt thereof. In some aspects of these embodiments, the imaging agent is an imaging agent of the formula

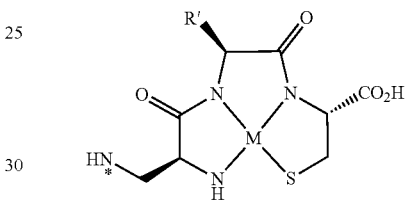

wherein M is a cation of a radionuclide, and * represents a covalent bond to the rest of the conjugate, or a pharmaceutically acceptable salt thereof. In some aspects of these embodiments, the radionuclei is selected from the group consisting of an isotope of gallium, an isotope of indium, an isotope of copper, an isotope of technetium, and an isotope of rhenium. In some aspects of these embodiments, the radionuclei is an isotope of technetium. In some aspects of these embodiments, the radionuclei is $^{99m}$Tc. In some aspects of these embodiments, the conjugate is selected from the group consisting of

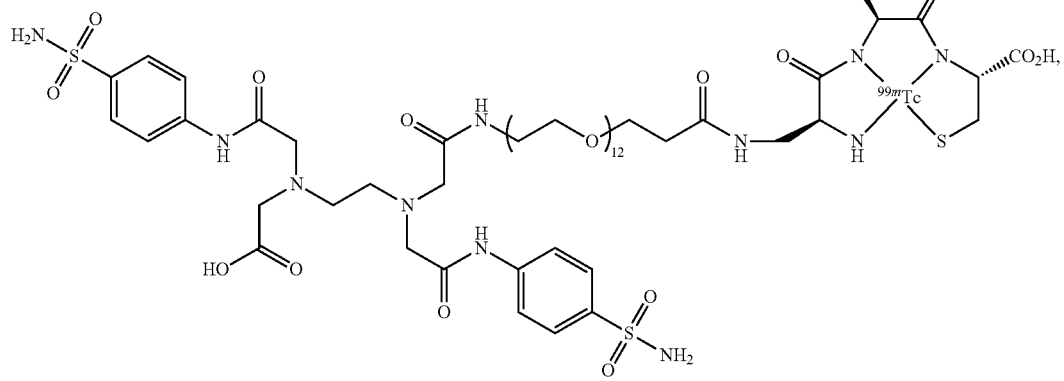

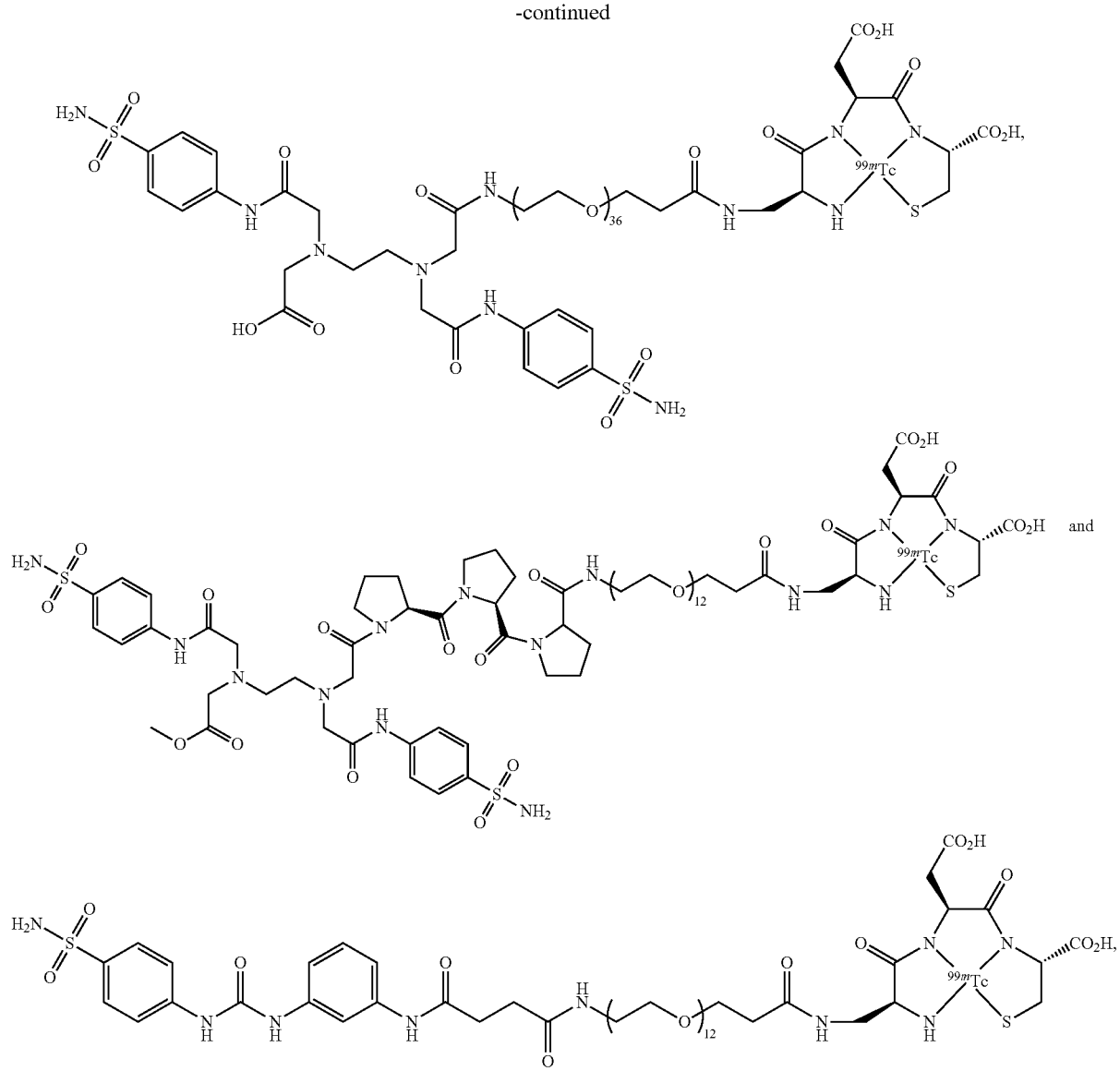

or a pharmaceutically acceptable salt thereof.

In other embodiments, the present disclosure provides a composition comprising a conjugate as described herein, or a pharmaceutically acceptable salt thereof, and optionally at least one pharmaceutically acceptable excipient.

In other embodiments, the present disclosure provides a conjugate as described herein for use in a method of imaging a population of cells in a subject. In some aspects of these embodiments, the method comprises administering to the subject an amount of the conjugate effective for imaging the cells.

In other embodiments, the present disclosure provides a use of a conjugate as described herein in the preparation of a medicament useful for imaging a population of cells in a subject. In some aspects of these embodiments, the method comprises administering to the subject an amount of the conjugate effective for imaging the cells.

In other embodiments, the present disclosure provides a method of treating cancer in a subject, comprising, a. administering to the subject an effective amount of a conjugate described herein; or a pharmaceutically acceptable salt thereof. In other embodiments, the method further comprises, b. identifying a patient for treatment by imaging. In some aspects of these embodiments, the imaging comprises c. administering to the patient an effective amount of a conjugate wherein the agent is an imaging agent as described herein; and d. identifying the patient as having a CA IX expressing cancer. In some aspects of these embodiments, the cancer is selected from the group consisting of lung, colorectal, gastric, pancreatic, breast, cervical, bladder, ovarian, brain, head & neck, oral and kidney cancer.

In other embodiments, the present disclosure provides a conjugate as described herein for use in a method of treating cancer in a subject. In some aspects of these embodiments, the method comprises administering to the subject an amount of the conjugate effective for treating the cancer. In some aspects of these embodiments, the cancer is selected from the group consisting of lung, colorectal, gastric, pancreatic, breast, cervical, bladder, ovarian, brain, head & neck, oral and kidney cancer.

In other embodiments, the present disclosure provides a use of a conjugate as described herein in the preparation of a medicament useful for treating cancer in a subject. In some aspects of these embodiments, the method comprises administering to the subject an amount of the conjugate effective for treating the cells. In some aspects of these embodiments, the cancer is selected from the group consisting of lung, colorectal, gastric, pancreatic, breast, cervical, bladder, ovarian, brain, head & neck, oral and kidney cancer.

In other embodiments, the present disclosure provides a method of imaging a population of cells in vitro, comprising
a. contacting the cells with a conjugate as described herein to provide labelled cells, and
b. visualizing the labelled cells with a fluorescent light source.

In some embodiments, the disclosure provides a conjugate of the formula VI (also referred to herein as Hypoxyfluor)

In some embodiments, the present disclosure provides a method of imaging a cancer in a subject, comprising a. administering to the subject a conjugate of the formula VI, or a pharmaceutically acceptable salt thereof, to provide the conjugate bound to cancer cells expressing a CA IX protein; b. irradiating the conjugate bound to cancer cells with near-infrared wavelength light, and c. detecting light emitted from the cancer cells at an emission wavelength. In some aspects of these embodiments, the cancer is selected from the group consisting of lung, colorectal, gastric, pancreatic, breast, cervical, bladder, ovarian, brain, head & neck, oral and kidney cancer.

In some embodiments, the present disclosure provides a method of imaging a cancer in a subject, comprising a. administering to the subject a conjugate of the formula VI, or a pharmaceutically acceptable salt thereof, to provide the conjugate bound to cancer cells expressing a CA IX protein;

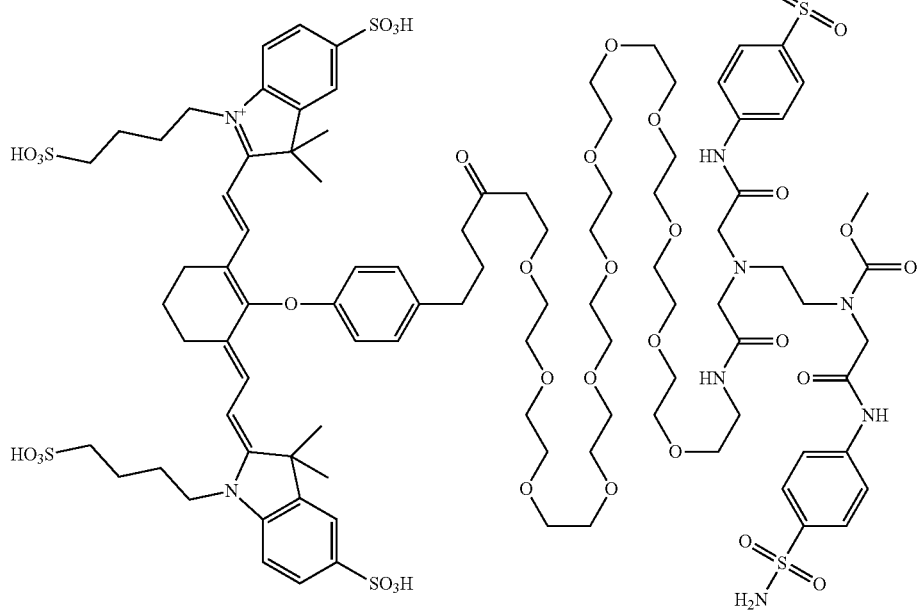

or a pharmaceutically acceptable salt thereof.

In some embodiments, the present disclosure provides a composition comprising a conjugate as described herein, or a pharmaceutically acceptable salt thereof, and optionally at least one pharmaceutically acceptable excipient.

In some embodiments, the present disclosure provides a method of imaging a population of cells in a subject, comprising a. administering to the subject a conjugate of the formula VI, or a pharmaceutically acceptable salt thereof, to provide the conjugate bound to cells expressing a CA IX protein; b. irradiating the conjugate bound to cells by irradiation with near-infrared wavelength light, and c. detecting light emitted from the cells at an emission wavelength.

In some embodiments, the present disclosure provides a method of imaging a population of cells in a subject, comprising a. administering to the subject a conjugate of the formula VI, or a pharmaceutically acceptable salt thereof, to provide the conjugate bound to cells expressing a CA IX protein; and b. visualizing the conjugate bound to cells by irradiation with near-infrared wavelength light.

and b. visualizing the conjugate bound to cancer cells by irradiation with near-infrared wavelength light. In some aspects of these embodiments, the cancer is selected from the group consisting of lung, colorectal, gastric, pancreatic, breast, cervical, bladder, ovarian, brain, head & neck, oral and kidney cancer.

In other embodiments, the present disclosure provides a conjugate of the formula VI, or a pharmaceutically acceptable salt thereof, for use in a method of imaging a cancer in a patient. In some aspects of these embodiments, the method comprises, a. administering to the patient the conjugate, or a pharmaceutically acceptable salt thereof, to provide the conjugate bound to cells expressing a CA IX protein; and b. visualizing the conjugate bound to cells by irradiation with near-infrared wavelength light. In some aspects of these embodiments, the method comprises, a. administering to the subject a conjugate of the formula VI, or a pharmaceutically acceptable salt thereof, to provide the conjugate bound to cancer cells expressing a CA IX protein; b. irradiating the conjugate bound to cancer cells with near-infrared wavelength light, and c. detecting light emitted from the cancer cells at an emission wavelength. In some aspects of these embodiments, the cancer is selected from the group consisting of lung, colorectal, gastric, pancreatic, breast, cervical, bladder, ovarian, brain, head & neck, oral and kidney cancer.

In some embodiments, the present disclosure provides a use of a compound of the formula VI, or a pharmaceutically acceptable salt thereof, in the preparation of a medicament useful for imaging a cancer in a patient. In some aspects of these embodiments, the method comprises, a. administering to the patient the conjugate, or a pharmaceutically acceptable salt thereof, to provide the conjugate bound to cells expressing a CA IX protein; and b. visualizing the conjugate bound to cells by irradiation with near-infrared wavelength light. In some aspects of these embodiments, the method comprises, a. administering to the subject a conjugate of the formula VI, or a pharmaceutically acceptable salt thereof, to provide the conjugate bound to cancer cells expressing a CA IX protein; b. irradiating the conjugate bound to cancer cells with near-infrared wavelength light, and c. detecting light emitted from the cancer cells at an emission wavelength. In some aspects of these embodiments, the cancer is selected from the group consisting of lung, colorectal, gastric, pancreatic, breast, cervical, bladder, ovarian, brain, head & neck, oral and kidney cancer.

In some embodiments, the present disclosure provides a method of imaging a population of cells in vitro, comprising a. contacting the cells with a conjugate of the formula VI to provide labelled cells, and b. visualizing the labelled cells with a fluorescent light source. In some embodiments, the present disclosure provides a method of imaging a population of cells in vitro, comprising a. contacting the cells with a conjugate of the formula VI to provide labelled cells, b. irradiating the conjugate bound to the cells with near-infrared wavelength light, and c. detecting light emitted from the cells at an emission wavelength.

Embodiments of the invention are further described by the following enumerated clauses. It will be understood that any of the embodiments described herein can be used in connection with any other embodiments described herein to the extent that the embodiments do not contradict one another.

1. A conjugate of the formula B-L-A, wherein B is a binding ligand of carbonic anhydrase IX, L is an optional linker, and A is a therapeutic agent and an imaging agent.

2. The conjugate of clause 1, wherein the CA IX ligand is of the formula

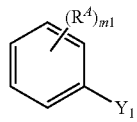

wherein
each $R^A$ is independently selected from the group consisting of H, halogen, —$OR^{1'}$, —$OC(O)R^{1'}$, —$OC(O)NR^{1'}R^{2'}$, —$OS(O)R^{1'}$, —$OS(O)_2R^{1'}$, —$SR^{1'}$, —$S(O)R^{1'}$, —$S(O)_2R^{1'}$, —$S(O)NR^{1'}R^{2'}$, —$S(O)_2NR^{1'}R^{2'}$, —$OS(O)NR^{1'}R^{2'}$, —$OS(O)_2NR^{1'}R^{2'}$, —$NR^{1'}R^{2'}$, —$NR^{1'}C(O)R^{1'}$, —$NR^{1'}C(O)OR^{2'}$, —$NR^{1'}C(O)NR^{1'}R^{2'}$, —$NR^{1'}S(O)R^{2'}$, —$NR^{1'}S(O)_2R^{2'}$, —$NR^{1'}S(O)N$ $R^{1'}R^{2'}$, —$NR^{1'}S(O)_2NR^{1'}R^{2'}$, —$C(O)R^{1'}$, —$C(O)OR^{1'}$, and —$C(O)NR^{1'}R^{2'}$;

$Y_1$ is —$OR^B$, —$SR^B$, —$NR^BR^{B'}$, —$S(O)_2R^B$, —$NR^BC(O)R^{B'}$ or —$NR^BC(O)NR^BR^{B'}$;

each $R^B$ and $R^{B'}$ is independently H, $C_1$-$C_{10}$ alkyl, $C_2$-$C_{10}$ alkenyl or phenyl; wherein each hydrogen atom in $C_1$-$C_{10}$ alkyl, $C_2$-$C_{10}$ alkenyl, and phenyl is optionally substituted with —CN, $C_1$-$C_6$ alkyl-(5- to 9-membered heteroaryl), —$NR^{3'}R^{4'}$, —$NR^{3'}(CH_2)_{m2}NR^{3'}R^{4'}$ or —$C_6H_4OR^{3'}$;

each $R^{3'}$ and $R^{4'}$ is independently H, —$CH_2C(O)^*$, —$CH_2C(O)OR^{5'}$, —$CH_2C(O)NR^{5'}R^{6'}$, or a bond to the rest of the conjugate;

each $R^{5'}$ and $R^{6'}$ is independently H, $C_1$-$C_8$ alkyl, or phenyl, wherein each hydrogen atom in wherein each hydrogen atom in $C_1$-$C_{10}$ alkyl, $C_2$-$C_{10}$ alkenyl, and phenyl is optionally substituted with $C_1$-$C_6$ alkyl-(phenyl), —$OR^{1'}$, —$OC(O)R^{1'}$, —$OC(O)NR^{1'}R^{2'}$, —$OS(O)R^{1'}$, —$OS(O)_2R^{1'}$, —$SR^{1'}$, —$S(O)R^{1'}$, —$S(O)_2R^{1'}$, —$S(O)NR^{1'}R^{2'}$, —$S(O)_2NR^{1'}R^{2'}$, —$OS(O)NR^{1'}R^{2'}$, —$OS(O)_2NR^{1'}R^{2'}$, —$NR^{1'}R^{2'}$, —$NR^{1'}C(O)R^{1'}$, —$NR^{1'}C(O)OR^{2'}$, —$NR^{1'}C(O)NR^{1'}R^{2'}$, —$NR^{1'}S(O)R^{2'}$, —$NR^{1'}S(O)_2R^{2'}$, —$NR^{1'}S(O)N$ $R^{1'}R^{2'}$, —$NR^{1'}S(O)_2NR^{1'}R^{2'}$, —$C(O)R^{1'}$, —$C(O)OR^{1'}$, and —$C(O)NR^{1'}R^{2'}$;

each $R^{1'}$ and $R^{2'}$ is independently selected from the group consisting of H, $C_1$-$C_6$ alkyl, $C_2$-$C_6$ alkenyl, $C_2$-$C_6$ alkynyl, and $C_3$-$C_9$ cycloalkyl;

m1 is 1, 2, 3, 4 or 5; and
* represents a covalent bond to the rest of the conjugate.

3. The conjugate of clause 2, or a pharmaceutically acceptable salt thereof, wherein the CA IX ligand is selected from the group consisting of

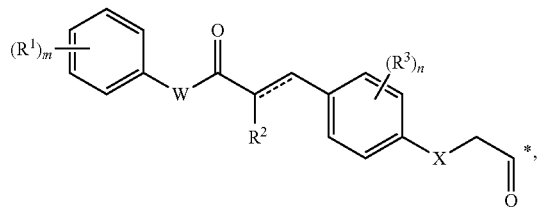

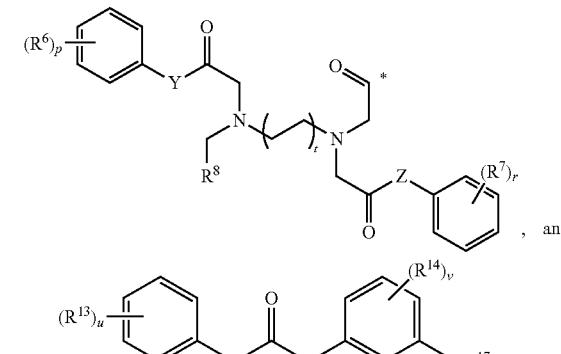

, and

wherein each $R^1$ and $R^3$ is independently selected from the group consisting of H, $OR^4$, —$OC(O)R^4$, —$OC(O)NR^4R^5$, —$OS(O)R^4$, —$OS(O)_2R^4$, —$SR^4$, —$S(O)R^4$, —$S(O)_2R^4$, —$S(O)NR^4R^5$, —$S(O)_2NR^4R^5$, —$OS(O)NR^4R^5$, —$OS(O)_2NR^4R^5$, —$NR^4R^5$, —$NR^4C(O)R^5$, —$NR^4C(O)OR^5$, —$NR^4C(O)NR^4R^5$, —$NR^4S(O)R^5$, —$NR^4S(O)_2R^5$, —$NR^4S(O)NR^4R^5$, —$NR^4S(O)_2NR^4R^5$, —$C(O)R^4$, —$C(O)OR^4$, and —$C(O)NR^4R^5$;

$R^2$ is selected from the group consisting of H, —CN, $C_1$-$C_6$ alkyl, $C_2$-$C_6$ alkenyl, and $C_2$-$C_6$ alkynyl;

W is —O—, —$CH_2$— or —$NR^4$—;

X is —O—, —$CH_2$— or —$NR^S$—;

each $R^4$, $R^5$, $R^{4'}$ and $R^{5'}$ is independently selected from the group consisting of H, $C_1$-$C_6$ alkyl, $C_2$-$C_6$ alkenyl, and $C_2$-$C_6$ alkynyl;

m is an integer from 1 to 4; and
n is an integer from 0 to 2;

wherein each $R^6$ and $R^7$ is independently selected from the group consisting of H, $OR^9$, —$OC(O)R^9$, —$OC(O)NR^9R^{10}$, —$OS(O)R^9$, —$OS(O)_2R^9$, —$SR^9$, —$S(O)R^9$, —$S(O)_2R^9$, —$S(O)NR^9R^{10}$, —$S(O)_2NR^9R^{10}$, —$OS(O)NR^9R^{10}$, —$OS(O)_2NR^9R^{10}$, —$NR^9R^{10}$, —$NR^9C(O)R^{10}$, —$NR^9C(O)OR^{10}$, —$NR^9C(O)NR^9R^{10}$, —$NR^9S(O)R^{10}$, —$NR^9S(O)_2R^{10}$, -$NR^9S(O)NR^9R^{10}$, —$NR^9S(O)_2NR^9R^{10}$, —$C(O)R^9$, —$C(O)OR^9$, and —$C(O)NR^9R^{10}$;

$R^8$ is selected from the group consisting of H, $C_1$-$C_6$ alkyl, $C_2$-$C_6$ alkenyl, and $C_2$-$C_6$ alkynyl, —$C(O)R^{11}$, —$C(O)OR^{11}$, and —$C(O)NR^{11}R^{12}$ Y is —O—, —$CH_2$— or —$NR^{9'}$—;

Z is —O—, —$CH_2$— or —$NR^{10'}$—;

each $R^9$, $R^{10}$, $R^{9'}$, $R^{10'}$ $R^{11}$ and $R^{12}$ is independently selected from the group consisting of H, $C_1$-$C_6$ alkyl, $C_2$-$C_6$ alkenyl, and $C_2$-$C_6$ alkynyl;

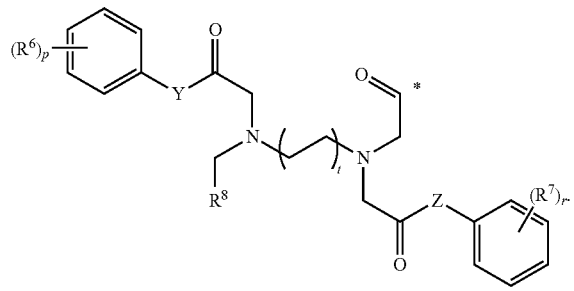

6. The conjugate of clause 5, or a pharmaceutically acceptable salt thereof, wherein the CA IX ligand is of the formula

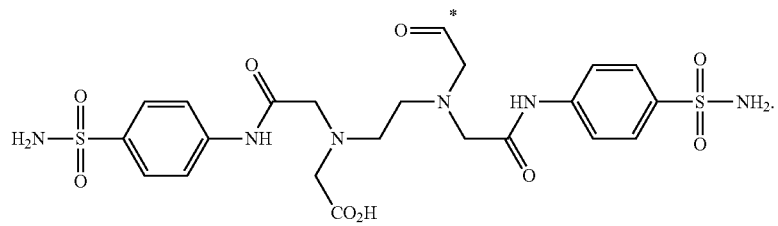 [SMILES: NS(=O)(=O)c1ccc(NC(=O)CN(CC=O)CCN(CC(=O)O)CC(=O)Nc2ccc(S(N)(=O)=O)cc2)cc1]

p is an integer from 1 to 4;

r is an integer from 0 to 4; and t is an integer from 1 to 3;

wherein each $R^{13}$ and $R^{14}$ is independently selected from the group consisting of H, —$OR^{15}$, —$OC(O)R^{15}$, —$OC(O)NR^{15}R^{16}$, —$OS(O)R^{15}$, —$OS(O)_2R^{15}$, —$SR^{15}$, —$S(O)R^{15}$, —$S(O)_2R^{15}$, —$S(O)NR^{15}R^{16}$, —$S(O)_2NR^{15}R^{16}$, $OS(O)NR^{15}R^{16}$, —$OS(O)_2NR^{15}R^{16}$, —$NR^{15}R^{16}$, $NR^{15}C(O)R^{16}$, —$NR^{15}C(O)OR^{16}$, —$NR^{15}C(O)NR^{15}R^{16}$, —$NR^{15}S(O)R^{16}$, —$NR^{15}S(O)_2R^{16}$, —$NR^{15}S(O)NR^{15}R^{16}$, —$NR^{15}S(O)_2NR^{15}R^{16}$, —$C(O)R^{15}$, —$C(O)OR^{15}$, and —$C(O)NR^{15}R^{16}$;

$W_1$ is —O—, —$CH_2$— or —$NR^{15'}$—;

$X_1$ is —O—, —$CH_2$— or —$NR^{16'}$—;

each $R^{15}$, $R^{16}$ $R^{15'}$, $R^{16'}$ and $R^{17}$ is independently selected from the group consisting of H, $C_1$-$C_6$ alkyl, $C_2$-$C_6$ alkenyl, and $C_2$-$C_6$ alkynyl;

u is an integer from 1 to 4; and v is an integer from 0 to 2; and each * represents a covalent bond to the rest of the conjugate.

4. The conjugate of clause 3, or a pharmaceutically acceptable salt thereof, wherein the CA IX ligand is of the formula

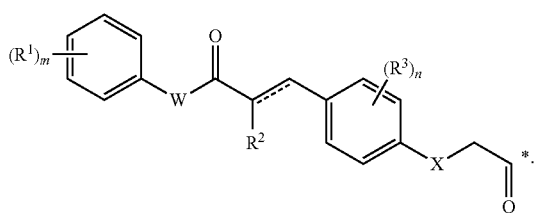

5. The conjugate of clause 3, or a pharmaceutically acceptable salt thereof, wherein the CA IX ligand is of the formula 7. The conjugate of clause 3, or a pharmaceutically acceptable salt thereof, wherein the CA IX ligand is of the formula

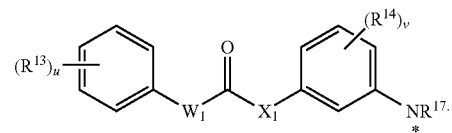

8. The conjugate of clause 7, or a pharmaceutically acceptable salt thereof, wherein the CA IX ligand is of the formula

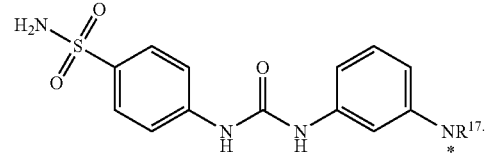

9. The conjugate of any one of the preceding clauses, or a pharmaceutically acceptable salt thereof, wherein the linker comprises a portion selected from the group consisting of —$C(O)(C_1$-$C_{12}$ alkyl)$C(O)$—, —NH—$C_1$-$C_{12}$ alkyl-NH—, —$N(C_1$-$C_6$ alkyl)-$C_1$-$C_{12}$ alkyl-$N(C_1$-$C_6$ alkyl)-, —$C(O)CH_2CH_2(OCH_2CH_2)_q$NH—, —$C(O)CH_2CH_2(OCH_2CH_2)_{q3}N(C_1$-$C_6$ alkyl)-, —$NH(CH_2CH_2O)_{q2}CH_2CH_2C(O)$—, and —$N(C_1$-$C_6$ alkyl)$(CH_2CH_2O)_{q3}CH_2CH_2C(O)$—; wherein each of q, q1, q2 and q3 is an integer from 1 to 40.

10. The conjugate of clause 3 or 4, or a pharmaceutically acceptable salt thereof, comprising the formula

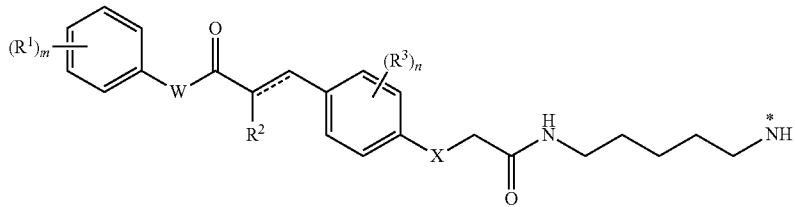

wherein * represents a covalent bond to the rest of the conjugate.

11. The conjugate of clause 1, 2, 3, 4 or 10, or a pharmaceutically acceptable salt thereof, comprising the formula

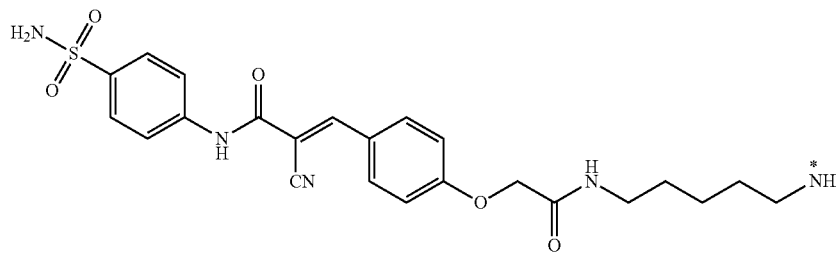

wherein * represents a covalent bond to the rest of the conjugate.

12. The conjugate of clause 3 or 5, or a pharmaceutically acceptable salt thereof, comprising the formula

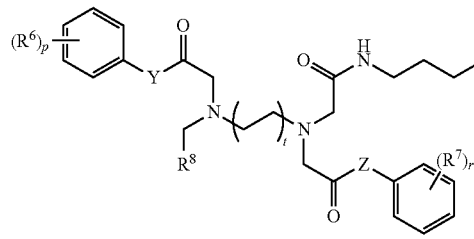

wherein * represents a covalent bond to the rest of the conjugate.

13. The conjugate of clause 1, 2, 3, 5, 6 or 12, or a pharmaceutically acceptable salt thereof, comprising the formula

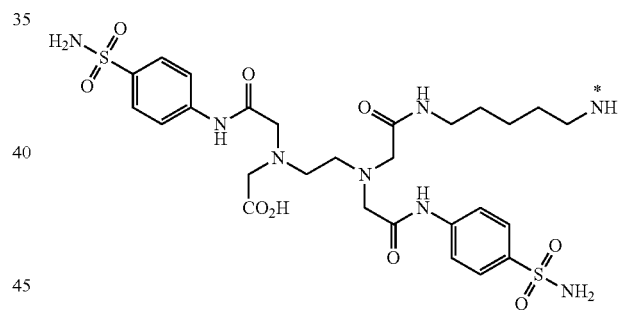

wherein * represents a covalent bond to the rest of the conjugate.

14. The conjugate of clause 3 or 7, or a pharmaceutically acceptable salt thereof, comprising the formula

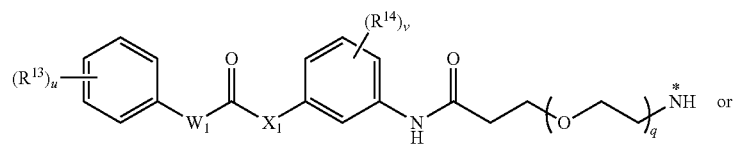

or

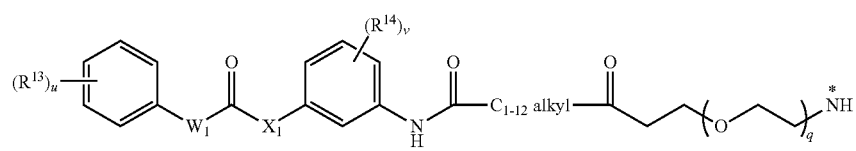

wherein q is an integer from 1 to 40, and * represents a covalent bond to the rest of the conjugate.

15. The conjugate of clause 1, 2, 3, 7, 8 or 14, or a pharmaceutically acceptable salt thereof, comprising the formula

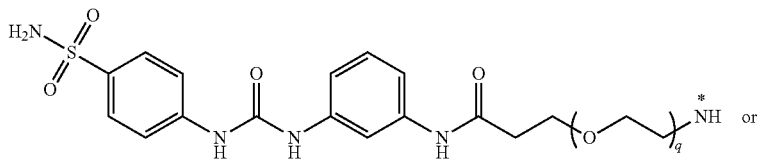 or

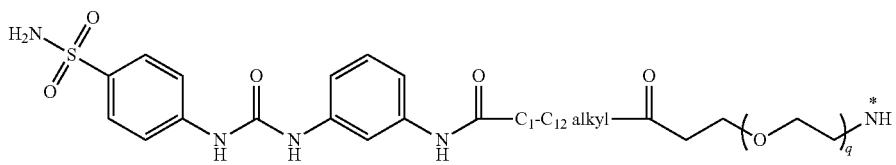

wherein q is an integer from 1 to 40, and * represents a covalent bond to the rest of the conjugate.

16. The conjugate of clause 14 or 15, or a pharmaceutically acceptable salt thereof, wherein q is 4.

17. The conjugate of clause 14 or 15, or a pharmaceutically acceptable salt thereof, wherein q is 12.

18. The conjugate of clause 14 or 15, or a pharmaceutically acceptable salt thereof, wherein q is 36.

19. The conjugate of clause 3 or 5, or a pharmaceutically acceptable salt thereof, comprising the formula

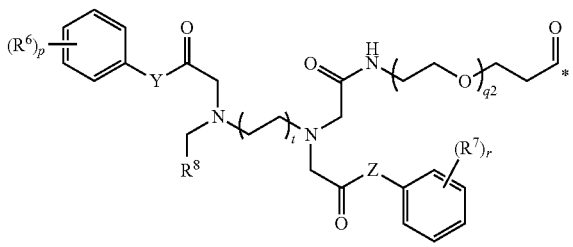

wherein q2 is an integer from 1 to 40, and * represents a covalent bond to the rest of the conjugate.

20. The conjugate of clause 1, 2, 3, 5, 6 or 19, or a pharmaceutically acceptable salt thereof, comprising the formula

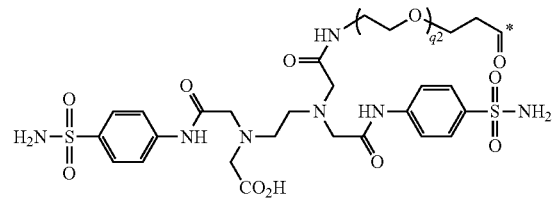

wherein q2 is an integer from 1 to 40, and * represents a covalent bond to the rest of the conjugate.

21. The conjugate of clause 19 or 20, or a pharmaceutically acceptable salt thereof, wherein q2 is 4.

22. The conjugate of clause 19 or 20, or a pharmaceutically acceptable salt thereof, wherein q2 is 12.

23. The conjugate of clause 19 or 20, or a pharmaceutically acceptable salt thereof, wherein q2 is 36.

24. The conjugate of clause 3 or 5, or a pharmaceutically acceptable salt thereof, comprising the formula

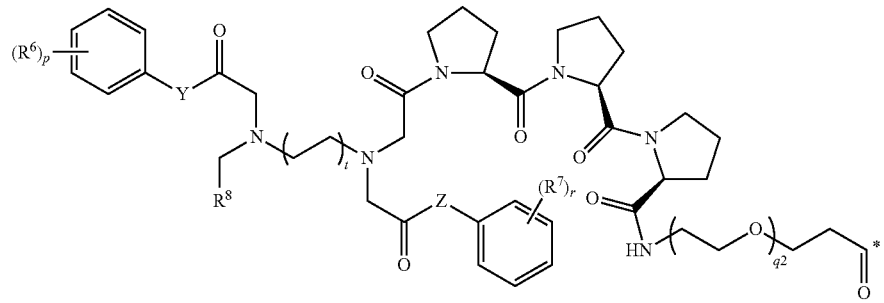

wherein q2 is an integer from 1 to 40, and * represents a covalent bond to the rest of the conjugate.

25. The conjugate of clause 1, 2, 3, 5, 6 or 24, or a pharmaceutically acceptable salt thereof, comprising the formula

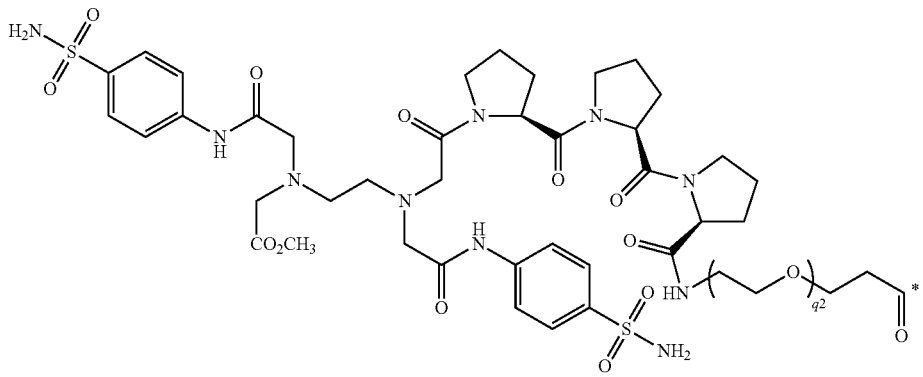

wherein q2 is an integer from 1 to 40, and * represents a covalent bond to the rest of the conjugate.

26. The conjugate of clause 24 or 25, or a pharmaceutically acceptable salt thereof, wherein q2 is 4.
27. The conjugate of clause 24 or 25, or a pharmaceutically acceptable salt thereof, wherein q2 is 12.
28. The conjugate of clause 24 or 25, or a pharmaceutically acceptable salt thereof, wherein q2 is 36.
29. The conjugate of any one of the preceding clauses, or a pharmaceutically acceptable salt thereof, wherein the agent is a SPECT imaging agent.
30. The conjugate of any one of the preceding clauses, or a pharmaceutically acceptable salt thereof, wherein the agent is a SPECT imaging agent of the formula

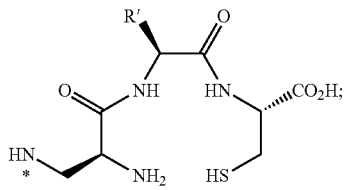

wherein R' is H, or R' is selected from the group consisting of $C_1$-$C_6$ alkyl, amino-$C_1$-$C_6$ alkyl, carboxy-$C_1$-$C_6$ alkyl, hydroxyl-$C_1$-$C_6$ alkyl, $C_1$-$C_6$heteroalkyl, $C_6$-$C_{10}$ aryl, $C_6$-$C_{10}$ aryl-$C_1$-$C_6$ alkyl alkyl and $C_5$-$C_{10}$ heteroaryl-$C_1$-$C_6$ alkyl; and * represents a covalent bond to the rest of the conjugate.

31. The conjugate of clause 30, or a pharmaceutically acceptable salt thereof, wherein a radionuclei is bound to the conjugate.
32. The conjugate of any one of clauses 1 to 29, or a pharmaceutically acceptable salt thereof, wherein the agent is a SPECT imaging agent of the formula

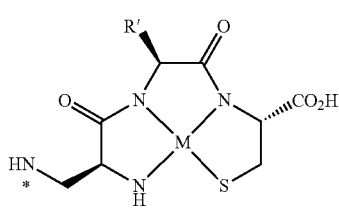

wherein M is a cation of a radionuclide, R' is H, or R' is selected from the group consisting of $C_1$-$C_6$ alkyl, amino-$C_1$-$C_6$ alkyl, carboxy-$C_1$-$C_6$ alkyl, hydroxyl-$C_1$-$C_6$ alkyl, $C_1$-$C_6$ hetero alkyl, $C_6$-$C_{10}$ aryl, $C_6$-$C_{10}$ aryl-$C_1$-$C_6$ alkyl and $C_5$-$C_{10}$ heteroaryl-$C_1$-$C_6$ alkyl and * represents a covalent bond to the rest of the conjugate.

33. The conjugate of clause 31 or 32, or a pharmaceutically acceptable salt thereof, wherein the radionuclei is selected from the group consisting of an isotope of gallium, an isotope of indium, an isotope of copper, an isotope of technetium, and an isotope of rhenium.
34. The conjugate of clause 33, or a pharmaceutically acceptable salt thereof, wherein the radionuclei is an isotope of technetium.
35. The conjugate of clause 34, or a pharmaceutically acceptable salt thereof, wherein the radionuclei is $^{99m}$Tc.
36. The conjugate of any one of clauses 1 to 29, or a pharmaceutically acceptable salt thereof, wherein the agent is a SPECT imaging agent of the formula

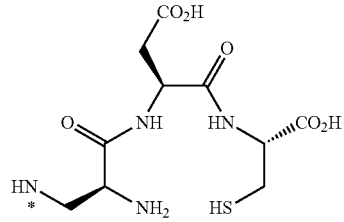 [SMILES: NC[C@H](N)C(=O)N[C@@H](CC(=O)O)C(=O)N[C@@H](CS)C(=O)O]

wherein * represents a covalent bond to the rest of the conjugate.

37. The conjugate of clause 36, or a pharmaceutically acceptable salt thereof, wherein a radionuclei is bound to the conjugate.
38. The conjugate of any one of clauses 1 to 29, or a pharmaceutically acceptable salt thereof, wherein the agent is a SPECT imaging agent of the formula

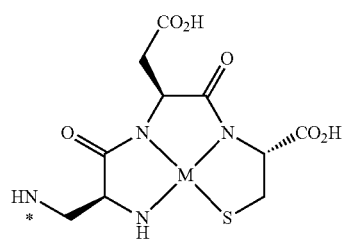

wherein M is a cation of a radionuclide, and * represents a covalent bond to the rest of the conjugate.

39. The conjugate of clause 37 or 38, or a pharmaceutically acceptable salt thereof, wherein the radionuclei is selected from the group consisting of an isotope of gallium, an isotope of indium, an isotope of copper, an isotope of technetium, and an isotope of rhenium.

40. The conjugate of clause 39, or a pharmaceutically acceptable salt thereof, wherein the radionuclei is an isotope of technetium.

41. The conjugate of clause 40, or a pharmaceutically acceptable salt thereof, wherein the radionuclei is $^{99m}$Tc.

42. The conjugate of any one of clauses 1 to 28, or a pharmaceutically acceptable salt thereof, wherein the agent is an imaging agent.

43. The conjugate of clause 42, or a pharmaceutically acceptable salt thereof, wherein the imaging agent is a rhodamine dye.

44. The conjugate of clause 1, selected from the group consisting of

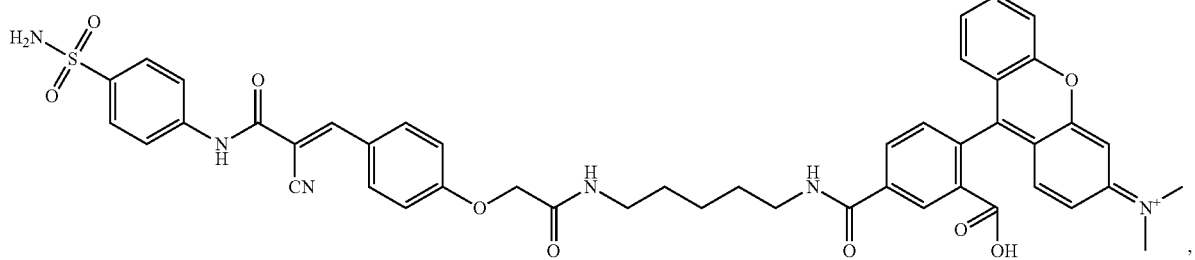

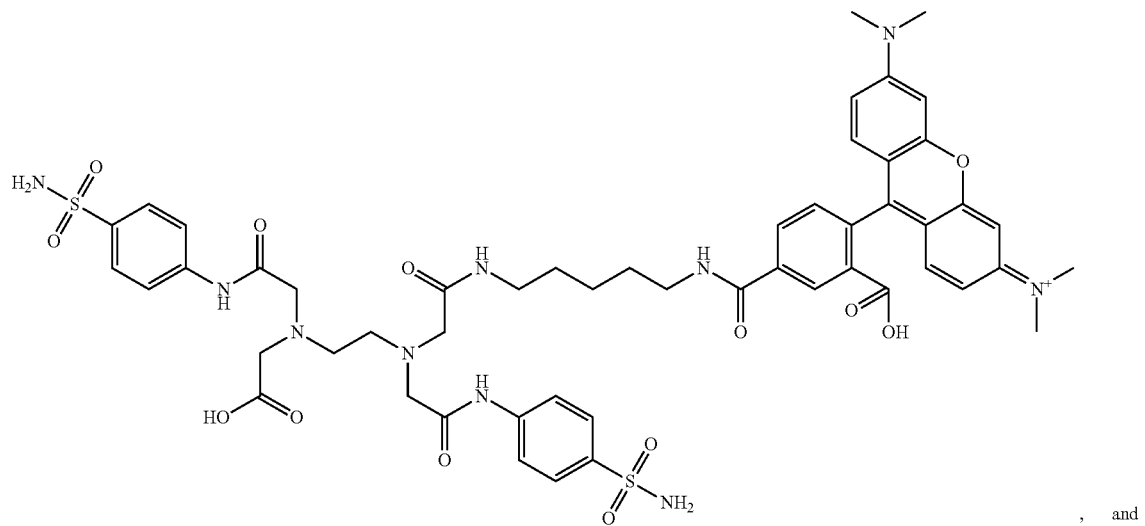

, and

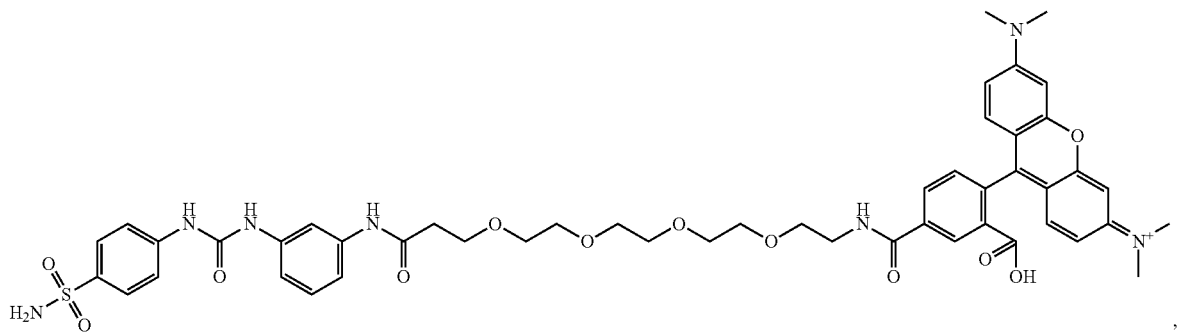

, or a pharmaceutically acceptable salt thereof.

45. The conjugate of clause 1, selected from the group consisting of
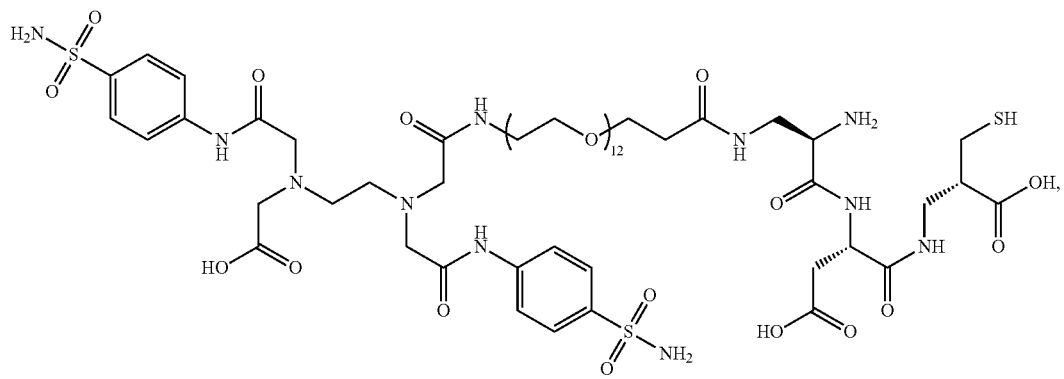
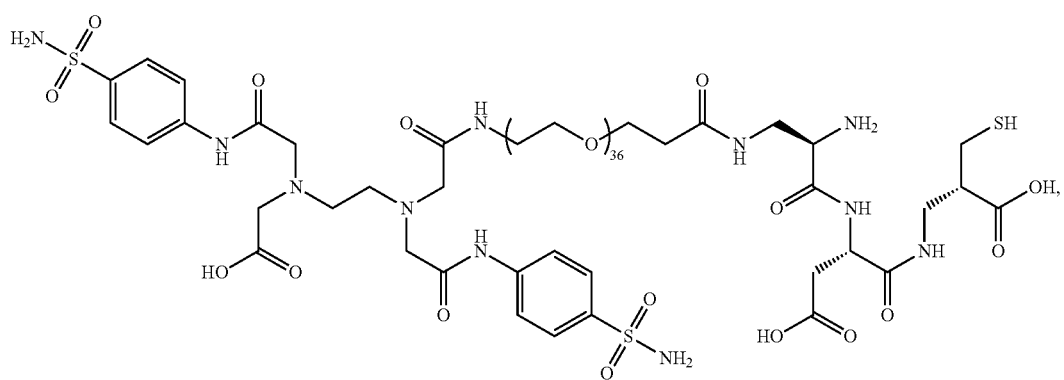
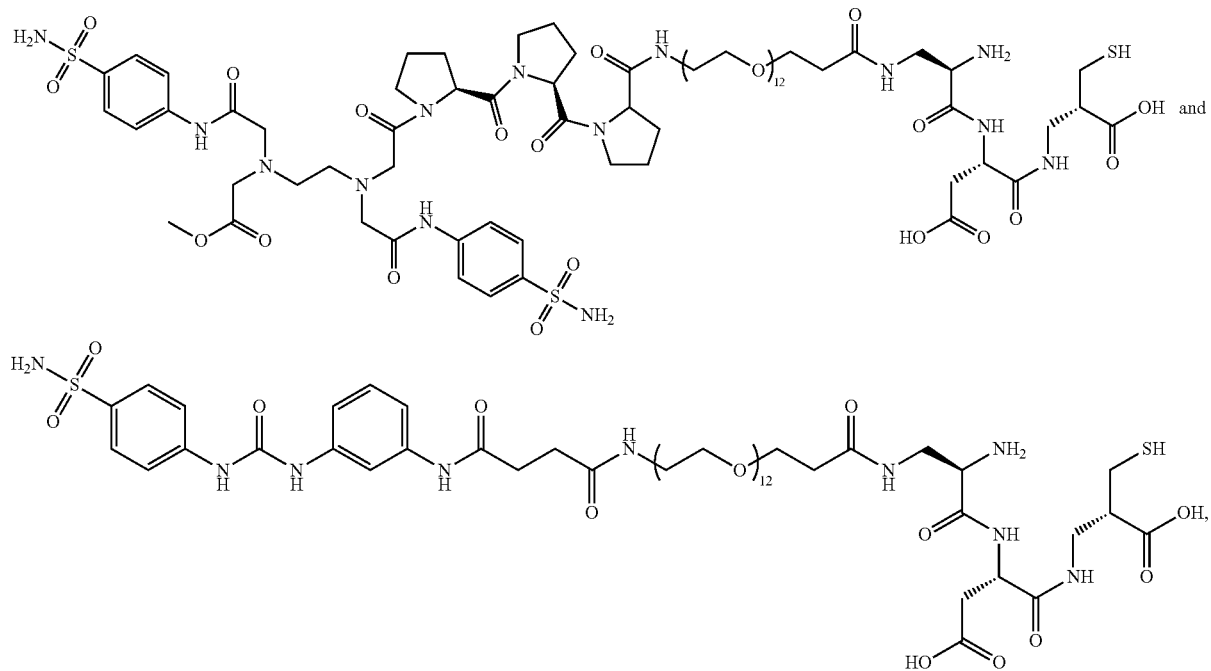
or a pharmaceutically acceptable salt thereof.

46. The conjugate of clause 45, selected from the group consisting of
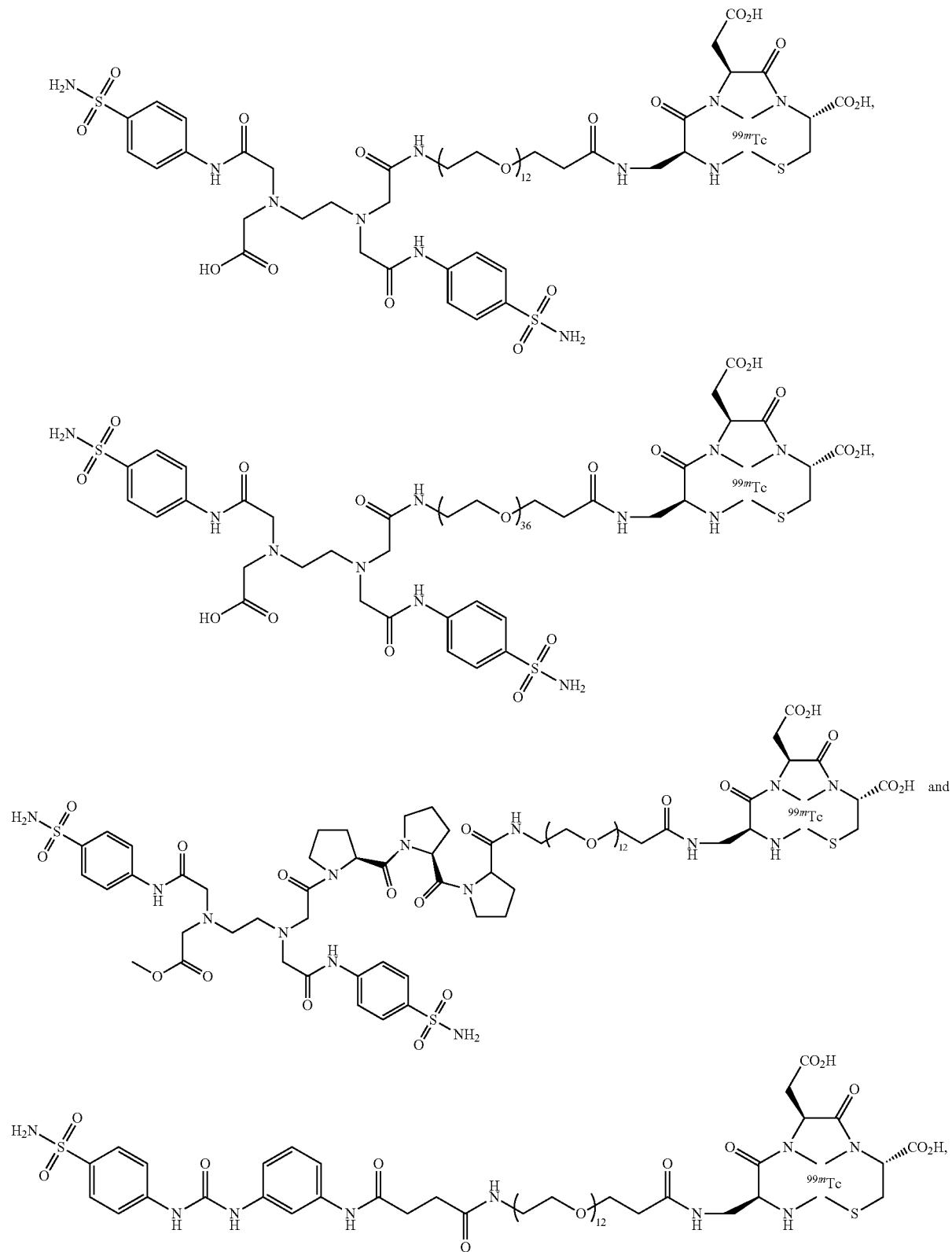
or a pharmaceutically acceptable salt thereof.

47. The conjugate of any one of clauses 1 to 9, or a pharmaceutically acceptable salt thereof, wherein the linker comprises at least one amino acid.

48. The conjugate of any one of clauses 1 to 9, or a pharmaceutically acceptable salt thereof, wherein the linker comprises at least one amino acid selected from the group consisting of DAP, Pro, Asp and Cys.

49. The conjugate of clause 47 or 48, or a pharmaceutically acceptable salt thereof, wherein the linker comprises three proline amino acids.

50. The conjugate of clause 47 or 48, or a pharmaceutically acceptable salt thereof, wherein the linker comprises the amino acid sequence DAP-Asp.

51. The conjugate of any one of clauses 1 to 28 or 47 to 50, or a pharmaceutically acceptable salt thereof, wherein the linker comprises a releasable linker.

52. The conjugate of clause 51, or a pharmaceutically acceptable salt thereof, wherein the releasable linker comprises a disulfide bond.

53. The conjugate of clause 51 or 52, or a pharmaceutically acceptable salt thereof, wherein the releasable linker comprises a portion having the formula

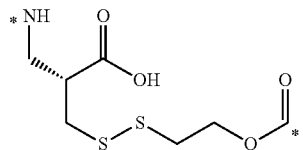 [SMILES: NC[C@@H](CSSCCOC=O)C(=O)O]

wherein each * represents a covalent bond to the rest of the conjugate.

54. The conjugate of any one of clauses 1 to 28 or 47 to 53, or a pharmaceutically acceptable salt thereof, wherein the linker comprises a hydrazide portion.

55. The conjugate of any one of clauses 2, 5, 19 or 21 to 23, or a pharmaceutically acceptable salt thereof, comprising the formula

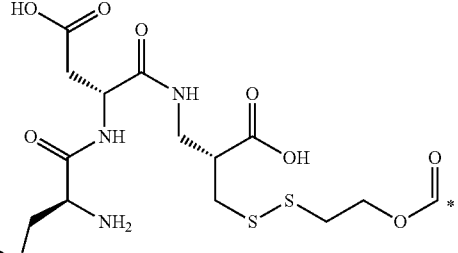

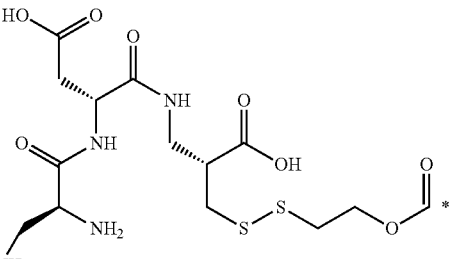

wherein q2 is an integer from 1 to 40, and * represents a covalent bond to the rest of the conjugate.

56. The conjugate of any one of clauses 2, 5, 6 or 19 to 23, or a pharmaceutically acceptable salt thereof, comprising the formula

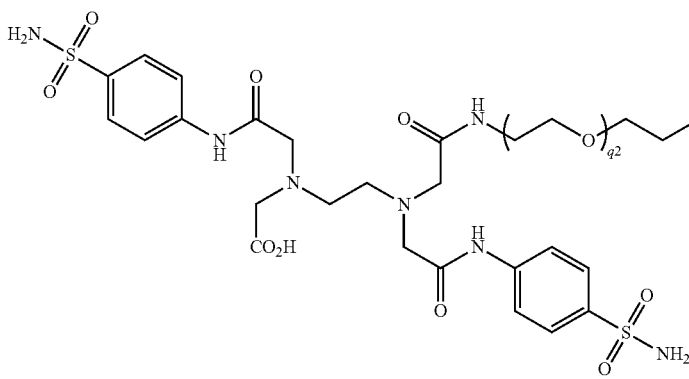

wherein q2 is an integer from 1 to 40, and * represents a covalent bond to the rest of the conjugate.

57. The conjugate of any one of clause 1 to 28 or 47 to 56, or a pharmaceutically acceptable salt thereof, wherein the agent is a therapeutic agent.

58. The conjugate of clause 57, or a pharmaceutically acceptable salt thereof, wherein the therapeutic agent is a tubulysin.

59. The conjugate of clause 1, having the formula

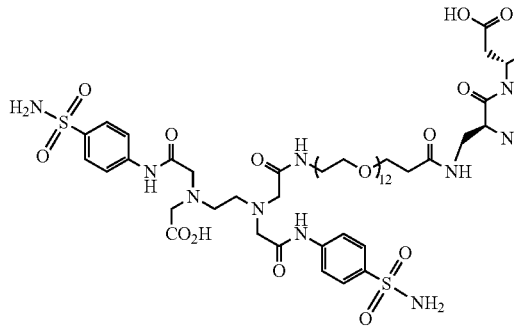
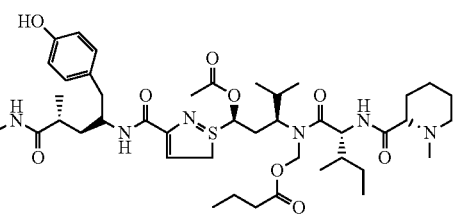

or a pharmaceutically acceptable salt thereof.

60. A method of imaging a population of cells in a subject, comprising
a. administering to the subject an effective amount of a conjugate of the formula B-L-A, wherein B is a CA IX ligand, L is an optional linker, and A is a therapeutic agent and an imaging agent.

61. The method of clause 67, wherein the CA IX ligand is of the formula

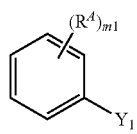

wherein
each $R^A$ is independently selected from the group consisting of H, halogen, —$OR^{1'}$, —$OC(O)R^{1'}$, —$OC(O)NR^{1'}R^{2'}$, —$OS(O)R^{1'}$, —$OS(O)_2R^{1'}$, —$SR^{1'}$, —$S(O)R^{1'}$, —$S(O)_2R^{1'}$, —$S(O)NR^{1'}R^{2'}$, —$S(O)_2NR^{1'}R^{2'}$, —$OS(O)NR^{1'}R^{2'}$, —$OS(O)_2NR^{1'}R^{2'}$, —$NR^{1'}R^{2'}$, —$NR^{1'}C(O)R^{1'}$, —$NR^{1'}C(O)OR^{2'}$, —$NR^{1'}C(O)NR^{1'}R^{2'}$, —$NR^{1'}S(O)R^{2'}$, —$NR^{1'}S(O)_2R^{2'}$, —$NR^{1'}S(O)N\ R^{1'}R^{2'}$, —$NR^{1'}S(O)_2NR^{1'}R^{2'}$, —$C(O)R^{1'}$, —$C(O)OR^{1'}$, and —$C(O)NR^{1'}R^{2'}$;

$Y_1$ is —$OR^B$, —$SR^B$, —$NR^BR^{B'}$, —$S(O)_2R^B$, —$NR^BC(O)R^{B'}$ or —$NR^BC(O)NR^BR^{B'}$;

each $R^B$ and $R^{B'}$ is independently H, $C_1$-$C_{10}$ alkyl, $C_2$-$C_{10}$ alkenyl or phenyl; wherein each hydrogen atom in $C_1$-$C_{10}$ alkyl, $C_2$-$C_{10}$ alkenyl, and phenyl is optionally substituted with —CN, $C_1$-$C_6$ alkyl-(5- to 9-membered heteroaryl), —$NR^{3'}R^{4'}$, —$NR^{3'}(CH_2)_{m2}NR^{3'}R^{4'}$ or —$C_6H_4OR^{3'}$;

each $R^{3'}$ and $R^{4'}$ is independently H, —$CH_2C(O)$*, —$CH_2C(O)OR^5$, —$CH_2C(O)NR^5R^6$, or a bond to the rest of the conjugate;

each $R^{5'}$ and $R^{6'}$ is independently H, $C_1$-$C_8$ alkyl, or phenyl, wherein each hydrogen atom in wherein each hydrogen atom in $C_1$-$C_{10}$ alkyl, $C_2$-$C_{10}$ alkenyl, and phenyl is optionally substituted with $C_1$-$C_6$ alkyl-(phenyl), —$OR^{1'}$, —$OC(O)R^{1'}$, —$OC(O)NR^{1'}R^{2'}$, —$OS(O)R^{1'}$, —$OS(O)_2R^{1'}$, —$SR^{1'}$, —$S(O)R^{1'}$, —$S(O)_2R^{1'}$, —$S(O)NR^{1'}R^{2'}$, —$S(O)_2NR^{1'}R^{2'}$, —$OS(O)NR^{1'}R^{2'}$, —$OS(O)_2NR^{1'}R^{2'}$, —$NR^{1'}R^{2'}$, —$NR^{1'}C(O)R^{1'}$, —$NR^{1'}C(O)OR^{2'}$, —$NR^{1'}C(O)NR^{1'}R^{2'}$, —$NR^{1'}S(O)R^{2'}$, —$NR^{1'}S(O)_2R^{2'}$, —$NR^{1'}S(O)N\ R^{1'}R^{2'}$, —$NR^{1'}S(O)_2NR^{1'}R^{2'}$, —$C(O)R^{1'}$, —$C(O)OR^{1'}$, and —$C(O)NR^{1'}R^{2'}$;

each $R^{1'}$ and $R^{2'}$ is independently selected from the group consisting of H, $C_1$-$C_6$ alkyl, $C_2$-$C_6$ alkenyl, $C_2$-$C_6$ alkynyl, and $C_3$-$C_9$ cycloalkyl;

m1 is 1, 2, 3, 4 or 5; and
* represents a covalent bond to the rest of the conjugate.

62. The method of clause 60 or 61, wherein the CA IX ligand is selected from the group consisting of

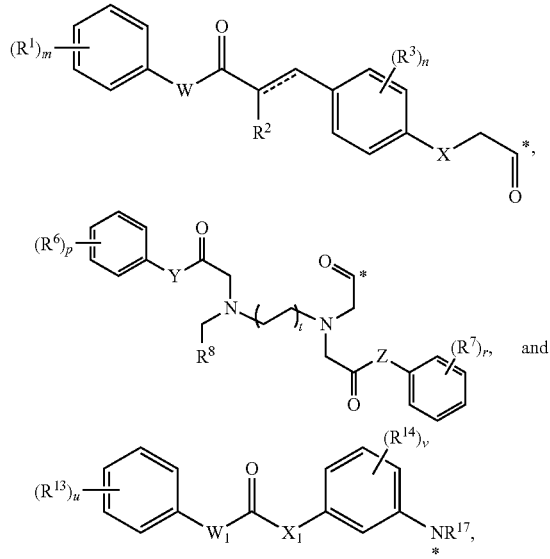

wherein each $R^1$ and $R^3$ is independently selected from the group consisting of H, $OR^4$, —$OC(O)R^4$, —$OC(O)NR^4R^5$, —$OS(O)R^4$, —$OS(O)_2R^4$, —$SR^4$, —$S(O)R^4$, —$S(O)_2R^4$, —$S(O)NR^4R^5$, —$S(O)_2NR^4R^5$, —$OS(O)NR^4R^5$, —$OS(O)_2NR^4R^5$, —$NR^4R^5$, —$NR^4C(O)R^5$, —$NR^4C(O)OR^5$, —$NR^4C(O)NR^4R^5$, —$NR^4S(O)R^5$, —$NR^4S(O)_2R^5$, —$NR^4S(O)NR^4R^5$, —$NR^4S(O)_2NR^4R^5$, —$C(O)R^4$, —$C(O)OR^4$, and —$C(O)NR^4R^5$;

$R^2$ is selected from the group consisting of H, —CN, $C_1$-$C_6$ alkyl, $C_2$-$C_6$ alkenyl, and $C_2$-$C_6$ alkynyl;

W is —O—, —$CH_2$— or —$NR^4$—;

X is —O—, —$CH_2$— or —$NR^S$—;

each $R^4$, $R^5$, $R^{4'}$ and $R^{5'}$ is independently selected from the group consisting of H, $C_1$-$C_6$ alkyl, $C_2$-$C_6$ alkenyl, and $C_2$-$C_6$ alkynyl;

m is an integer from 1 to 4; and n is an integer from 0 to 2;

wherein each $R^6$ and $R^7$ is independently selected from the group consisting of H, $OR^9$, —$OC(O)R^9$, —$OC(O)NR^9R^{10}$, —$OS(O)R^9$, —$OS(O)_2R^9$, —$SR^9$, —$S(O)R^9$, —$S(O)_2R^9$, —$S(O)NR^9R^{10}$, —$S(O)_2NR^9R^{10}$, —$OS(O)NR^9R^{10}$, —$OS(O)_2NR^9R^{10}$, —$NR^9R^{10}$, —$NR^9C(O)R^{10}$, —$NR^9C(O)OR^{10}$, —$NR^9C(O)NR^9R^{10}$, —$NR^9S(O)R^{10}$, —$NR^9S(O)_2R^{10}$, —$NR^9S(O)NR^9R^{10}$, —$NR^9S(O)_2NR^9R^{10}$, —$C(O)R^9$, —$C(O)OR^9$, and —$C(O)NR^9R^{10}$;

$R^8$ is selected from the group consisting of H, $C_1$-$C_6$ alkyl, $C_2$-$C_6$ alkenyl, and $C_2$-$C_6$ alkynyl, —$C(O)R^{11}$, —$C(O)OR^{11}$, and —$C(O)NR^{11}R^{12}$ Y is —O—, —$CH_2$— or —$NR^{9'}$;

Z is —O—, —$CH_2$— or —$NR^{10'}$—;

each $R^9$, $R^{10}$, $R^{9'}$, $R^{10'}$, $R^{11}$ and $R^{12}$ is independently selected from the group consisting of H, $C_1$-$C_6$ alkyl, $C_2$-$C_6$ alkenyl, and $C_2$-$C_6$ alkynyl;

p is an integer from 1 to 4;

r is an integer from 0 to 4; and t is an integer from 1 to 3;

wherein each $R^{13}$ and $R^{14}$ is independently selected from the group consisting of H, —$OR^{15}$, —$OC(O)R^{15}$, —$OC(O)NR^{15}R^{16}$, —$OS(O)R^{15}$, —$OS(O)_2R^{15}$, —$SR^{15}$, —$S(O)R^{15}$, —$S(O)_2R^{15}$, —$S(O)NR^{15}R^{16}$, —$S(O)_2NR^{15}R^{16}$, —$OS(O)NR^{15}R^{16}$, —$OS(O)_2NR^{15}R^{16}$, —$NR^{15}R^{16}$, —$NR^{15}C(O)R^{16}$, —$NR^{15}C(O)OR^{16}$, —$NR^{15}C(O)NR^{15}R^{16}$, —$NR^{15}S(O)R^{16}$, —$NR^{15}S(O)_2R^{16}$, —$NR^{15}S(O)NR^{15}R^{16}$, —$NR^{15}S(O)_2NR^{15}R^{16}$, —$C(O)R^{15}$, —$C(O)OR^{15}$, and —$C(O)NR^{15}R^{16}$;

$W_1$ is —O—, —$CH_2$— or —$NR^{15'}$—;

$X_1$ is —O—, —$CH_2$— or —$NR^{16'}$—;

each $R^{15}$, $R^{16}$, $R^{15'}$, $R^{16'}$ and $R^{17}$ is independently selected from the group consisting of H, $C_1$-$C_6$ alkyl, $C_2$-$C_6$ alkenyl, and $C_2$-$C_6$ alkynyl;

u is an integer from 1 to 4; and v is an integer from 0 to 2; and each * represents a covalent bond to the rest of the conjugate, or a pharmaceutically acceptable salt thereof.

63. The method of clause 61 or 62, wherein the CA IX ligand is of the formula wherein * represents a covalent bond to the rest of the conjugate, or a pharmaceutically acceptable salt thereof.

64. The method of clause 61 or 62, wherein the conjugate comprises the formula wherein q2 is an integer from 1 to 40, and * represents a covalent bond to the rest of the conjugate, or a pharmaceutically acceptable salt thereof.

65. The method of any one of clauses 61 to 64, wherein the CA IX ligand is of the formula wherein * represents a covalent bond to the rest of the conjugate, or a pharmaceutically acceptable salt thereof.

66. The method of any one of clauses 61 to 64, wherein the conjugate comprises the formula wherein q2 is an integer from 1 to 40, and * represents a covalent bond to the rest of the conjugate, or a pharmaceutically acceptable salt thereof.

67. The method of clause 64 or 66, wherein q2 is 4.

68. The method of clause 64 or 66, wherein q2 is 12.

69. The method of clause 64 or 66, wherein q2 is 36.

70. The method of clause 61 or 62, wherein the conjugate comprises the formula wherein q2 is an integer from 1 to 40, and * represents a covalent bond to the rest of the conjugate, or a pharmaceutically acceptable salt thereof.

71. The method of any one of clauses 61, 62 or 70, wherein the conjugate comprises the formula

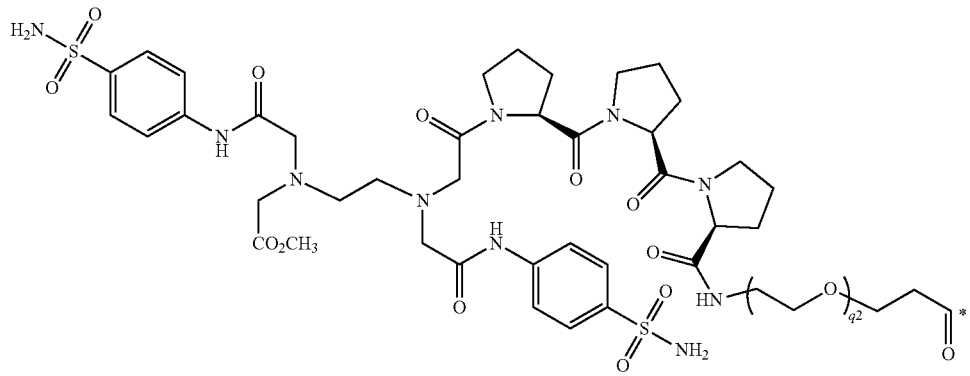

wherein q2 is an integer from 1 to 40, and * represents a covalent bond to the rest of the conjugate, or a pharmaceutically acceptable salt thereof.

72. The method of clause 70 or 71, wherein q2 is 4.
73. The method of clause 70 or 71, wherein q2 is 12.
74. The method of clause 70 or 71, wherein q2 is 36.
75. The method of clause 61 or 62, wherein the CA IX ligand is of the formula

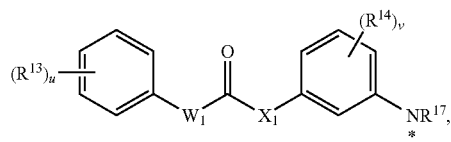

wherein * represents a covalent bond to the rest of the conjugate, or a pharmaceutically acceptable salt thereof.

76. The method of clause 61, 61 or 75, wherein the CA IX ligand is of the formula

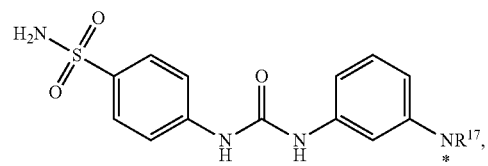

wherein * represents a covalent bond to the rest of the conjugate, or a pharmaceutically acceptable salt thereof.

77. The method of any one of clauses 61, 62 or 75, wherein the conjugate comprises the formula

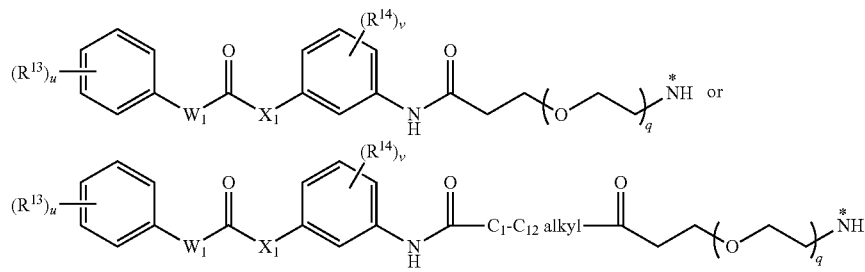

wherein q is an integer from 1 to 40, and * represents a covalent bond to the rest of the conjugate, or a pharmaceutically acceptable salt thereof.

78. The method of any one of clauses 61, 62 or 75 to 77, wherein the conjugate comprises the formula

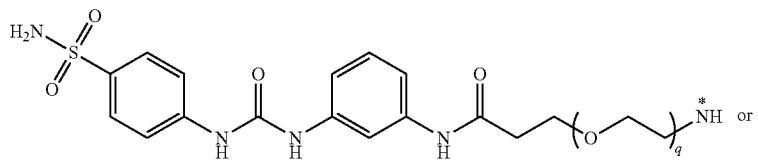

-continued

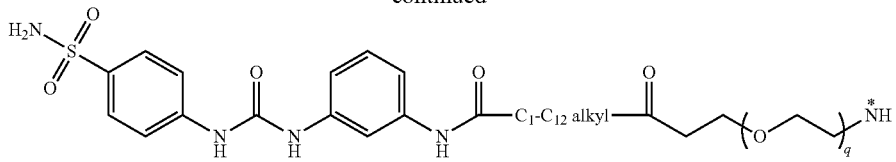

wherein q is an integer from 1 to 40, and * represents a covalent bond to the rest of the conjugate, or a pharmaceutically acceptable salt thereof.

79. The method of any one of clauses 77 or 78, wherein q is 4.

80. The method of any one of clauses 77 or 78, wherein q is 12.

81. The method of any one of clauses 77 or 78, wherein q is 36.

82. The method of any one of clauses 60 to 81, wherein the imaging agent is a SPECT imaging agent, or a pharmaceutically acceptable salt thereof.

83. The method of any one of clauses 60 to 81, wherein the imaging agent is an imaging agent of the formula

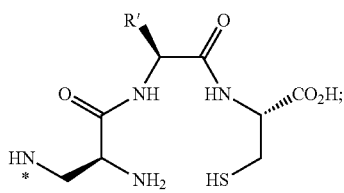

wherein R' is H, or R' is selected from the group consisting of $C_1$-$C_6$ alkyl, amino-$C_1$-$C_6$ alkyl, carboxy-$C_1$-$C_6$ alkyl, hydroxyl-$C_1$-$C_6$ alkyl, $C_1$-$C_6$ heteroalkyl, $C_6$-$C_{10}$ aryl, $C_6$-$C_{10}$ aryl, $C_6$-$C_{10}$ aryl-$C_1$-$C_6$ alkyl alkyl and $C_5$-$C_{10}$ heteroaryl-$C_1$-$C_6$ alkyl; and * represents a covalent bond to the rest of the conjugate, and wherein a radionuclei is bound to the conjugate, or a pharmaceutically acceptable salt thereof.

84. The method of any one of clauses 60 to 83, wherein the imaging agent is an imaging agent of the formula

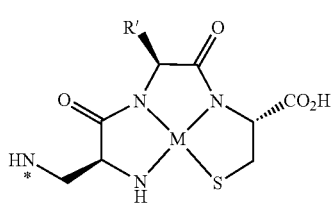

wherein M is a cation of a radionuclide, R' is H, or R' is selected from the group consisting of $C_1$-$C_6$ alkyl, amino-$C_1$-$C_6$ alkyl, carboxy-$C_1$-$C_6$ alkyl, hydroxyl-$C_1$-$C_6$ alkyl, $C_1$-$C_6$ heteroalkyl, $C_6$-$C_{10}$ aryl, $C_6$-$C_{10}$ aryl-$C_1$-$C_6$ alkyl alkyl and $C_5$-$C_{10}$ heteroaryl-$C_1$-$C_6$ alkyl, and * represents a covalent bond to the rest of the conjugate, or a pharmaceutically acceptable salt thereof.

85. The method of any one of clauses 60 to 83, wherein the agent is an imaging agent of the formula

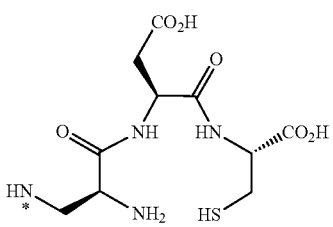 [SMILES: NC[C@H](N)C(=O)N[C@@H](CC(=O)O)C(=O)N[C@@H](CS)C(=O)O]

wherein * represents a covalent bond to the rest of the conjugate, and wherein a radionuclei is bound to the conjugate, or a pharmaceutically acceptable salt thereof.

86. The method of any one of clauses 60 to 85, wherein the agent is an imaging agent of the formula

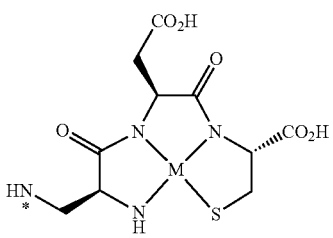

wherein M is a cation of a radionuclide, and * represents a covalent bond to the rest of the conjugate, or a pharmaceutically acceptable salt thereof.

87. The method of any one of clauses 83 to 86, wherein the radionuclei is selected from the group consisting of an isotope of gallium, an isotope of indium, an isotope of copper, an isotope of technetium, and an isotope of rhenium.

88. The method of any one of clauses 83 to 87, wherein the radionuclei is an isotope of technetium.

89. The method of any one of clauses 83 to 88, wherein the radionuclei is $^{99m}$Tc.

90. The method of clause 61, wherein the conjugate is selected from the group consisting of
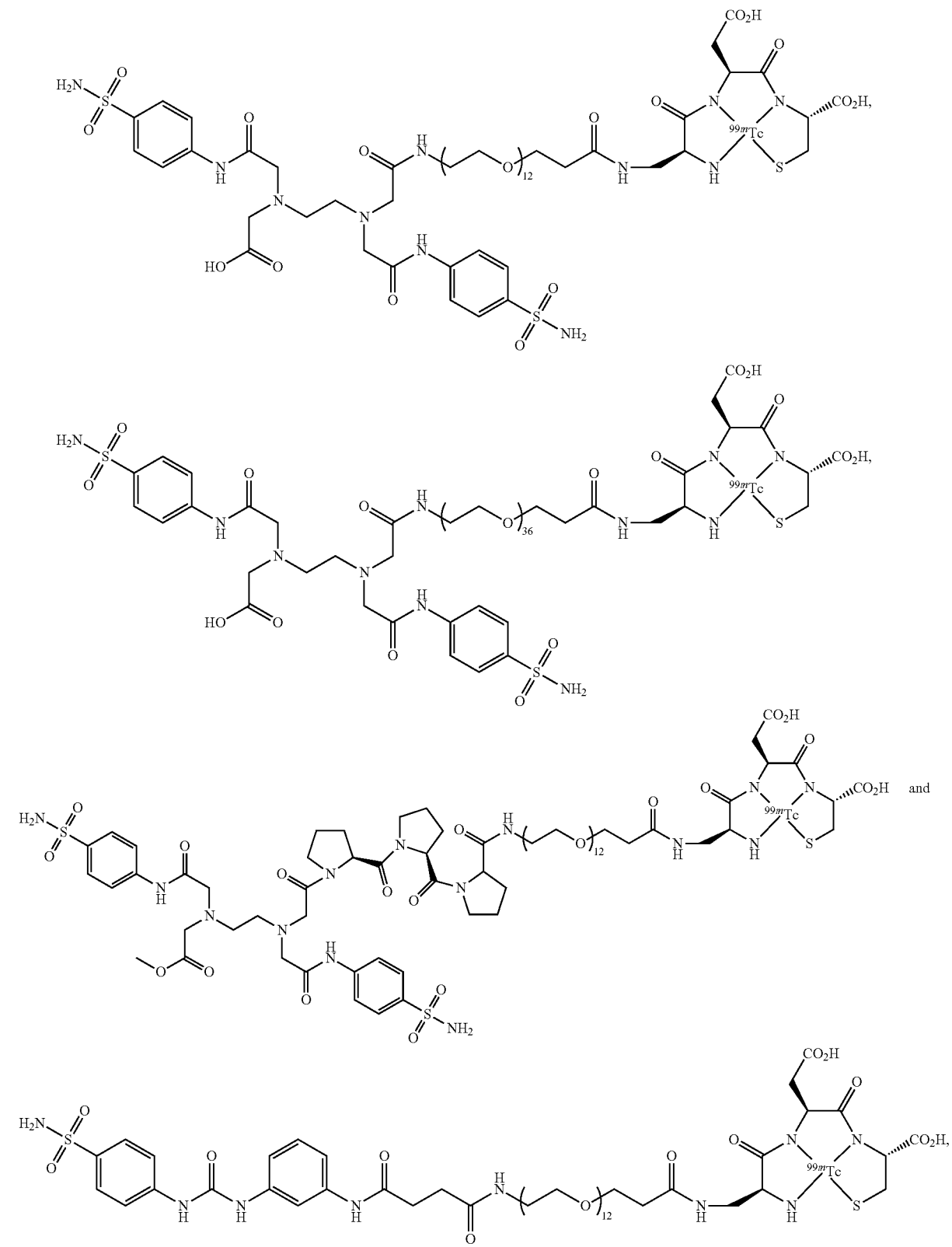
or a pharmaceutically acceptable salt thereof.

91. A composition comprising a conjugate according to any one of clauses 1 to 59, or a pharmaceutically acceptable salt thereof, and optionally at least one pharmaceutically acceptable excipient.

92. A conjugate according to any one of clauses 1 to 46, for use in a method of imaging a population of cells in a subject.

93. The use of clause 92, wherein the method comprises administering to the subject an amount of the conjugate effective for imaging the cells.

94. The use of a conjugate according to any one of clauses 1 to 46, in the preparation of a medicament useful for imaging a population of cells in a subject.

95. The use of clause 94, wherein the method comprises administering to the subject an amount of the conjugate effective for imaging the cells.

96. A conjugate according to any one of clauses 1 to 28 or 47 to 59 for use in a method of treating cancer in a subject.

97. The conjugate of clause 96, wherein the method comprises administering to the subject an amount of the conjugate effective for imaging the cancer.

98. A method of imaging a population of cells in vitro, comprising a. contacting the cells with a conjugate of any one of clauses 1 to 28, 42 or 44 to provide labelled cells, and b. visualizing the labelled cells with a fluorescent light source.

99. A method of treating cancer in a subject, comprising a. administering to the subject an effective amount of a conjugate of any one of clauses 1 to 28 or 47 to 59; or a pharmaceutically acceptable salt thereof.

100. The method of clause 99, further comprising b. identifying a patient for treatment by imaging.

101. The method of clause 100, wherein the imaging comprising a. administering to the patient an effective amount of a conjugate according to any one of clauses 29 to 41, 45 or 46; and b. identifying the patient as having a CA IX expressing cancer.

102. The method of any one of clauses 99 to 101, wherein the cancer is selected from the group consisting of lung, colorectal, gastric, pancreatic, breast, cervical, bladder, ovarian, brain, head & neck, oral and kidney cancer.

BRIEF DESCRIPTION OF THE DRAWINGS

FIG. 3 Binding of Hypoxyfluor and CA IX-targeted rhodamine to HT-29 cells.

FIG. 5 shows in vivo imaging and biodistribution of L2-PEG$_{36}$-EC20 at 4 hours post-injection as compared to control.

FIG. 6 shows in vivo imaging and biodistribution of L2-PEG$_{36}$-EC20 at 4 hours post-injection as compared to control.

FIG. 7 shows in vivo imaging and biodistribution of L2-PEG$_{36}$-EC20 at 4 hours post-injection as compared to control.

FIG. 8 shows in vivo biodistribution of various CA IX conjugates. Mice bearing HT-29 xenograft tumors were administered 10 nmol of $^{99m}$Tc coordinated conjugates L2-PEG$_{12}$-EC20 (FIG. 8A), L2-PEG$_{36}$-EC20 (FIG. 8B), L2-Pro$_3$-PEG12-EC20 (FIG. 8C) and L3-PEG$_{12}$-EC20 (FIG. 8D) via tail vein injection. Additional mice were simultaneously injected with 100 nmol of unlabeled L2 or L3 ligand. Major tissues/organs were removed and the amount of radioactivity was determined. The percentage of injected dose/g of tissue was calculated and plotted. Error bars represent standard deviation.

FIG. 10 shows in vivo efficacy of L2-Tubulysin B. Mice were injected with $10^6$ HT-29 cells. Once tumors reached a volume of ~100 mm$^3$, mice were randomized into various treatment groups (n=3 for each IP group). L2-Tubulysin B (2 µmol/kg) was administered intraperitoneally in the presence or absence of 100-fold excess CA IX ligand L2 every other day for 9 doses. Tumor volume and weight were measured every other day. Error bars represent standard error of the mean.

FIG. 11 shows in vivo efficacy of L2-Tubulysin B. Mice were injected with $10^6$ HT-29 cells. Once tumors reached a volume of ~100 mm$^3$, mice were randomized into various treatment groups (n=5 for each IV group). CA IX-Tubulysin B (2 mol/kg) was administered via tail vein injection in the presence or absence of 100-fold excess CA IX ligand every other day for 9 doses. Tumor volume and weight were measured every other day. Error bars represent standard error of the mean.

DEFINITIONS

Figure 1:
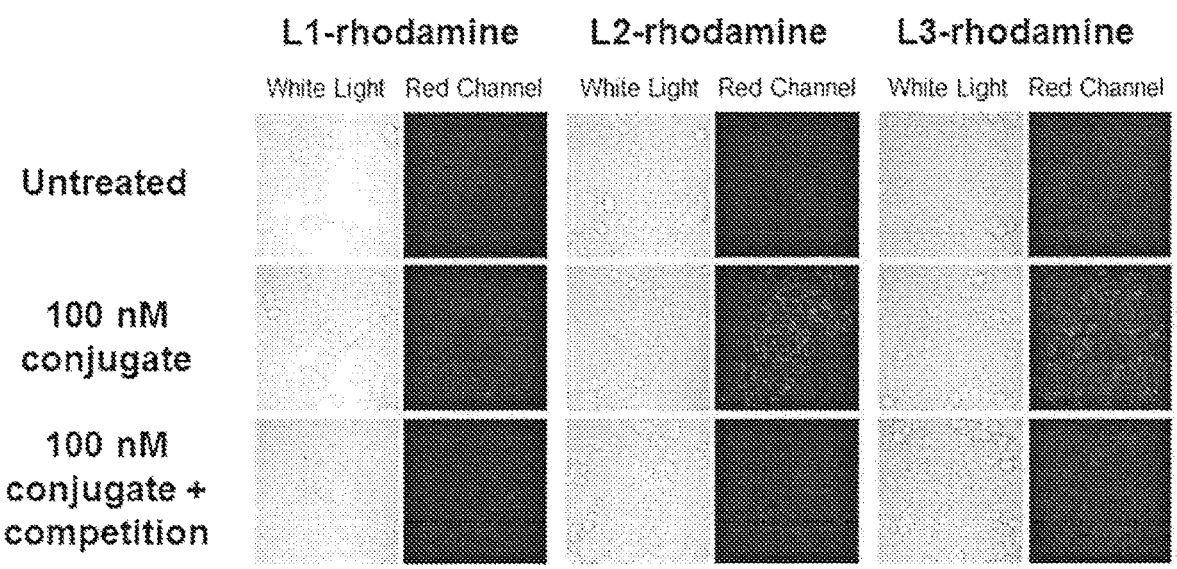
FIG. 1 shows the in vitro binding of rhodamine-labeled CA IX conjugates to HT-29 cells. Fluorescent conjugates were incubated with HT-29 cells in the presence or absence of 100-fold excess unlabeled ligand. After washing, white light and fluorescent microscopy were used to visualize binding.

As used herein, the term "alkyl" includes a chain of carbon atoms, which is optionally branched and contains from 1 to 20 carbon atoms. It is to be further understood that in certain embodiments, alkyl may be advantageously of limited length, including $C_1$-$C_{12}$, $C_1$-$C_{10}$, $C_1$-$C_9$, $C_1$-$C_8$, $C_1$-$C_7$, $C_1$-$C_6$, and $C_1$-$C_4$, Illustratively, such particularly limited length alkyl groups, including $C_1$-$C_8$, $C_1$-$C_7$, $C_1$-$C_6$, and $C_1$-$C_4$, and the like may be referred to as "lower alkyl." Illustrative alkyl groups include, but are not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl, and the like. Alkyl may be substituted or unsubstituted. Typical substituent groups include cycloalkyl, aryl, heteroaryl, heteroalicyclic, hydroxy, alkoxy, aryloxy, mercapto, alkylthio, arylthio, cyano, halo, carbonyl, oxo, (=O), thiocarbonyl, O-carbamyl, N-carbamyl, O-thiocarbamyl, N-thiocarbamyl, C-amido, N-amido, C-carboxy, O-carboxy, nitro, and amino, or as described in the various embodiments provided herein. It will be understood that "alkyl" may be combined with other groups, such as those provided above, to form a functionalized alkyl. By way of example, the combination of an "alkyl" group, as described herein, with a "carboxy" group may be referred to as a "carboxyalkyl" group. Other non-limiting examples include hydroxyalkyl, aminoalkyl, and the like.

As used herein, the term "alkenyl" includes a chain of carbon atoms, which is optionally branched, and contains from 2 to 20 carbon atoms, and also includes at least one carbon-carbon double bond (i.e. C=C). It will be understood that in certain embodiments, alkenyl may be advantageously of limited length, including $C_2$-$C_{12}$, $C_2$-$C_9$, $C_2$-$C_8$, $C_2$-$C_7$, $C_2$-$C_6$, and $C_2$-$C_4$. Illustratively, such particularly limited length alkenyl groups, including $C_2$-$C_8$, $C_2$-$C_7$, $C_2$-$C_6$, and $C_2$-$C_4$ may be referred to as lower alkenyl. Alkenyl may be unsubstituted, or substituted as described for alkyl or as described in the various embodiments provided herein. Illustrative alkenyl groups include, but are not limited to, ethenyl, 1-propenyl, 2-propenyl, 1-, 2-, or 3-butenyl, and the like.

As used herein, the term "alkynyl" includes a chain of carbon atoms, which is optionally branched, and contains from 2 to 20 carbon atoms, and also includes at least one carbon-carbon triple bond (i.e. C≡C). It will be understood that in certain embodiments alkynyl may each be advantageously of limited length, including $C_2$-$C_{12}$, $C_2$-$C_9$, $C_2$-$C_8$, $C_2$-$C_7$, $C_2$-$C_6$, and $C_2$-$C_4$. Illustratively, such particularly limited length alkynyl groups, including $C_2$-$C_8$, $C_2$-$C_7$, $C_2$-$C_6$, and $C_2$-$C_4$ may be referred to as lower alkynyl. Alkenyl may be unsubstituted, or substituted as described for alkyl or as described in the various embodiments provided herein. Illustrative alkenyl groups include, but are not limited to, ethynyl, 1-propynyl, 2-propynyl, 1-, 2-, or 3-butynyl, and the like.

As used herein, the term "aryl" refers to an all-carbon monocyclic or fused-ring polycyclic groups of 6 to 12 carbon atoms having a completely conjugated pi-electron system. It will be understood that in certain embodiments, aryl may be advantageously of limited size such as $C_6$-$C_{10}$ aryl. Illustrative aryl groups include, but are not limited to, phenyl, naphthalenyl and anthracenyl. The aryl group may be unsubstituted, or substituted as described for alkyl or as described in the various embodiments provided herein.

As used herein, the term "cycloalkyl" refers to a 3 to 15 member all-carbon monocyclic ring, an all-carbon 5-member/6-member or 6-member/6-member fused bicyclic ring, or a multicyclic fused ring (a "fused" ring system means that each ring in the system shares an adjacent pair of carbon atoms with each other ring in the system) group where one or more of the rings may contain one or more double bonds but the cycloalkyl does not contain a completely conjugated pi-electron system. It will be understood that in certain embodiments, cycloalkyl may be advantageously of limited size such as $C_3$-$C_{13}$, $C_3$-$C_6$, $C_3$-$C_6$ and $C_4$-$C_6$. Cycloalkyl may be unsubstituted, or substituted as described for alkyl or as described in the various embodiments provided herein. Illustrative cycloalkyl groups include, but are not limited to, cyclopropyl, cyclobutyl, cyclopentyl, cyclopentenyl, cyclopentadienyl, cyclohexyl, cyclohexenyl, cycloheptyl, adamantyl, norbornyl, norbornenyl, 9H-fluoren-9-yl, and the like.

As used herein, the term "heterocycloalkyl" refers to a monocyclic or fused ring group having in the ring(s) from 3 to 12 ring atoms, in which at least one ring atom is a heteroatom, such as nitrogen, oxygen or sulfur, the remaining ring atoms being carbon atoms. Heterocycloalkyl may optionally contain 1, 2, 3 or 4 heteroatoms. Heterocycloalkyl may also have one of more double bonds, including double bonds to nitrogen (e.g. C=N or N=N) but does not contain a completely conjugated pi-electron system. It will be understood that in certain embodiments, heterocycloalkyl may be advantageously of limited size such as 3- to 7-membered heterocycloalkyl, 5- to 7-membered heterocycloalkyl, and the like. Heterocycloalkyl may be unsubstituted, or substituted as described for alkyl or as described in the various embodiments provided herein. Illustrative heterocycloalkyl groups include, but are not limited to, oxiranyl, thianaryl, azetidinyl, oxetanyl, tetrahydrofuranyl, pyrrolidinyl, tetrahydropyranyl, piperidinyl, 1,4-dioxanyl, morpholinyl, 1,4-dithianyl, piperazinyl, oxepanyl, 3,4-dihydro-2H-pyranyl, 5,6-dihydro-2H-pyranyl, 2H-pyranyl, 1, 2, 3, 4-tetrahydropyridinyl, and the like.

As used herein, the term "heteroaryl" refers to a monocyclic or fused ring group of 5 to 12 ring atoms containing one, two, three or four ring heteroatoms selected from nitrogen, oxygen and sulfur, the remaining ring atoms being carbon atoms, and also having a completely conjugated pi-electron system. It will be understood that in certain embodiments, heteroaryl may be advantageously of limited size such as 3- to 9-membered heteroaryl, 3- to 7-membered heteroaryl, 5- to 7-membered heteroaryl, 5- to 9-membered heteroaryl, and the like. Heteroaryl may be unsubstituted, or substituted as described for alkyl or as described in the various embodiments provided herein. Illustrative heteroaryl groups include, but are not limited to, pyrrolyl, furanyl, thiophenyl, imidazolyl, oxazolyl, thiazolyl, pyrazolyl, pyridinyl, pyrimidinyl, quinolinyl, isoquinolinyl, purinyl, tetrazolyl, triazinyl, pyrazinyl, tetrazinyl, quinazolinyl, quinoxalinyl, thienyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, indolyl, and carbazoloyl, and the like.

As used herein, "hydroxy" or "hydroxyl" refers to an —OH group.

As used herein, "alkoxy" refers to both an —O-(alkyl) or an —O-(unsubstituted cycloalkyl) group. Representative examples include, but are not limited to, methoxy, ethoxy, propoxy, butoxy, cyclopropyloxy, cyclobutyloxy, cyclopentyloxy, cyclohexyloxy, and the like.

As used herein, "aryloxy" refers to an —O-aryl or an —O-heteroaryl group. Representative examples include, but are not limited to, phenoxy, pyridinyloxy, furanyloxy, thienyloxy, pyrimidinyloxy, pyrazinyloxy, and the like, and the like.

As used herein, "mercapto" refers to an —SH group.

As used herein, "alkylthio" refers to an —S-(alkyl) or an —S-(unsubstituted cycloalkyl) group. Representative examples include, but are not limited to, methylthio, ethylthio, propylthio, butylthio, cyclopropylthio, cyclobutylthio, cyclopentylthio, cyclohexylthio, and the like.

As used herein, "arylthio" refers to an —S-aryl or an —S-heteroaryl group. Representative examples include, but are not limited to, phenylthio, pyridinylthio, furanylthio, thienylthio, pyrimidinylthio, and the like.

As used herein, "halo" or "halogen" refers to fluorine, chlorine, bromine or iodine.

As used herein, "trihalomethyl" refers to a methyl group having three halo substituents, such as a trifluoromethyl group.

As used herein, "cyano" refers to a —CN group.

As used herein, "sulfinyl" refers to a —S(O)R" group, where R" is any R group as described in the various embodiments provided herein, or R" may be a hydroxyl group.

As used herein, "sulfonyl" refers to a —S(O)$_2$R" group, where R" is any R group as described in the various embodiments provided herein, or R" may be a hydroxyl group.

As used herein, "S-sulfonamido" refers to a —S(O)$_2$NR"R" group, where R" is any R group as described in the various embodiments provided herein.

As used herein, "N-sulfonamido" refers to a —NR"S(O)$_2$R" group, where R" is any R group as described in the various embodiments provided herein.

As used herein, "O-carbamyl" refers to a —OC(O)NR"R" group, where R" is any R group as described in the various embodiments provided herein.

As used herein, "N-carbamyl" refers to an R"OC(O)NR"— group, where R" is any R group as described in the various embodiments provided herein.

As used herein, "O-thiocarbamyl" refers to a —OC(S)NR"R" group, where R" is any R group as described in the various embodiments provided herein.

As used herein, "N-thiocarbamyl" refers to a R"OC(S)NR" group, where R" is any R group as described in the various embodiments provided herein.

As used herein, "amino" refers to an —NR"R" group, where R" is any R group as described in the various embodiments provided herein.

As used herein, "C-amido" refers to a —C(O)NR"R" group, where R" is any R group as described in the various embodiments provided herein.

As used herein, "N-amido" refers to a R"C(O)NR"— group, where R" is any R group as described in the various embodiments provided herein.

As used herein, "nitro" refers to a NO$_2$ group.

As used herein, "bond" refers to a covalent bond.

As used herein, "optional" or "optionally" means that the subsequently described event or circumstance may but need not occur, and that the description includes instances where the event or circumstance occurs and instances in which it does not. For example, "heterocycle group optionally substituted with an alkyl group" means that the alkyl may but need not be present, and the description includes situations where the heterocycle group is substituted with an alkyl group and situations where the heterocycle group is not substituted with the alkyl group.

As used herein, "independently" means that the subsequently described event or circumstance is to be read on its own relative to other similar events or circumstances. For example, in a circumstance where several equivalent hydrogen groups are optionally substituted by another group described in the circumstance, the use of "independently optionally" means that each instance of a hydrogen atom on the group may be substituted by another group, where the groups replacing each of the hydrogen atoms may be the same or different. Or for example, where multiple groups exist all of which can be selected from a set of possibilities, the use of "independently" means that each of the groups can be selected from the set of possibilities separate from any other group, and the groups selected in the circumstance may be the same or different.

As used herein, "amino acid" (a.k.a. "AA") means any molecule that includes an alpha-carbon atom covalently bonded to an amino group and an acid group. The acid group may include a carboxyl group. "Amino acid" may include molecules having one of the formulas:

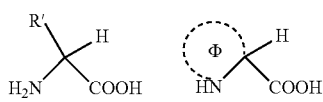

wherein R' is a side group and 1 includes at least 3 carbon atoms. "Amino acid" includes stereoisomers such as the D-amino acid and L-amino acid forms. Illustrative amino acid groups include, but are not limited to, the twenty endogenous human amino acids and their derivatives, such as lysine (Lys), asparagine (Asn), threonine (Thr), serine (Ser), isoleucine (Ile), methionine (Met), proline (Pro), histidine (His), glutamine (Gln), arginine (Arg), glycine (Gly), aspartic acid (Asp), glutamic acid (Glu), alanine (Ala), valine (Val), phenylalanine (Phe), leucine (Leu), tyrosine (Tyr), cysteine (Cys), tryptophan (Trp), phosphoserine (PSER), sulfo-cysteine, arginosuccinic acid (ASA), hydroxyproline, phosphoethanolamine (PEA), sarcosine (SARC), taurine (TAU), carnosine (CARN), citrulline (CIT), anserine (ANS), 1,3-methyl-histidine (ME-HIS), alpha-amino-adipic acid (AAA), beta-alanine (BALA), ethanolamine (ETN), gamma-amino-butyric acid (GABA), beta-amino-isobutyric acid (BAIA), alpha-amino-butyric acid (BABA), L-allo-cystathionine (cystathionine-A; CYSTA-A), L-cystathionine (cystathionine-B; CYSTA-B), cystine, allo-isoleucine (ALLO-ILE), DL-hydroxylysine (hydroxylysine (I)), DL-allo-hydroxylysine (hydroxylysine (2)), ornithine (ORN), homocystine (HCY), and derivatives thereof. In connection with the embodiments described herein, amino acids can be covalently attached to other portions of the conjugates described herein through their alpha-amino and carboxy functional groups (i.e. in a peptide bond configuration), or through their side chain functional groups (such as the side chain carboxy group in glutamic acid) and either their alpha-amino or carboxy functional groups. It will be understood that amino acids, when used in connection with the conjugates described herein, may exist as zwitterions in a conjugate in which they are incorporated.

As used herein, "prodrug" refers to a compound that can be administered to a subject in a pharmacologically inactive form which then can be converted to a pharmacologically active form through a normal metabolic process, such as hydrolysis of an oxazolidine. It will be understood that the metabolic processes through which a prodrug can be converted to an active drug include, but are not limited to, one or more spontaneous chemical reaction(s), enzyme-catalyzed chemical reaction(s), and/or other metabolic chemical reaction(s), or a combination thereof. It will be appreciated that understood that a variety of metabolic processes are known in the art, and the metabolic processes through which the prodrugs described herein are converted to active drugs are non-limiting. A prodrug can be a precursor chemical compound of a drug that has a therapeutic effect on a subject.

As used herein, the term "therapeutically effective amount" refers to an amount of a drug or pharmaceutical agent that elicits the biological or medicinal response in a subject (i.e. a tissue system, animal or human) that is being sought by a researcher, veterinarian, medical doctor or other clinician, which includes, but is not limited to, alleviation of the symptoms of the disease or disorder being treated. In one aspect, the therapeutically effective amount is that amount of an active which may treat or alleviate the disease or symptoms of the disease at a reasonable benefit/risk ratio applicable to any medical treatment. In another aspect, the therapeutically effective amount is that amount of an inactive prodrug which when converted through normal metabolic processes to produce an amount of active drug capable of eliciting the biological or medicinal response in a subject that is being sought.

It is also appreciated that the dose, whether referring to monotherapy or combination therapy, is advantageously selected with reference to any toxicity, or other undesirable side effect, that might occur during administration of one or more of the conjugates described herein. Further, it is appreciated that the co-therapies described herein may allow for the administration of lower doses of conjugates that show such toxicity, or other undesirable side effect, where those lower doses are below thresholds of toxicity or lower in the therapeutic window than would otherwise be administered in the absence of a cotherapy.

As used herein, "administering" includes all means of introducing the conjugates and compositions described herein to the host animal, including, but are not limited to, oral (po), intravenous (iv), intramuscular (im), subcutaneous (sc), transdermal, inhalation, buccal, ocular, sublingual, vaginal, rectal, and the like. The conjugates and compositions described herein may be administered in unit dosage forms and/or formulations containing conventional nontoxic pharmaceutically-acceptable carriers, adjuvants, and/or vehicles.

As used herein "pharmaceutical composition" or "composition" refers to a mixture of one or more of the conjugates described herein, or pharmaceutically acceptable salts, solvates, hydrates thereof, with other chemical components, such as pharmaceutically acceptable excipients. The purpose of a pharmaceutical composition is to facilitate administration of a conjugate to a subject. Pharmaceutical compositions suitable for the delivery of conjugates described and methods for their preparation will be readily apparent to those skilled in the art. Such compositions and methods for their preparation may be found, for example, in 'Remington's Pharmaceutical Sciences', 19th Edition (Mack Publishing Company, 1995).

As used herein and in the appended claims, the singular forms "a," "an," and "the" include plural reference unless the context clearly indicates otherwise.

Unless defined otherwise, all technical and scientific terms used herein have the same meaning as commonly understood to one of ordinary skill in the art to which this invention belongs. Although any methods, devices, and materials similar or equivalent to those described herein can be used in the practice or testing of the invention, the preferred methods, devices and materials are now described.

DETAILED DESCRIPTION

In accordance with Applicants' disclosure described herein, the embodiments of the numbered clauses provided in the summary above, or any combination thereof, are contemplated for combination with any of the embodiments described in the Detailed Description section of this patent application.

In each of the foregoing and each of the following embodiments, it is to be understood that the formulae include and represent not only all pharmaceutically acceptable salts of the conjugates, but also include any and all hydrates and/or solvates of the conjugate formulae. It is appreciated that certain functional groups, such as the hydroxy, amino, and like groups form complexes and/or coordination conjugates with water and/or various solvents, in the various physical forms of the conjugates. Accordingly, the above formulae are to be understood to include and represent those various hydrates and/or solvates. It is also to be understood that the non-hydrates and/or non-solvates of the conjugate formulae are described by such formula, as well as the hydrates and/or solvates of the conjugate formulae.

In some embodiments, the disclosure provides a conjugate of the formula B-L-A, wherein B is a binding ligand of carbonic anhydrase IX, L is an optional linker, and A is a therapeutic agent and an imaging agent.

It will be appreciated that CA IX ligands useful in connection with the present disclosure are not particularly limited by structure. Useful CA IX inhibitors can be any drug or compound that shows binding affinity for CA IX, such as a CA IX inhibitor, CA IX agonist, or CA IX antagonist. In some aspects of these embodiments, the CA IX ligand is an aryl sulfonamide containing compound. In some aspects of these embodiments, the CA IX ligand is of the formula

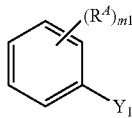

wherein each $R^A$ is independently selected from the group consisting of H, halogen, —$OR^{1'}$, —$OC(O)R^{1'}$, —$OC(O)N^{1'}R^{2'}$, —$OS(O)R^{1'}$, —$OS(O)_2R^{1'}$, —$SR^{1'}$, —$S(O)R^{1'}$, —$S(O)_2R^{1'}$, —$S(O)NR^{1'}R^{2'}$, —$S(O)_2NR^{1'}R^{2'}$, —$OS(O)N R^{1'}R^{2'}$, —$OS(O)_2NR^{1'}R^{2'}$, —$NR^{1'}R^{2'}$, —$NR^{1'}C(O)R^{1'}$, —$NR^{1'}C(O)OR^{2'}$, —$NR^{1'}C(O)NR^{1'}R^{2'}$, —$NR^{1'}S(O)R^{2'}$, —$NR^{1'}S(O)_2R^{2'}$, —$NR^{1'}S(O)N R^{1'}R^{2'}$, —$NR^{1'}S(O)_2NR^{1'}R^{2'}$, —$C(O)R^{1'}$, —$C(O)OR^{1'}$, and —$C(O)NR^{1'}R^{2'}$;

$Y_1$ is —$OR^B$, —$SR^B$, —$NR^BR^{B'}$, —$S(O)_2R^B$, —$NR^BC(O)R^W$ or —$NR^BC(O)NR^BR^{B'}$;

each $R^B$ and $R^{B'}$ is independently H, $C_1$-$C_{10}$ alkyl, $C_2$-$C_{10}$ alkenyl or phenyl; wherein each hydrogen atom in $C_1$-$C_{10}$ alkyl, $C_2$-$C_{10}$ alkenyl, and phenyl is optionally substituted with —CN, $C_1$-$C_6$ alkyl-(5- to 9-membered heteroaryl), —$NR^3R^4$, —$NR^{3'}(CH_2)_{m2}NR^{3'}R^{4'}$ or —$C_6H_4OR^3$;

each $R^{3'}$ and $R^{4'}$ is independently H, —$CH_2C(O)^*$, —$CH_2C(O)OR^{5'}$, —$CH_2C(O)NR^{5'}R^{6'}$, or a bond to the rest of the conjugate;

each $R^{5'}$ and $R^{6'}$ is independently H, $C_1$-$C_8$ alkyl, or phenyl, wherein each hydrogen atom in wherein each hydrogen atom in $C_1$-$C_{10}$ alkyl, $C_2$-$C_{10}$ alkenyl, and phenyl is optionally substituted with $C_1$-$C_6$ alkyl-(phenyl), —$OR^{1'}$, —$OC(O)R^{1'}$, —$OC(O)NR^{1'}R^{2'}$, —$OS(O)R^{1'}$, —$OS(O)_2R^{1'}$, —$SR^{1'}$, —$S(O)R^{1'}$, —$S(O)_2R^{1'}$, —$S(O)NR^{1'}R^{2'}$, —$S(O)_2NR^{1'}R^{2'}$, —$OS(O)NR^{1'}R^{2'}$, —$OS(O)_2NR^{1'}R^{2'}$, —$NR^{1'}R^{2'}$, —$NR^{1'}C(O)R^{1'}$, —$NR^{1'}C(O)OR^{2'}$, —$NR^{1'}C(O)NR^{1'}R^{2'}$, —$NR^{1'}S(O)R^{2'}$, —$NR^{1'}S(O)_2R^{2'}$, —$NR^{1'}S(O)N R^{1'}R^{2'}$, —$NR^{1'}S(O)_2NR^{1'}R^{2'}$, —$C(O)R^{1'}$, —$C(O)OR^{1'}$, and —$C(O)NR^{1'}R^{2'}$;

each $R^{1'}$ and $R^{2'}$ is independently selected from the group consisting of H, $C_1$-$C_6$ alkyl, $C_2$-$C_6$ alkenyl, $C_2$-$C_6$ alkynyl, and $C_3$-$C_9$ cycloalkyl;

m1 is 1, 2, 3, 4 or 5; and

* represents a covalent bond to the rest of the conjugate.

In some embodiments, at least one $R^A$ is a —$S(O)_2NR^{1'}R^{2'}$. In some embodiments, m1 is 1, and $R^A$ is a —$S(O)_2NR^{1'}R^{2'}$. In some embodiments, the 5- to 7-membered heteroaryl having from 1 to 3 heteroatoms is a thiadiazolyl ring.

In some embodiments, the CA IX ligand is of the formula

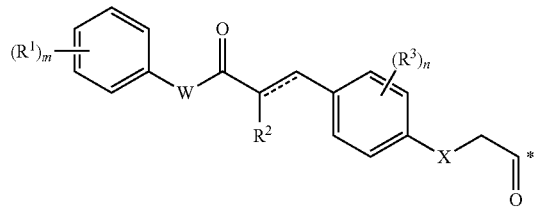

wherein $R^1$, $R^2$, $R^3$, W, X, m, n and * are as defined herein. In some aspects of these embodiments, m is 1. In some aspects of these embodiments, n is 0. In some aspects of these embodiments, $R^1$ is —$S(O)_2NR^4R^5$. In some aspects of these embodiments, $R^1$ is —$S(O)_2NR^4R^5$ in the para-position of the ring to which $R^1$ is attached. In some aspects of these embodiments, $R^4$ and $R^5$ are H. In some aspects of these embodiments, $R^2$ is —CN. In some aspects of these embodiments, ⚡ is a pi-bond. In some aspects of these embodiments, W is —$NR^{4'}$—. In some aspects of these embodiments, X is —O—. In some aspects of these embodiments, $R^{4'}$ is H or —$CH_3$. In some aspects of these embodiments, the CA IX ligand is of the formula

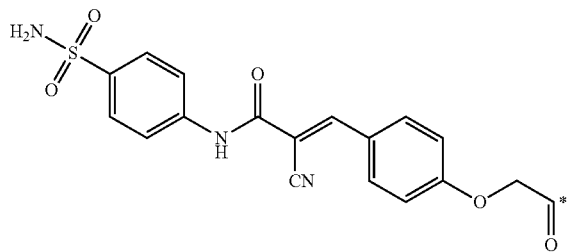 [SMILES: N#C/C(=C\c1ccc(OCC=O)cc1)C(=O)Nc1ccc(S(N)(=O)=O)cc1]

wherein * is as defined herein.

In some embodiments, the CA IX ligand is of the formula

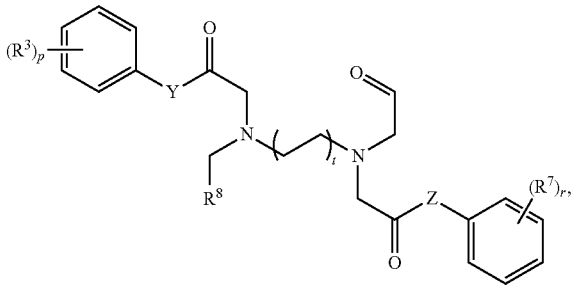

wherein $R^6$, $R^7$, $R^8$, Y, Z, p, r, t and * are as defined herein. In some aspects of these embodiments, p is 1. In some aspects of these embodiments, r is 1. In some aspects of these embodiments, t is 1. In some aspects of these embodiments, $R^6$ is —$S(O)_2NR^9R^{10}$. In some aspects of these embodiments, $R^6$ is —$S(O)_2NR^9R^{10}$ in the para-position of the ring to which $R^6$ is attached. In some aspects of these embodiments, $R^7$ is —$S(O)_2NR^9R^{10}$. In some aspects of these embodiments, $R^7$ is —$S(O)_2NR^9R^{10}$ in the para-position of the ring to which $R^7$ is attached. In some aspects of these embodiments, $R^9$ and $R^{10}$ are H. In some aspects of these embodiments, $R^8$ is —$C(O)OR^{11}$. In some aspects of these embodiments, $R^{11}$ is H or —$CH_3$. In some aspects of these embodiments, Y is —$NR^{9'}$—. In some aspects of these embodiments, Z is —NR$^{10'}$—. In some aspects of these embodiments, R$^{9'}$ is H or —CH$_3$. In some aspects of these embodiments, R$^{10'}$ is H or —CH$_3$. In some aspects of these embodiments, the CA IX ligand is of the formula

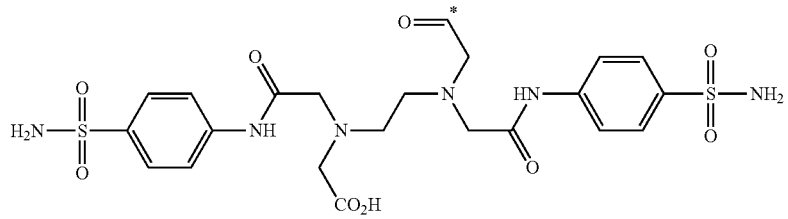 [SMILES: NS(=O)(=O)c1ccc(NC(=O)CN(CC=O)CCN(CC(=O)O)CC(=O)Nc2ccc(S(N)(=O)=O)cc2)cc1]

wherein * is as defined herein.

In some embodiments, the CA IX ligand is of the formula

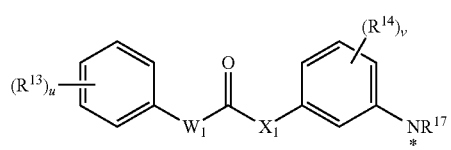

wherein R$^6$, R$^7$, R$^8$, Y, Z, p, r, t and * are as defined herein. In some aspects of these embodiments, u is 1. In some aspects of these embodiments, v is 0. In some aspects of these embodiments, R$^{13}$ is —S(O)$_2$NR$^{15}$R$^{16}$. In some aspects of these embodiments, R$^{13}$ is —S(O)$_2$NR$^{15}$R$^{16}$ in the para-position of the ring to which R$^{13}$ is attached. In some aspects of these embodiments, R$^{15}$ and R$^{16}$ are H. In some aspects of these embodiments, R$^{17}$ is —H. In some aspects of these embodiments, W$_1$ is —NR$^{15'}$—. In some aspects of these embodiments, X$_1$ is —NR$^{16'}$—. In some aspects of these embodiments, R$^{15'}$ is H or —CH$_3$. In some aspects of these embodiments, R$^{16'}$ is H or —CH$_3$. In some aspects of these embodiments, the CA IX ligand is of the formula

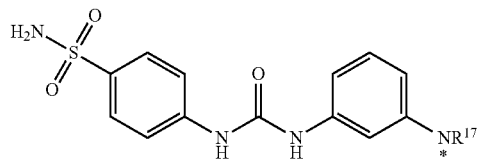

wherein * is as defined herein.

It will be appreciated that linkers useful in connection with the present disclosure are not particularly limited by structure. The linker can be any linker of from 2 to 100 atoms in length and composed of elements including C, N, O and S that covalently attaches a CA IX ligand to an agent. In some embodiments, the linker comprises simple groups, such as alkyl chain portions, ether portions (e.g. PEG), long chain amine portions, amino acid chain portions, a hydrazine portion, and the like, and combinations thereof. In some embodiments, linkers useful in connection with the present disclosure comprise at least one portion selected from the group consisting of —C(O)(CH$_2$)$_{2-10}$NH—, —C(O)(CH$_2$)$_{2-10}$C$_6$H$_4$O—, —C(O)(C$_1$-C$_{12}$ alkyl)C(O)—, —NH—C$_1$-C$_{12}$ alkyl-NH—, —N(C$_1$-C$_6$ alkyl)-C$_1$-C$_{12}$ alkyl-N(C$_1$-C$_6$ alkyl)-, —C(O)CH$_2$CH$_2$(OCH$_2$CH$_2$)$_q$NH—, —C(O)CH$_2$CH$_2$(OCH$_2$CH$_2$)$_{q1}$N(C$_1$-C$_6$ alkyl)-, —NH(CH$_2$CH$_2$O)$_{q2}$CH$_2$CH$_2$C(O)—, and —N(C$_1$-C$_6$ alkyl)(CH$_2$CH$_2$O)$_{q3}$CH$_2$CH$_2$C(O)—; wherein each of q, q1, q2 and q3 is an integer from 1 to 40. In some embodiments, the linker can comprise a chain of amino acids. In some embodiments, the linker can comprise a dipeptide or a tripeptide.

In some embodiments, the linker comprises a releasable linker where the term "releasable linker" refers to a linker that includes at least one bond that can be broken under physiological conditions, such as a pH-labile, acid-labile, base-labile, oxidatively labile, metabolically labile, biochemically labile, or enzyme-labile bond. It is appreciated that such physiological conditions resulting in bond breaking do not necessarily include a biological or metabolic process, and instead may include a standard chemical reaction, such as a hydrolysis reaction, for example, at physiological pH, or as a result of compartmentalization into a cellular organelle such as an endosome having a lower pH than cytosolic pH. In some embodiments, the releasable linker comprises a disulfide bond. In some embodiments, the releasable linker comprises a portion having the formula

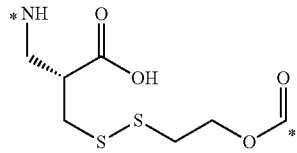 [SMILES: NC[C@@H](CSSCCOC=O)C(=O)O]

wherein each * represents a covalent bond to the rest of the conjugate.

The agent used in connection with any of the conjugates described herein can be any molecule capable of modulating or otherwise modifying cell function, including pharmaceutically active compounds (e.g. a therapeutic agent), or any molecule capable of providing a measurable signal for imaging or visualized cells or tissues (e.g. an imaging agent).

Suitable molecules useful as therapeutic agents include, but are not limited to peptides, oligopeptides, retro-inverso oligopeptides, proteins, protein analogs in which at least one non-peptide linkage replaces a peptide linkage, apoproteins, glycoproteins, enzymes, coenzymes, enzyme inhibitors, amino acids and their derivatives, receptors and other membrane proteins; antigens and antibodies thereto; haptens and antibodies thereto; hormones, lipids, phospholipids, liposomes; toxins; antibiotics; analgesics; bronchodilators; beta-blockers; antimicrobial agents; antihypertensive agents; cardiovascular agents including antiarrhythmics, cardiac glycosides, antianginals and vasodilators; central nervous system agents including stimulants, psychotropics, antimanics, and depressants; antiviral agents; antihistamines; cancer drugs including chemotherapeutic agents; tranquilizers;

anti-depressants; H-2 antagonists; anticonvulsants; antinauseants; prostaglandins and prostaglandin analogs; muscle relaxants; anti-inflammatory substances; stimulants; decongestants; antiemetics; diuretics; antispasmodics; antiasthmatics; anti-Parkinson agents; expectorants; cough suppressants; mucolytics; and mineral and nutritional additives.

In some embodiments, the therapeutic agent can be a tubulysin. Natural tubulysins are generally linear tetrapeptides consisting of N-methyl pipecolic acid (Mep), isoleucine (Ile), an unnatural aminoacid called tubuvaline (Tuv), and either an unnatural aminoacid called tubutyrosine (Tut, an analog of tyrosine) or an unnatural aminoacid called tubuphenylalanine (Tup, an analog of phenylalanine).

In some embodiments, the therapeutic agent is a tetrapeptide of the formula

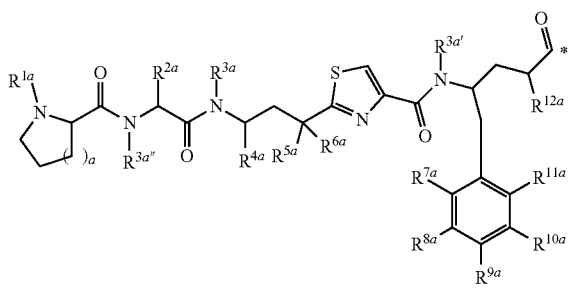

wherein $R^{1a}$, $R^{3a}$, $R^{3a'}$ and $R^{3a''}$ are each independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{13a}$, —OC(O)$R^{13a}$, —OC(O)$NR^{13a}R^{13a'}$, —OS(O)$R^{13a}$, —OS(O)$_2$$R^{13a}$, —$SR^{13a}$, —SC(O)$R^{13a}$, —S(O)$R^{13a}$, —S(O)$_2R^{13a}$, —S(O)$_2OR^{13a}$, —S(O)$NR^{13a}R^{13a'}$, —S(O)$_2NR^{13a}R^{13a'}$, —OS(O)$NR^{13a}R^{13a'}$, OS(O)$_2NR^{13a}R^{13a'}$, —$NR^{13a}$C(O) $R^{14a'}$, —$NR^{13a}$C(O)O$R^{14a}$, —$NR^{13a}$C(O)N$R^{14a}R^{14a'}$; —$NR^{13a}$S(O)$R^{14a}$, —$NR^{13a}$S(O)$_2R^{14a}$, —$NR^{13a}$S(O) $NR^{13a}R^{14a'}$, —$NR^{13a}$S(O)$_2NR^{14a}R^{14a'}$, —P(O)(O$R^{13a}$)$_2$, —C(O)$R^{13a}$, —C(O)O$R^{13a}$ or —C(O)N$R^{13a}R^{13a'}$;

$R^{2a}$, $R^{4a}$ and $R^{12a}$ are each independently selected from the group consisting of H, $C_1$-$C_6$ alkyl, $C_2$-$C_6$ alkenyl, $C_2$-$C_6$ alkynyl;

$R^{5a}$ and $R^{6a}$ are each independently selected from the group consisting of H, halogen, $C_1$-$C_6$ alkyl, $C_2$-$C_6$ alkenyl, $C_2$-$C_6$ alkynyl, —$OR^{15a}$, —$SR^{15a}$ and —$NR^{15a'}$, wherein each hydrogen atom in $C_1$-$C_6$ alkyl, $C_2$-$C_6$ alkenyl and $C_2$-$C_6$ alkynyl is independently optionally substituted by halogen, —$OR^{16a}$, —$SR^{16a}$, —$NR^{16a}R^{16a'}$, —C(O)$R^{16a}$, —C(O)O$R^{16a}$ or —C(O)N$R^{16a}R^{16a'}$; or $R^{5a}$ and $R^{6a}$ taken together with the carbon atom to which they are attached form a —C(O)—;

each $R^{7a}$, $R^{8a}$, $R^{9a}$, $R^{10a}$ and $R^{11a}$ is independently selected from the group consisting of H, halogen, $C_1$-$C_6$ alkyl, $C_2$-$C_6$ alkenyl, $C_2$-$C_6$ alkynyl, —CN, —NO$_2$, —NCO, —$OR^{17a}$, —$SR^{17a}$, —S(O)$_2OR^{17a}$, —$NR^{17a}R^{17a'}$, —P(O) (O$R^{17a}$)$_2$, —C(O)$R^{17a}$, —C(O)O$R^{17a}$ and —C(O) $NR^{17a}R^{17a'}$, wherein each hydrogen atom in $C_1$-$C_6$ alkyl, $C_2$-$C_6$ alkenyl and $C_2$-$C_6$ alkynyl is independently optionally substituted by halogen, —$OR^{18a}$, —$SR^{18a}$, —$NR^{18a}R^{18a'}$, —C(O)$R^{18a}$, —C(O)O$R^{18a}$ or —C(O)N$R^{18a}R^{18a'}$;

$R^{13a}$, $R^{13a'}$, $R^{14a}$, $R^{14a'}$, $R^{15a}$, $R^{15a'}$, $R^{16a}$, $R^{16a'}$, $R^{17a}$ and $R^{17a'}$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl, wherein each hydrogen atom in $C_1$-$C_7$ alkyl, $C_2$-$C_7$ alkenyl, $C_2$—$C_7$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by halogen, —OH, —SH, —NH$_2$ or —CO$_2$H;

each $R^{18a}$ and $R^{18a'}$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl —C(O)$R^{19a}$, —P(O)(O$R^{19a}$)$_2$, and —S(O)$_2OR^{19a}$, each $R^{19}$ is independently selected from H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl;

a is 1, 2 or 3; and

* represents a covalent bond to the rest of the conjugate.

In some embodiments, the therapeutic agent is of the formula

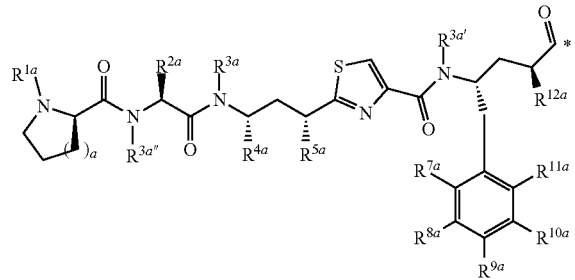

wherein $R^{1a}$, $R^{2a}$, $R^{3a}$, $R^{3a'}$, $R^{3a''}$, $R^{4a}$, $R^{5a}$, $R^{7a}$, $R^{8a}$, $R^{9a}$, $R^{10a}$, $R^{11a}$ and $R^{12a}$ are as described herein, and * represents a covalent bond to the rest of the conjugate.

In another embodiment, the therapeutic agent can be a naturally occurring tubulysin, or analog or derivative thereof, of the following general formula

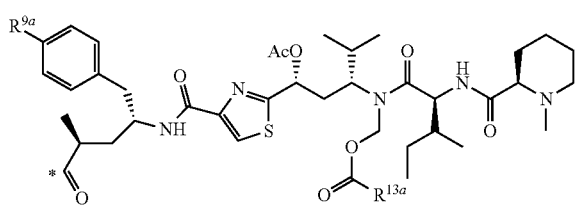

wherein $R^{9a}$ and $R^{13a}$ are as described herein, and * represents a covalent bond to the rest of the conjugate.

Conjugates of each of the foregoing tubulysins are described herein.

In some embodiments, the therapeutic agent can be a naturally occurring tubulysin of the following general formula

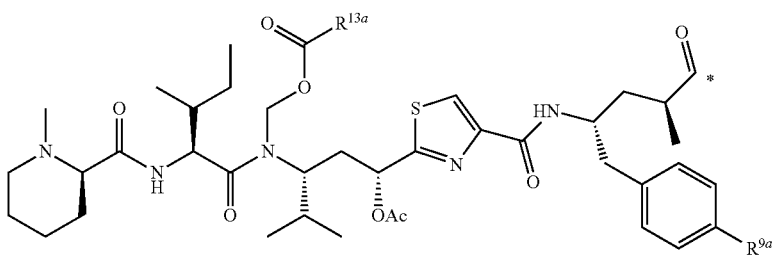

| Factor | $R^{13a}$ | $R^{9a}$ |
|---|---|---|
| A | $(CH_3)_2CHCH_2$ | OH |
| B | $CH_3(CH_2)_2$ | OH |
| C | $CH_3CH_2$ | OH |
| D | $(CH_3)_2CHCH_2$ | H |
| E | $CH_3(CH_2)_2$ | H |
| F | $CH_2CH_3$ | H |
| G | $(CH_3)_2C=CH$ | OH |
| H | $CH_3$ | H |
| I | $CH_3$ | OH | and * represents a covalent bond to the rest of the conjugate

Suitable molecules useful as imaging agents include, but are not limited to, dyes, such as fluorescein dyes, rhodamine dyes, near IR dyes, and SPECT imaging agents, such as any radionuclei chelator known in the art. Examples of rhodamine dyes include, but are not limited to, 5-carboxytetramethylrhodamine (5-TAMRA), rhodamine B, rhodamine 6G, TRITC, Texas Red, rhodamine 123, sulforhodamine 101, and the like. Examples of rhodamine dyes include, but are not limited to, fluorescein, 5-amino-fluorescein, 6-amino-fluorescein, fluorescein isocyanate (FITC), NHS-fluorescein, Oregon Green, Tokyo Green, Singapore Green, Philadelphia Green, and the like. Examples of near IR dyes include, S-0456. Examples of radionuclei chelators include, but are not limited to those described in WO03/092742. In some embodiments, the agent is a SPECT imaging agent. In some embodiments, the agent is a SPECT imaging agent of the formula

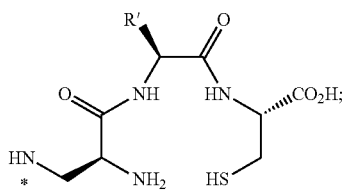

wherein R' is H, or R' is selected from the group consisting of $C_1$-$C_6$ alkyl, amino-$C_1$-$C_6$ alkyl, carboxy-$C_1$-$C_6$ alkyl, hydroxyl-$C_1$-$C_6$ alkyl, $C_1$-$C_6$ heteroalkyl, $C_6$-$C_{10}$ aryl, $C_6$-$C_{10}$ aryl-$C_1$-$C_6$ alkyl alkyl and $C_5$-$C_{10}$ heteroaryl-$C_1$-$C_6$ alkyl; and * represents a covalent bond to the rest of the conjugate. In some embodiments, a radionuclei is bound to the SPECT imaging agent.

In some embodiments, the agent is a SPECT imaging agent of the formula

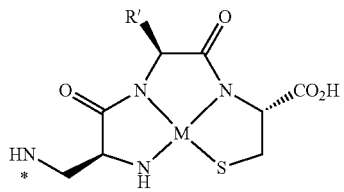

wherein M is a cation of a radionuclide, and * represents a covalent bond to the rest of the conjugate.

In some embodiments, the agent is a SPECT imaging agent of the formula

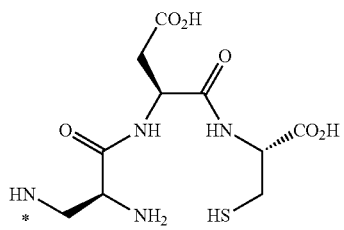 [SMILES: NC[C@H](N)C(=O)N[C@@H](CC(=O)O)C(=O)N[C@@H](CS)C(=O)O]

wherein * represents a covalent bond to the rest of the conjugate. In some embodiments, a radionuclei is bound to the SPECT imaging agent. In some embodiments, the agent is a SPECT imaging agent of the formula

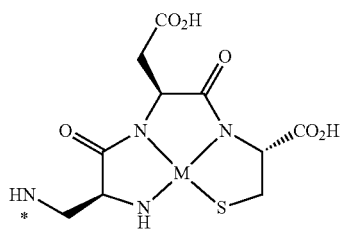

wherein M is a cation of a radionuclide, and * represents a covalent bond to the rest of the conjugate. In some embodiments, the radionuclei is selected from the group consisting of an isotope of gallium, an isotope of indium, an isotope of copper, an isotope of technetium, and an isotope of rhenium. In some embodiments, the radionuclei is an isotope of technetium. In some embodiments, the radionuclei is $^{99m}Tc$.

In one embodiment, the methods described herein can be used for both human clinical medicine and veterinary applications as a "subject". Thus, a "subject" can be administered the conjugates described herein, and can be human ("patient") or, in the case of veterinary applications, can be a laboratory, agricultural, domestic, or wild animal. In one aspect, the subject can be a human patient, a laboratory animal such as a rodent (e.g., mice, rats, hamsters, etc.), a rabbit, a monkey, a chimpanzee, domestic animals such as dogs, cats, and rabbits, agricultural animals such as cows, horses, pigs, sheep, goats, and wild animals in captivity such as bears, pandas, lions, tigers, leopards, elephants, zebras, giraffes, gorillas, dolphins, and whales.

In various embodiments, the cancers described herein can be a cancer cell population that is tumorigenic, including benign tumors and malignant tumors, or the cancer can be non-tumorigenic. The cancer can arise spontaneously or by such processes as mutations present in the germline of the patient or somatic mutations, or the cancer can be chemically-, virally-, or radiation-induced. Cancers applicable to the invention described herein include, but are not limited to, a carcinoma, a sarcoma, a lymphoma, a melanoma, a mesothelioma, a nasopharyngeal carcinoma, a leukemia, an adenocarcinoma, and a myeloma.

In some aspects the cancers can be lung cancer, bone cancer, pancreatic cancer, skin cancer, cancer of the head, cancer of the neck, cutaneous melanoma, intraocular melanoma uterine cancer, ovarian cancer, endometrial cancer, leiomyosarcoma, rectal cancer, stomach cancer, colon cancer, breast cancer, triple negative breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, non-small cell lung cancer, small cell lung cancer, cancer of the adrenal gland, sarcoma of soft tissue, cancer of the urethra, cancer of the penis, prostate cancer, chronic leukemia, acute leukemia, lymphocytic lymphomas, pleural mesothelioma, cancer of the bladder, Burkitt's lymphoma, cancer of the ureter, cancer of the kidney, renal cell carcinoma, carcinoma of the renal pelvis, neoplasms of the central nervous system (CNS), primary CNS lymphoma, spinal axis tumors, brain stem glioma, pituitary adenoma, cholangiocarcinoma, Hurthle cell thyroid cancer or adenocarcinoma of the gastroesophageal junction.

In some embodiments, the present disclosure relates to targeted NIR imaging, wherein the conjugate of the formula VI provides selective imaging of cells and tissues that express the CA IX protein. It will be appreciated that the in vitro or in vivo imaging method used in connection with the conjugate of the formula VI is not particularly limited, and may be any conventional in vitro or in vivo imaging method known in the art. Furthermore, such imaging methods known in the art can be carried out using any instrumentation or assay kit known in the art, including, but not limited to fluorescent microscopy systems, such as the Nikon 90i, in vivo fluorescence imaging systems, such as the Caliper IVIS Lumina II Imaging station (often coupled to an a camera, such as the ISOON5160 Andor Nikon camera), and the like.

In some embodiments, the present disclosure provides methods for imaging a population of cell or tissue, either in vitro or in vivo. It will be appreciated that such in vitro methods can be carried out by any method known in the art. In some embodiments, in vitro imaging methods described herein can include a. contacting a population of cells with the conjugate VI to provide the conjugate bound to cells expressing a CA IX protein, and b. visualizing the conjugate bound to cells by irradiation with near-infrared wavelength light. It will be appreciated that visualizing the conjugate bound to cells by irradiation with near-infrared wavelength light can include irradiation at an excitation wavelength and detection at an emission wavelength. Thus, in some embodiments, in vitro imaging methods described herein can include a. contacting a population of cells with the conjugate VI to provide the conjugate bound to cells expressing a CA IX protein, b. irradiating the conjugate bound to cells expressing a CA IX protein with near-infrared wavelength light, and c. detecting light emitted from the cancer cells at an emission wavelength.

In some embodiments, tissues, such as cancerous tumors, can be imaged according to the methods described herein. For example, in some embodiments, in vivo imaging methods described herein can include a. administering to the patient a conjugate of the formula VI; or a pharmaceutically acceptable salt thereof, to provide the conjugate bound to cells expressing a CA IX protein; and b. visualizing the conjugate bound to cells expressing a CA IX protein by irradiation with near-infrared wavelength light. It will be appreciated that visualizing the conjugate bound to cells by irradiation with near-infrared wavelength light can include irradiation at an excitation wavelength and detection at an emission wavelength. Thus, in some embodiments, in vivo imaging methods described herein can include a. administering to the patient a conjugate of the formula VI; or a pharmaceutically acceptable salt thereof, to provide the conjugate bound to cells expressing a CA IX protein; b. irradiating the conjugate bound to cells expressing a CA IX protein with near-infrared wavelength light; and c. detecting light emitted from the cancer cells at an emission wavelength. It will be appreciated that visualizing the conjugate bound to cells by irradiation with near-infrared wavelength light can be carried out using any known NIR imaging techniques (diagnostic or otherwise) or instrumentation known in the art.

The wavelength of light used in connection with the imaging methods described herein can be in the near-infrared wavelength region, such as in the range of about 600 nm to about 2500 nm. Such wavelength can be a range of wavelengths or a single wavelength. In some embodiments, the excitation wavelength can be in the range of from about 600 nm to about 2500 nm. In some embodiments, the excitation wavelength can be in the range of from about 600 nm to about 900 nm. In some embodiments, the excitation wavelength can be in the range of from about 700 nm to about 750 nm. In some embodiments, the excitation wavelength can be about 745 nm. In some embodiments, the emission wavelength can be in the range of from about 600 nm to about 2500 nm. In some embodiments, the emission wavelength can be in the range of from about 750 nm to about 900 nm. In some embodiments, the emission wavelength can be in the range of from about 750 nm to about 790 nm. In some embodiments, the emission wavelength can be about 790 nm. In some embodiments, the emission wavelength can be the emission wavelength of ICG (also known as indocyanine green dye).

In some embodiments, the present disclosure provide a process for the preparation a conjugate of the formula VI as shown in Scheme 1.

Scheme 1
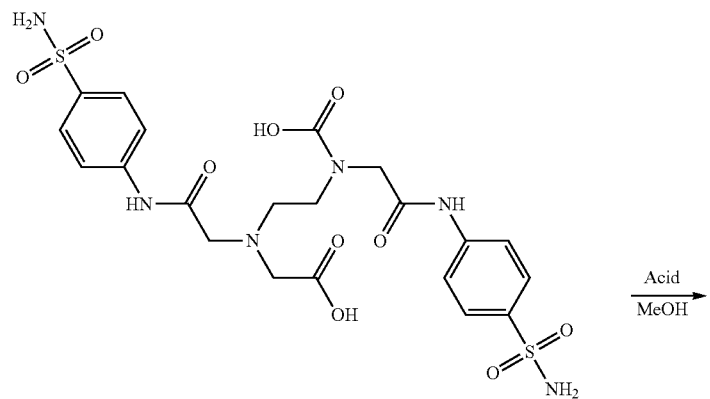
I
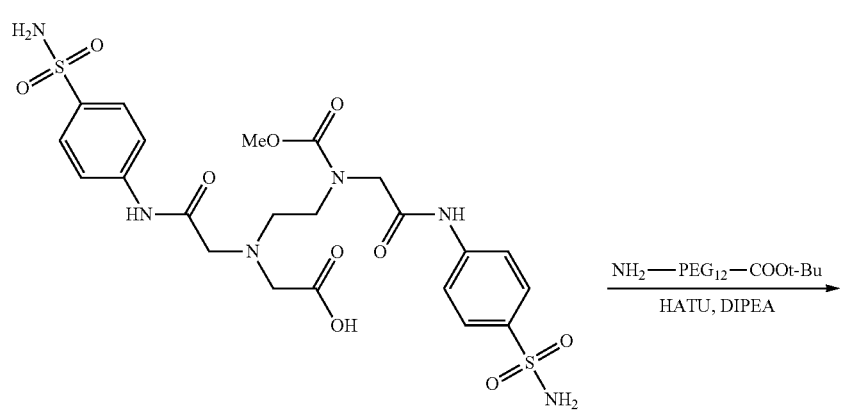
II
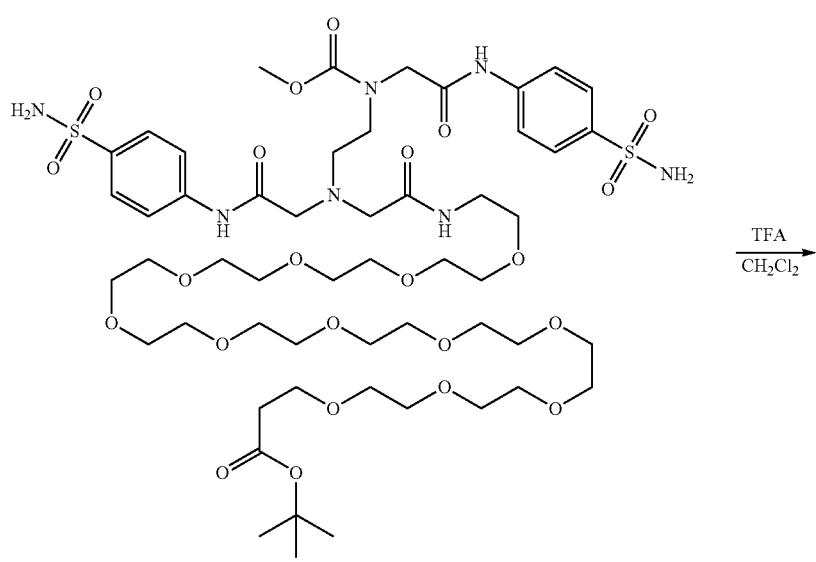
III

-continued
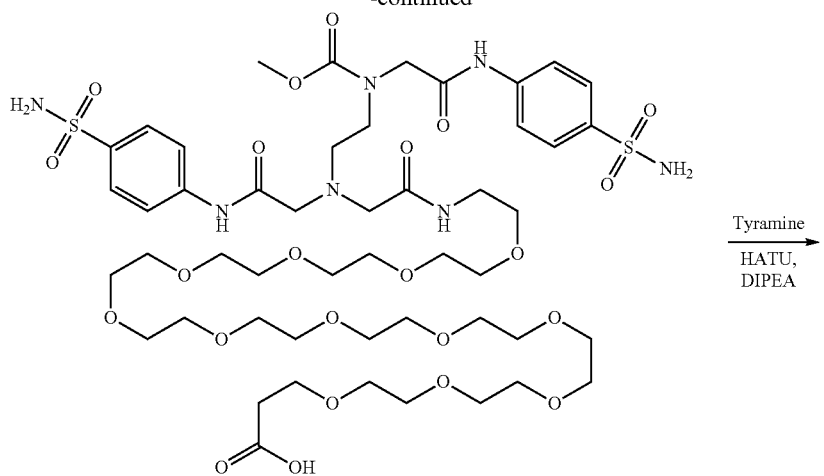
IV
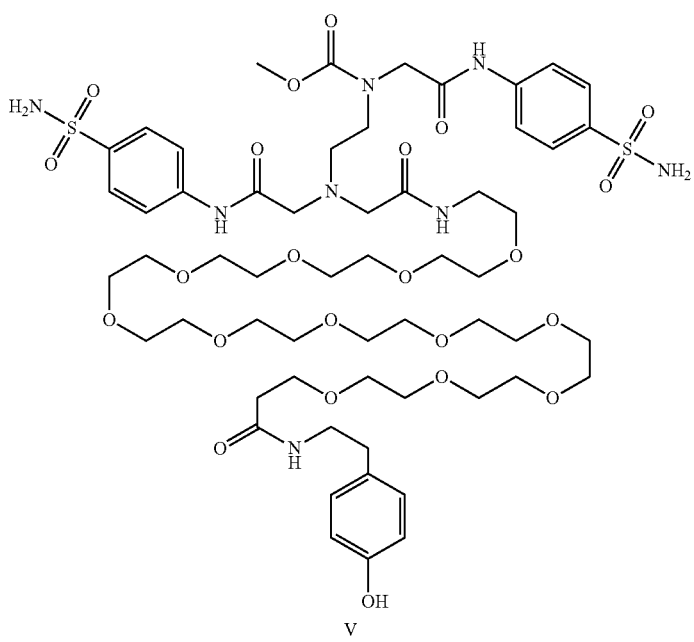
V

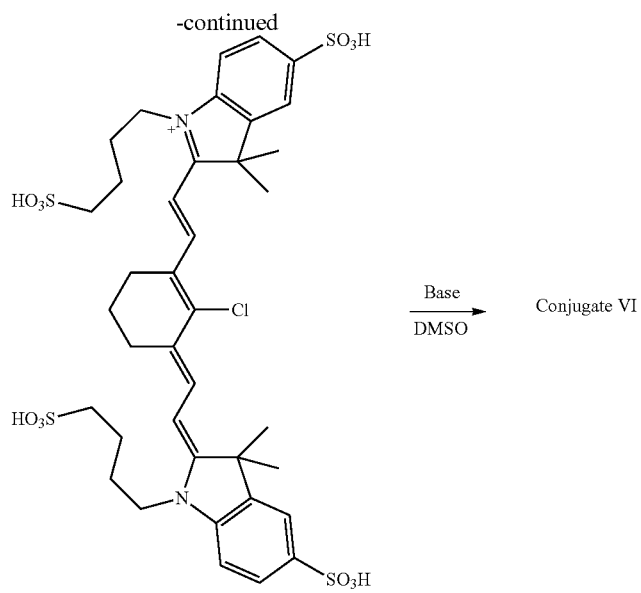

-continued

→ Base, DMSO → Conjugate VI

In other embodiments of the methods described herein, pharmaceutically acceptable salts of the conjugates described herein are provided. Pharmaceutically acceptable salts of conjugates described herein include acid addition and base salts thereof.

Suitable acid addition salts are formed from acids which form non-toxic salts. Illustrative examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts of the conjugates described herein are formed from bases which form non-toxic salts. Illustrative examples include the arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts.

In one embodiment, the conjugates described herein may be administered as a formulation in association with one or more pharmaceutically acceptable carriers. The carriers can be excipients. The choice of carrier will to a large extent depend on factors such as the particular mode of administration, the effect of the carrier on solubility and stability, and the nature of the dosage form. Pharmaceutical compositions suitable for the delivery of conjugates as described herein and methods for their preparation will be readily apparent to those skilled in the art. Such compositions and methods for their preparation may be found, for example, in Remington: The Science & Practice of Pharmacy, 21th Edition (Lippincott Williams & Wilkins, 2005), incorporated herein by reference.

In one illustrative aspect, a pharmaceutically acceptable carrier includes any and all solvents, dispersion media, coatings, antibacterial and antifungal agents, isotonic and absorption delaying agents, and the like, and combinations thereof, that are physiologically compatible. In some embodiments, the carrier is suitable for parenteral administration. Pharmaceutically acceptable carriers include sterile aqueous solutions or dispersions and sterile powders for the extemporaneous preparation of sterile injectable solutions or dispersions. Supplementary active compounds can also be incorporated into compositions of the invention.

In various embodiments, liquid formulations may include suspensions and solutions. Such formulations may comprise a carrier, for example, water, ethanol, polyethylene glycol, propylene glycol, methylcellulose or a suitable oil, and one or more emulsifying agents and/or suspending agents. Liquid formulations may also be prepared by the reconstitution of a solid.

In one embodiment, an aqueous suspension may contain the active materials in admixture with appropriate excipients. Such excipients are suspending agents, for example, sodium carboxymethylcellulose, methylcellulose, hydroxypropylmethylcellulose, sodium alginate, polyvinylpyrrolidone, gum tragacanth and gum acacia; dispersing or wetting agents which may be a naturally-occurring phosphatide, for example, lecithin; a condensation product of an alkylene oxide with a fatty acid, for example, polyoxyethylene stearate; a condensation product of ethylene oxide with a long chain aliphatic alcohol, for example, heptadecaethyleneoxycetanol; a condensation product of ethylene oxide with a partial ester derived from fatty acids and a hexitol such as polyoxyethylene sorbitol monooleate; or a condensation product of ethylene oxide with a partial ester derived from fatty acids and hexitol anhydrides, for example, polyoxyethylene sorbitan monooleate. The aqueous suspensions may also contain one or more preservatives, for example, ascorbic acid, ethyl, n-propyl, or p-hydroxybenzoate; or one or more coloring agents.

In one illustrative embodiment, dispersible powders and granules suitable for preparation of an aqueous suspension by the addition of water provide the active ingredient in admixture with a dispersing or wetting agent, suspending agent and one or more preservatives. Additional excipients, for example, coloring agents, may also be present.

Suitable emulsifying agents may be naturally-occurring gums, for example, gum acacia or gum tragacanth; naturally-occurring phosphatides, for example, soybean lecithin; and esters including partial esters derived from fatty acids and hexitol anhydrides, for example, sorbitan mono-oleate, and condensation products of the said partial esters with ethylene oxide, for example, polyoxyethylene sorbitan monooleate.

In other embodiments, isotonic agents, for example, sugars, polyalcohols such as mannitol, sorbitol, or sodium chloride can be included in the composition. Prolonged absorption of injectable compositions can be brought about by including in the composition an agent which delays absorption, for example, monostearate salts and gelatin.

Illustrative formats for oral administration include tablets, capsules, elixirs, syrups, and the like.

Depending upon the cancer type as described herein, the route of administration and/or whether the conjugates are administered locally or systemically, a wide range of permissible dosages are contemplated herein, including doses falling in the range from about 1 µg/kg to about 1 g/kg. The dosages may be single or divided, and may administered according to a wide variety of protocols, including q.d., b.i.d., t.i.d., or even every other day, biweekly (b.i.w.), once a week, once a month, once a quarter, and the like. In each of these cases it is understood that the therapeutically effective amounts described herein correspond to the instance of administration, or alternatively to the total daily, weekly, month, or quarterly dose, as determined by the dosing protocol.

In one aspect, a conjugate as described herein may be administered directly into the blood stream, into muscle, or into an internal organ. Suitable routes for such parenteral administration include intravenous, intraarterial, intraperitoneal, intrathecal, epidural, intracerebroventricular, intraurethral, intrasternal, intracranial, intratumoral, intramuscular and subcutaneous delivery. Suitable means for parenteral administration include needle (including microneedle) injectors, needle-free injectors and infusion techniques.

In one illustrative aspect, parenteral formulations are typically aqueous solutions which may contain carriers or excipients such as salts, carbohydrates and buffering agents (preferably at a pH of from 3 to 9), but, for some applications, they may be more suitably formulated as a sterile non-aqueous solution or as a dried form to be used in conjunction with a suitable vehicle such as sterile, pyrogen-free water. In other embodiments, any of the liquid formulations described herein may be adapted for parenteral administration of the conjugates described herein. The preparation of parenteral formulations under sterile conditions, for example, by lyophilization under sterile conditions, may readily be accomplished using standard pharmaceutical techniques well known to those skilled in the art. In one embodiment, the solubility of a conjugate as described herein used in the preparation of a parenteral formulation may be increased by the use of appropriate formulation techniques, such as the incorporation of solubility-enhancing agents.

In various embodiments, formulations for parenteral administration may be formulated for immediate and/or modified release. In one illustrative aspect, active agents of the invention (i.e., the conjugates described herein) may be administered in a time release formulation, for example in a composition which includes a slow release polymer. The active agents can be prepared with carriers that will protect the conjugate against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PGLA). Methods for the preparation of such formulations are generally known to those skilled in the art. In another embodiment, the conjugates described herein or compositions comprising the conjugates may be continuously administered, where appropriate.

In one embodiment, a kit is provided. If a combination of active conjugates as described herein is to be administered, two or more pharmaceutical compositions may be combined in the form of a kit suitable for sequential administration or co-administration of the compositions. Such a kit comprises two or more separate pharmaceutical compositions, at least one of which contains a conjugate described herein, and means for separately retaining the compositions, such as a container, divided bottle, or divided foil packet. In another embodiment, compositions comprising one or more conjugates as described herein, in containers having labels that provide instructions for use of the conjugates as described herein for patient selection and/or treatment are provided.

In one embodiment, sterile injectable solutions can be prepared by incorporating the active agent in the required amount in an appropriate solvent with one or a combination of ingredients described above, as required, followed by filtered sterilization. Typically, dispersions are prepared by incorporating the conjugate into a sterile vehicle which contains a dispersion medium and any additional ingredients of those described above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof, or the ingredients may be sterile-filtered together.

The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. In one embodiment, the proper fluidity can be maintained, for example, by the use of a coating such as lecithin, by the maintenance of the required particle size in the case of dispersion and by the use of surfactants.

Any effective regimen for administering the conjugates described herein can be used. For example, conjugates described herein can be administered as single doses, or the doses can be divided and administered as a multiple-dose daily regimen. Further, a staggered regimen, for example, one to five days per week can be used as an alternative to daily treatment, and for the purpose of the methods described herein, such intermittent or staggered daily regimen is considered to be equivalent to every day treatment and is contemplated. In one illustrative embodiment the patient is treated with multiple injections of a conjugate described herein to treat the cancer. In one embodiment, the patient is injected multiple times (preferably about 2 up to about 50 times) with a conjugate described herein, for example, at 12-72 hour intervals or at 48-72 hour intervals. Additional injections of a conjugate described herein can be administered to the patient at an interval of days or months after the initial injections(s) and the additional injections can prevent recurrence of the cancer.

Any suitable course of therapy with the conjugates described herein can be used. In one embodiment, individual doses and dosage regimens are selected to provide a total dose administered during a month of about 15 mg. In one illustrative example, a conjugate described herein is administered in a single daily dose administered five days a week, in weeks 1, 2, and 3 of each 4 week cycle, with no dose administered in week 4. In an alternative example, a conjugate described herein is administered in a single daily dose administered three days a week, of weeks 1, and 3 of each 4 week cycle, with no dose administered in weeks 2 and 4. In an alternative example, a conjugate described herein is administered biweekly on weeks 1 and 2, i.e. on days 1, 4, 8, 11, of a 3-week cycle. In an alternative example, a conjugate described herein is administered and once weekly on weeks 1 and 2, i.e. days 1 and 8 of a 3-week cycle.

The unitary daily dosage of the conjugates described herein can vary significantly depending on the patient condition, the cancer being treated, the route of administration of the conjugates described herein and tissue distribution, and the possibility of co-usage of other therapeutic treatments, such as radiation therapy or additional drugs in combination therapies. The effective amount to be administered to a patient is based on body surface area, mass, and physician assessment of patient condition. Therapeutically effective doses (also referred to herein as "therapeutically effective amount") can range, for example, from about 0.5 mg/m$^2$ to about 20.0 mg/m$^2$.

The conjugates described herein may contain one or more chiral centers, or may otherwise be capable of existing as multiple stereoisomers. Accordingly, it is to be understood that the present invention includes pure stereoisomers as well as mixtures of stereoisomers, such as enantiomers, diastereomers, and enantiomerically or diastereomerically enriched mixtures. The conjugates described herein may be capable of existing as geometric isomers. Accordingly, it is to be understood that the present invention includes pure geometric isomers or mixtures of geometric isomers.

It is appreciated that the conjugates described herein may exist in unsolvated forms as well as solvated forms, including hydrated forms. In general, the solvated forms are equivalent to unsolvated forms and are encompassed within the scope of the present invention. The conjugates described herein may exist in multiple crystalline or amorphous forms. In general, all physical forms are equivalent for the uses contemplated by the present invention and are intended to be within the scope of the present invention.

In another embodiment, compositions and/or dosage forms for administration of a conjugate described herein are prepared from a conjugate described herein with a purity of at least about 90%, or about 95%, or about 96%, or about 97%, or about 98%, or about 99%, or about 99.5%. In another embodiment, compositions and or dosage forms for administration of a conjugate described herein are prepared from a conjugate described herein with a purity of at least 90%, or at least 95%, or at least 96%, or at least 97%, or at least 98%, or at least 99%, or at least 99.5%.

EXAMPLES

Materials.

Protected amino acids were purchased from Chem-Impex International (Chicago, IL). H-Cys (Trt)-2-Cl-Trt resin was obtained from Novabiochem (San Diego, CA). Tubulysin B and its activated derivatives were a kind gift from Endocyte Inc. (West Lafayette, Ind.). 2-(1H-7-Azabenzotriazole-1-yl)-1,1,3,3-tetramethyl uronium hexafluorophosphate methanaminium (HATU) was obtained from Genscript Inc. (Piscataway, NJ). Sulfuric acid, methanol, DMSO, DMF, TFA, isopropyl alcohol, NH$_2$-PEG$_{12}$-COOH-tBu, diisopropylethylamine (DIPEA), piperidine, CF$_3$COOH, CH$_2$Cl$_2$, K$_2$CO$_3$, tyramine and all other chemical reagents were purchased from Sigma Aldrich. Pure coat Amine 24-well microtiter plates were purchased from BD Biosciences (San Jose, CA). All other cell culture reagents, syringes and disposable items were purchased from VWR (Chicago, IL).

Example 1

Synthesis of L1-Rhodamine, L2-Rhodamine and L3-Rhodamine

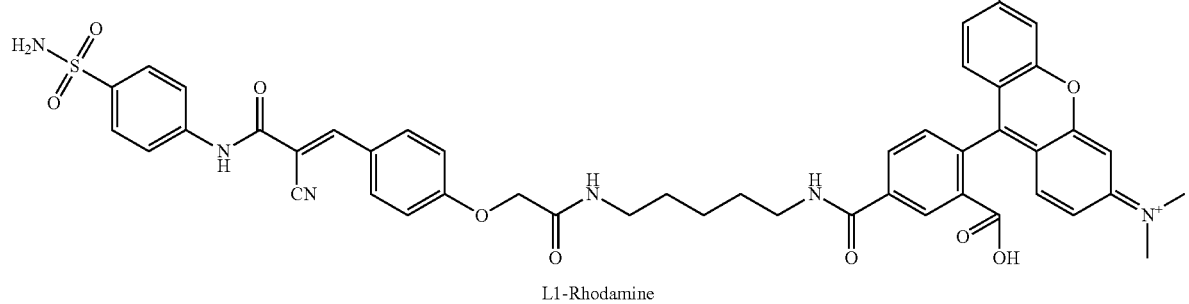

L1-Rhodamine

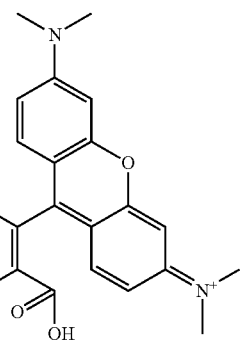
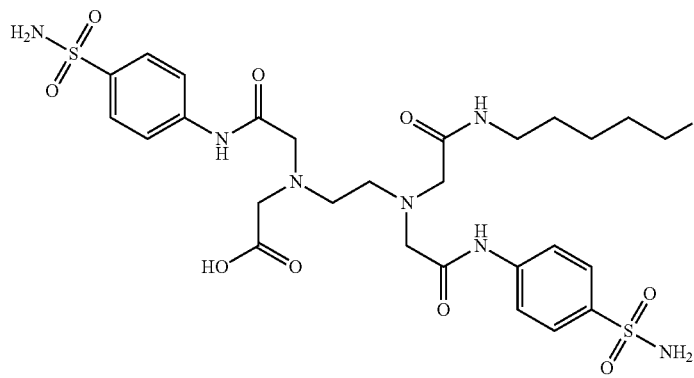

L2-Rhodamine

, and

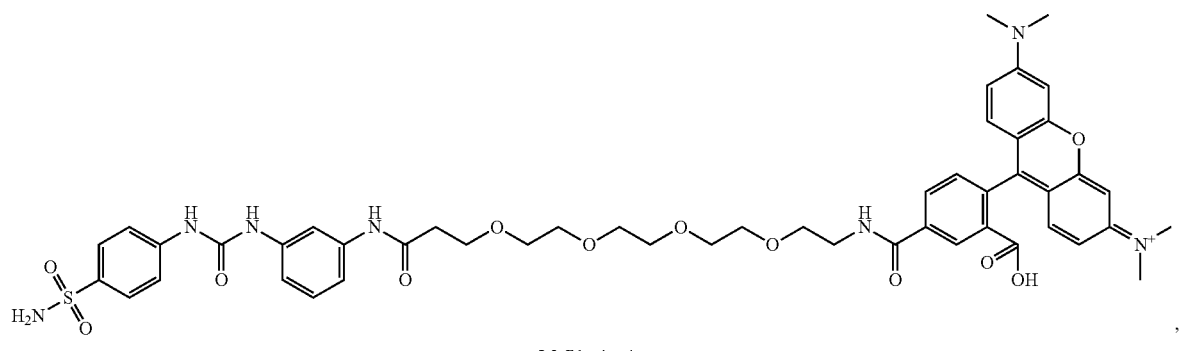

L3-Rhodamine

The CA IX inhibitors L1, L2 and L3 were prepared as previously described (See Rami M, Winum J Y, Innocenti A, Montero J L, Scozzafava A, Supuran C T. Carbonic anhydrase inhibitors: copper(II) complexes of polyamino-polycarboxylamido aromatic/heterocyclic sulfonamides are very potent inhibitors of the tumor-associated isoforms of IX and XII. *Bioorg Med Chem Lett.* 2008, 18(2):836-841, and Pacchiano F, Carta F, McDonald P C, Lou Y, Vullo D, Scozzafava A, Dedhar S, Supuran C T. Ureido-substituted benzenesulfonamides potently inhibit carbonic anhydrase IX and show antimetastatic activity in a model of breast cancer metastasis. *J Med Chem.* 2011, 54(6):1896-1902). The CA IX inhibitor was coupled with rhodamine derivative (5-((5-aminopentyl)carbamoyl)-2-(6-(dimethylamino)-3-(dimethyliminio)-3H-xanthen-9-yl)benzoate hydrochloride) in the presence of EDC.HCl and HOBt in DMSO for 12 hour yielded the target conjugate. For L1-Rhodamine, LRMS-LC/MS (m/z): [M+H]$^+$ calcd for $C_{48}H_{48}N_7O_9S$, 898.32; found, 898. For L2-Rhodamine, LRMS-LC/MS (m/z): [M+H]$^+$ calcd for $C_{52}H_{60}N_{10}O_{13}S_2$, 1097.39; found, 1097. For L3-Rhodamine, LRMS-LC/MS (m/z): [M+H]$^+$ calcd for $C_{49}H_{56}N_7O_{12}S$, 966.37; found, 966.1.

Example 2
Synthesis of L2-PEG$_{12}$-EC20, L2-PEG$_{36}$-EC20, L2-Pro$_3$-PEG12-EC20 and L3-PEG$_{12}$-EC20
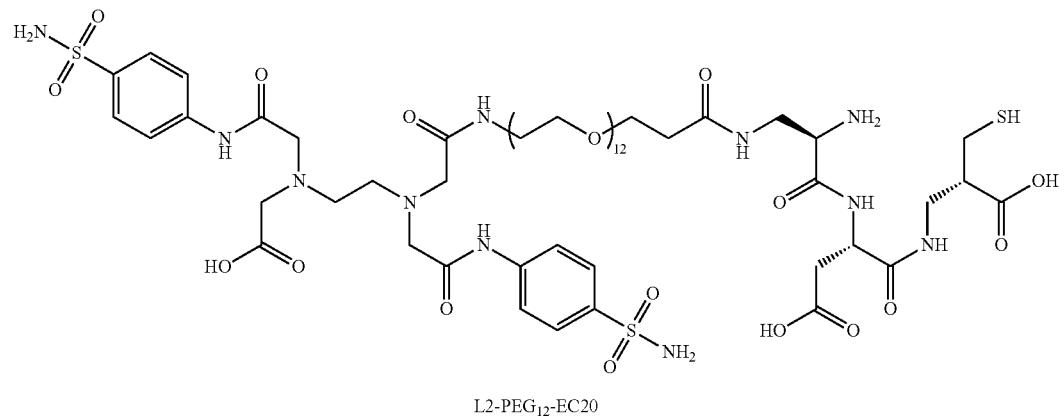
L2-PEG$_{12}$-EC20
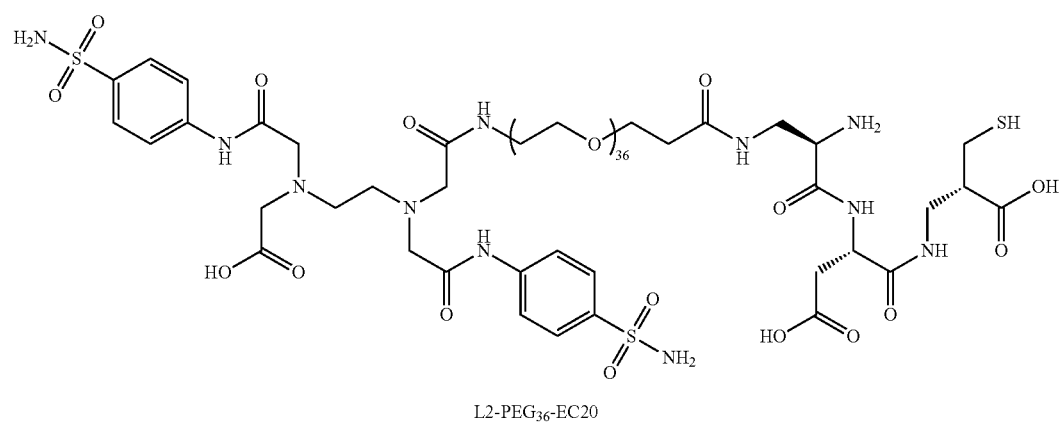
L2-PEG$_{36}$-EC20
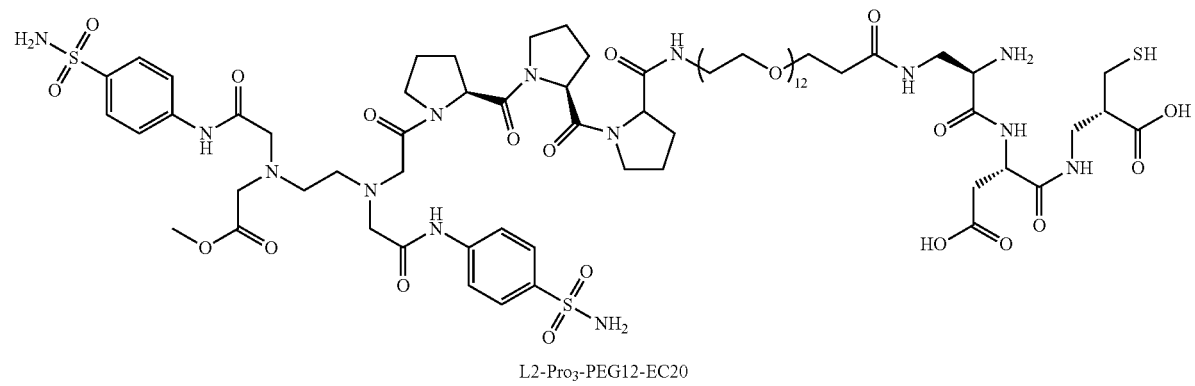
L2-Pro$_3$-PEG12-EC20

-continued

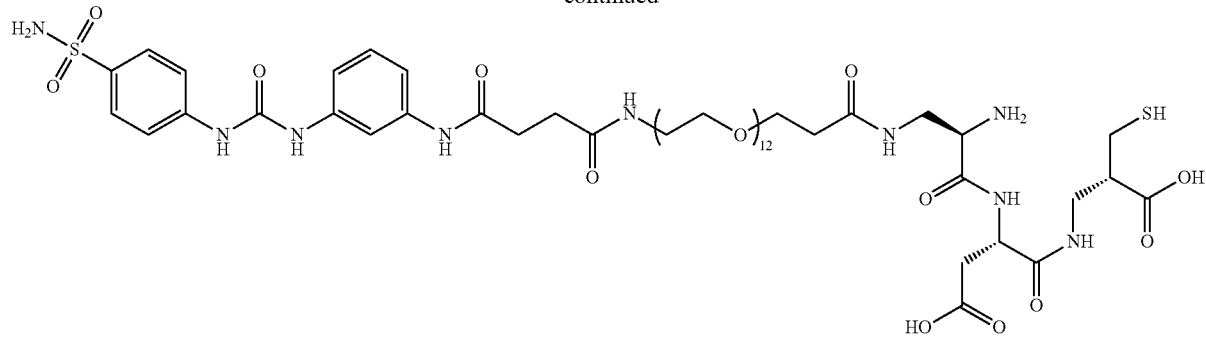

L3-PEG₁₂-EC20

All imaging conjugates were synthesized by the following solid phase methodology. H-Cys(Trt)-2-chlorotrityl resin (100 mg, 0.56 mM) was swollen with 3 mL of dichloromethane (DCM) followed by 3 mL of dimethylformamide (DMF). For three times, a 3 mL solution of 20% piperidine in DMF was added to the resin with argon bubbled through for 5 min. The resin was washed three times with 3 mL of DMF and 3 times with 3 mL isopropyl alcohol (i-PrOH). After swelling the resin in DMF, a solution of Fmoc-Asp (tBu)-OH (2.5 equiv), PyBOP (2.5 equiv) and DIPEA (4.0 equiv) in DMF was added. Argon was bubbled for 2 h, and resin was washed three times with 3 mL of DMF and 3 times with 3 mL i-PrOH.

For L2-PEG₁₂-EC20, the above sequence was repeated for three more coupling steps for addition of Boc-DAP (Fmoc)-OH, Fmoc-NH-PEG₁₂-COOH, and CA IX inhibitor L2. For L2-PEG₃₆-EC20, the above sequence was repeated for three more coupling steps for addition of Boc-DAP (Fmoc)-OH, Fmoc-NH-PEG₃₆-COOH, and CA IX inhibitor L2. For L2-Pro₃-PEG₁₂-EC20, the above sequence was repeated for six more coupling steps for addition of Boc-DAP(Fmoc)-OH, Fmoc-NH-PEG₃₆-COOH, three times proline and CA IX inhibitor L2. For L3-PEG₁₂-EC20, the above sequence was repeated for three more coupling steps for addition of Boc-DAP(Fmoc)-OH, Fmoc-NH-PEG₁₂-COOH and CA IX inhibitor L3.

Final compounds were cleaved from the resin using a trifluoroacetic acid (TFA): H₂O: triisopropylsilane: cocktail (95:2.5:2.5) and concentrated under vacuum. The concentrated product was precipitated in diethyl ether and dried under vacuum. Crude conjugate was purified by preparative RP-HPLC [A=2 mM ammonium acetate buffer (pH 7.0), B=CH₃CN, solvent gradient: 0% B to 100% B in 30 min] to yield the requisite product.

For L2-PEG₁₂-EC20 conjugate, LRMS-LC/MS (m/z): [M+H]⁺ calcd for $C_{59}H_{97}N_{11}O_{28}S_3$, 1503.57; found, 752.8 (half mass). For the L2-PEG₃₆-EC20 conjugate, LRMS-LC/MS (m/z): [M+H]⁺ calcd for $C_{108}H_{195}N_{11}O_{52}S_3$, 2574.21; found, 1281.6 (half mass). For L2-Pro₃-PEG₁₂-EC20, LRMS-LC/MS (m/z): [M+H]⁺ calcd for $C_{108}H_{195}N_{11}O_{52}S_3$, 1810.03; found, 1811.5. For L3-PEG₁₂-EC20, LRMS-LC/MS (m/z): [M+H]⁺ calcd for $C_{54}H_{87}N_9O_{24}S_2$, 1310.44; found, 655.8 (half mass).

Example 3

Preparation of CA IX Conjugated Near Infrared Fluorescent Dye (Conjugate VI)

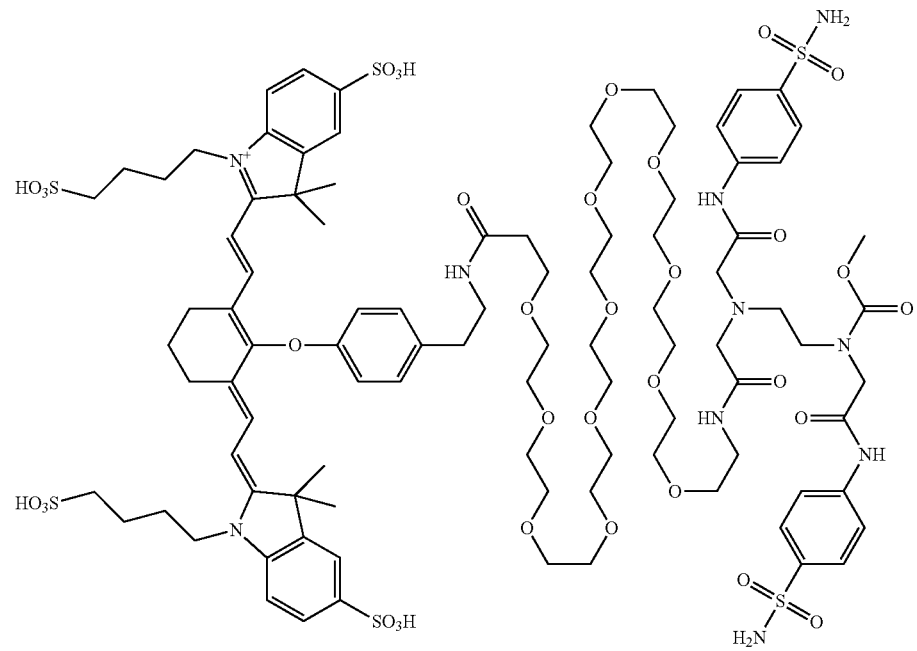 [SMILES: COC(=O)N(CCN(CC(=O)NCCOCCOCCOCCOCCOCCOCCOCCOCCOCCOCCOCCOCCC(=O)NCCc1ccc(OC2=C(/C=C/C3=[N+](CCCCS(=O)(=O)O)c4ccc(S(=O)(=O)O)cc4C3(C)C)CCC/C2=C\C=C2\N(CCCCS(=O)(=O)O)c3ccc(S(=O)(=O)O)cc3C2(C)C)cc1)CC(=O)Nc1ccc(S(N)(=O)=O)cc1)CC(=O)Nc1ccc(S(N)(=O)=O)cc1]

Step 1: One of the free carboxylic acid groups was protected by reaction of the CA IX ligand with concentrated sulfonic acid in methanol for 4 hours to provide compound II in 83% yield and 96% purity. The crude product was purified by preparative reverse-phase high-performance liquid chromatography. Exact Mass: 600.13 (Mol. weight 600.62)

Step 2: Compound II was reacted with $NH_2$-$PEG_{12}$-COO-t-Bu in the presence of HATU and DIPEA in DMSO solvent for 24 hours to provide compound III in 76% yield and 87% purity. The crude product was purified by preparative reverse-phase high-performance liquid chromatography. Exact Mass: 1239.55 (Mol. weight 1240.44)

Step 3: Compound III was deprotected by reaction with trifluoroacetic acid in methylene chloride for 4 hours to provide compound IV in 87% yield and 84% purity. The crude product was purified by preparative reverse-phase high-performance liquid chromatography. Exact Mass: 1199.48 (Mol. weight 1200.33)

Step 4: Compound IV was coupled with tyramine by reaction in the presence of HATU and DIPEA in DMSO solvent for 24 hours to provide compound V in 70% yield and 90% purity. The crude product was purified by preparative reverse-phase high-performance liquid chromatography. Exact Mass: 1318.56 (Mol. weight 1319.50)

Step 5: Compound V was reacted with the near infrared dye (S0456) in the presence of $K_2CO_3$ in DMSO for 3 hours to afford the final target conjugate VI (hypoxyfluor). The crude product was purified by preparative reverse-phase high-performance liquid chromatography with a gradient mobile phase consisting of 20 mM ammonium acetate buffer and 5% to 80% acetonitrile over 30 min (xTerra C18; Waters; 10 um; 19×250 mm). Elution of the conjugate was monitored at 280 nm and identities of eluted compounds were analyzed by liquid chromatography–mass spectrometry. Exact Mass: 2169.76 (Mol. weight 2171.54). The $\lambda_{ex}$=770 nm and the $\lambda_{em}$=790 nm Example 4

Preparation of CA IX Conjugated Rhodamine (CA IX-Rhodamine)

Step 1: One of the free carboxylic acid groups was protected by reaction of the CA IX ligand with concentrated sulfonic acid in methanol for 4 hours to provide compound II in 83% yield and 96% purity. The crude product was purified by preparative reverse-phase high-performance liquid chromatography. Exact Mass: 600.13 (Mol. weight 600.62)

Step 2: Compound II was reacted with $NH_2$-$PEG_{12}$-COO-t-Bu in the presence of HATU and DIPEA in DMSO solvent for 24 hours to provide compound III in 76% yield and 87% purity. The crude product was purified by preparative reverse-phase high-performance liquid chromatography. Exact Mass: 1239.55 (Mol. weight 1240.44)

Step 3: Compound III was deprotected by reaction with trifluoroacetic acid in methylene chloride for 4 hours to provide compound IV in 87% yield and 84% purity. The crude product was purified by preparative reverse-phase high-performance liquid chromatography. Exact Mass: 1199.48 (Mol. weight 1200.33)

Step 4: Compound IV was reacted with (5-((5-aminopentyl)carbamoyl)-2-(6-(dimethylamino)-3-(dimethyliminio)-3H-xanthen-9-yl)benzoate hydrochloride) in the presence of EDC.HCl and HOBt in DMSO for 12 hours to provide the final target conjugate CA IX-Rhodamine. For the near infrared fluorescent dye, the resulting deprotected compound was coupled with tyramine to introduce the phenolic group, which then was reacted with the near infrared dye (S0456) to afford the final target conjugate, named Hypoxyfluor. The crude product was purified by preparative reverse-phase high-performance liquid chromatography with a gradient mobile phase consisting of 20 mM ammonium acetate buffer and 5% to 80% acetonitrile over 30 min (xTerra C18; Waters; 10 um; 19×250 mm). Elution of the conjugate was monitored at 280 nm and identities of eluted compounds were analyzed by liquid chromatographymass spectrometry.

Example 5

Synthesis of Tubulysin B Conjugate

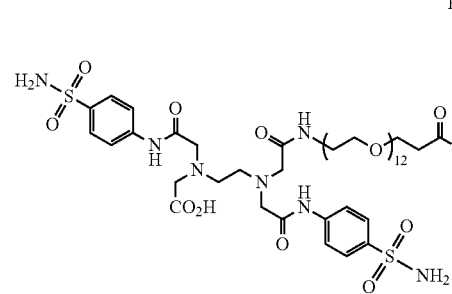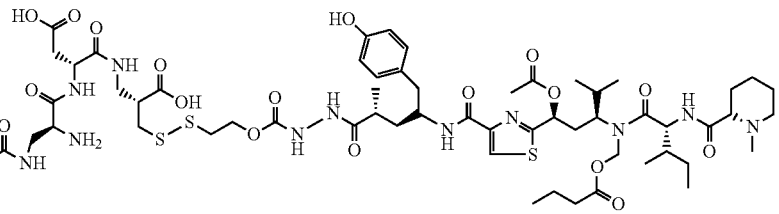

L2-Tubulysin B was synthesized from L2-$PEG_{12}$-EC20. A solution of saturated sodium bicarbonate (2 mL) in HPLC grade water was bubbled with argon continuously for 10 min. L2-$PEG_{12}$-EC20 (50 mg, 0.033 mmol) was dissolved in argon-purged HPLC grade water (2.0 mL) and the pH of the reaction mixture was increased to 7 using argon purged sodium bicarbonate. A solution of disulfide activated-Tubulysin B (37.47 mg, 0.034 mmol) in THF (2.0 mL) was then added to the reaction mixture. The progress of the reaction was monitored using analytical LCMS, and after stirring for 30 min, the reaction was found to reach completion. Crude L2-Tubulysin B was purified by preparative RP-HPLC [A=2 mM ammonium acetate buffer (pH 7.0), B=$CH_3CN$, solvent gradient: 0% B to 100% B in 30 min] to yield the requisite product. LRMS-LC/MS (m/z): [M+H]$^+$ calcd for $C_{104}H_{164}N_{18}O_{39}S_5$, 2450.84; found, 1225 (half mass).

In Vitro Experiments

Example 6

Figure 2:
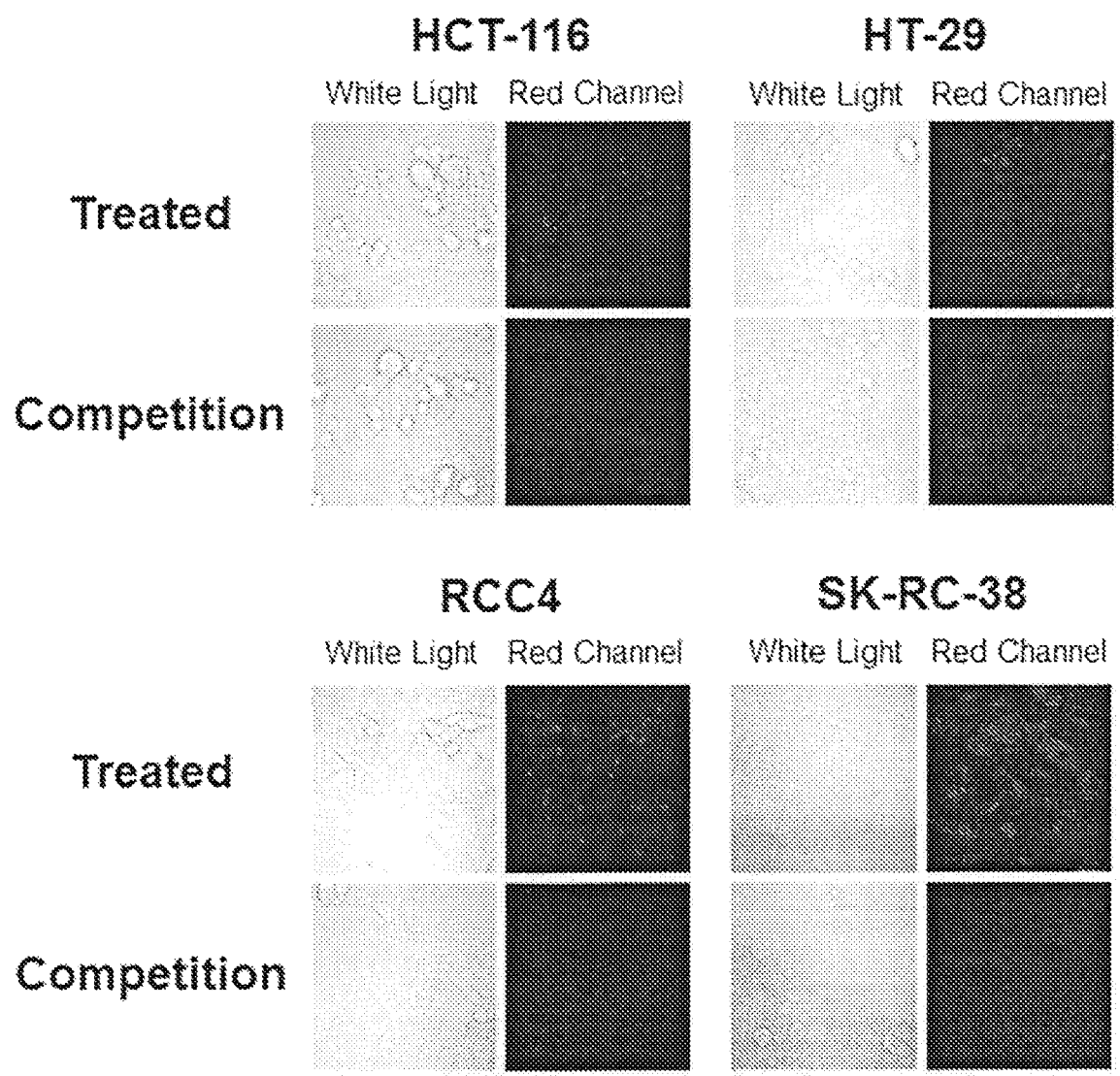
FIG. 2 shows the in vitro binding of CA IX rhodamine conjugate to various CA IX expressing cell lines. The fluorescent CA IX-Rhodamine conjugate (100 nM) was incubated with various cell lines in the presence or absence of 100-fold excess unlabeled CA IX ligand (10 μM). After washing, white light and fluorescent microscopy were used to visualize binding.

Fluorescent Microscopy a. HT-29 cells (10$^5$) were seeded into chambered coverglass plates and allowed to grow to confluence over 48-72 hr. Spent medium was replaced with 0.5 mL of fresh medium containing 0.5% bovine serum albumin and various concentrations of the dye conjugate (L1-Rhodamine, L2-Rhodamine or L3-Rhodamine) alone or the dye conjugate plus 100-fold excess CA IX inhibitor L1, L2 or L3, where appropriate. After incubation for 1 hour at 37° C., cells were rinsed twice with 1 mL of incubation solution to remove unbound fluorescence and 0.5 ml of fresh incubation medium was added to the wells. Images were acquired using a confocal microscopy (FV 1000, Olympus). Results are shown in FIG. 1. The two conjugates L2-Rhodamine or L3-Rhodamine both bound the cells and were competed in the presence of excess unconjugated inhibitor, indicating a specific receptor-specific binding event.

b. HCT-116, HT-29, RCC4 and SK-RC-38 human cancer cell lines ($10^5$) were seeded into chambered coverglass plates and allowed to grow to confluence over 48-72 hr. Spent medium was replaced with 0.5 mL of fresh medium containing 0.5% bovine serum albumin, and various concentrations of the dye conjugate (L2-Rhodamine) alone or the dye conjugate plus 100-fold excess CA IX inhibitor L2 were added. After incubation for 1 hour at 37° C., cells were rinsed with incubation solution (2×1.0 mL) to remove unbound conjugate then washed with PBS (1×1.0 mL). Images were acquired using confocal microscopy (FV 1000, Olympus). Results are shown in FIG. 2. As shown in FIG. 2, binding is observed in every cell line tested and when the fluorescent conjugate was incubated in the presence of 10-fold competing unconjugated CA IX inhibitor, essentially no binding was observed. Without being bound by theory, this result supports a highly specific receptor-mediated binding. Additionally, the punctate appearance in several of the cell lines is indicative of a rapid internalization of the bound conjugate.

c. HT-29 cells ($10^5$) were seeded into chambered coverglass plates and allowed to grow to confluence over 48-72 hr. Spent medium was replaced with 0.5 mL of fresh serum free medium containing 50 nM Hypoxyfluor or CA IX-Rhodamine in the presence or absence of 100-fold excess CA IX inhibitor. After incubation for 1 hour at 37° C., cells were rinsed three times with 1 mL of incubation solution to remove unbound fluorescence and 0.5 mL of fresh medium was added to the wells. Images were acquired using confocal microscopy (FV 1000, Olympus) for CA IX-Rhodamine and fluorescent microscopy (Nikon 90i) for Hypoxyfluor.

Figure 3A:
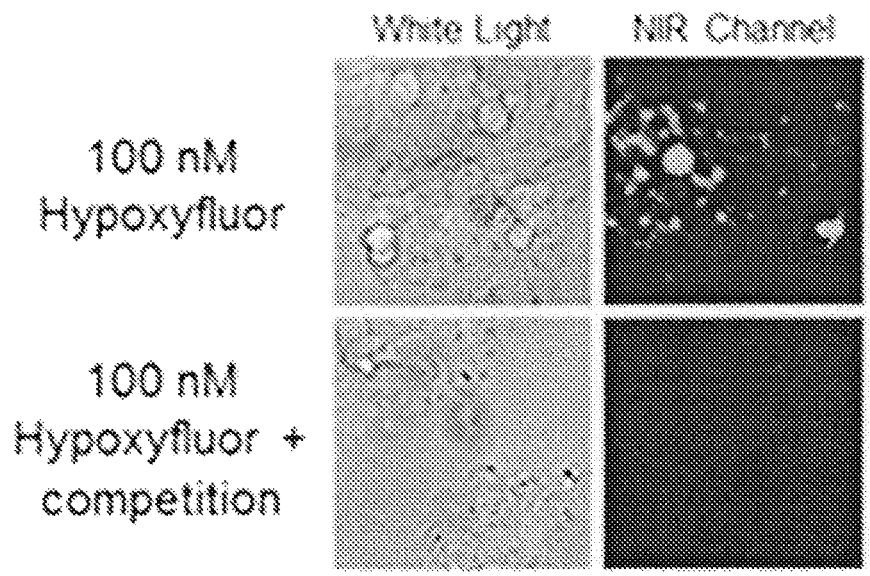
In FIG. 3A, HT-29 cells were incubated with 100 nM Hypoxyfluor in the presence or absence of 100-fold excess of the CA IX inhibitor. After washing, the cell-associated fluorescence was imaged using a nonconfocal fluorescence microscope that could be excited at 747 nm; i.e. the wavelength where the NIR dye absorbs. Because the emitted light is not visible to the eye, the image is false colored green.
Figure 3B:
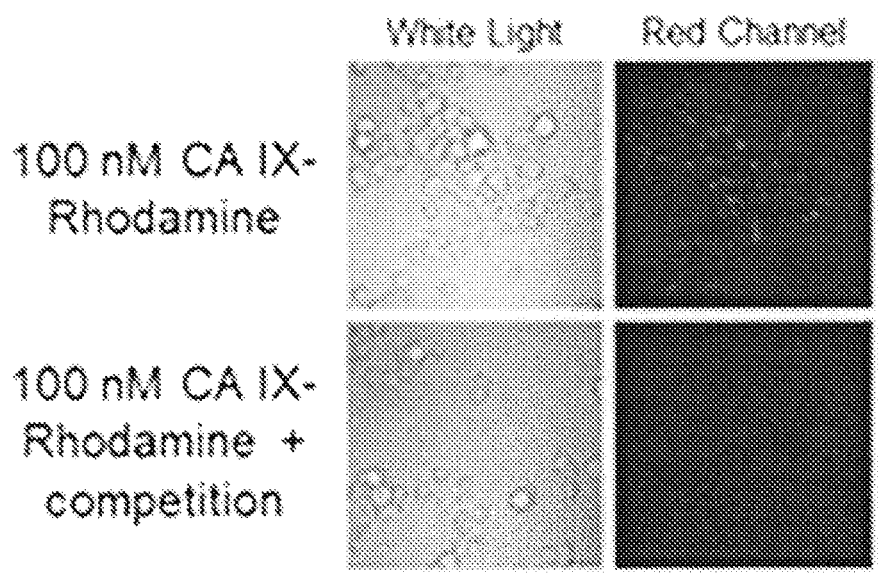
In FIG. 3B, HT-29 cells were similarly incubated with 100 nM CA IX-targeted rhodamine in the presence or absence of 100-fold excess CA IX inhibitor. After washing, the cell-associated fluorescence was imaged by confocal microscopy.

HT-29 cells that naturally express CA IX were used to determine cancer cell uptake and binding affinity of the newly synthesized conjugate. For this purpose, various concentrations of Hypoxyfluor and a fluorescent rhodamine conjugate (CA IX-rhodamine) were incubated with HT-29 cells for 1 hour, after which unbound conjugate was removed by washing. Cell associated fluorescence was imaged via fluorescent microscopy for Hypoxyfluor and confocal microscopy for CA IX-Rhodamine. Fluorescence was quantitated as described above to determine binding affinity. As shown in FIGS. 3A and 3B, Hypoxyfluor and CA IX-rhodamine binding was seen on both the cell surface and internal endosomes of cultured HT-29 cells.

Example 7

$^{99m}$Tc Conjugates Binding to HT-29 Cells

HT-29 cells (150,000 cells/well in 500 μL) were seeded into 24-well Falcon plates and allowed to form monolayers over 48 h. Spent medium in each well was replaced with 0.5 mL fresh medium containing increasing concentrations of various conjugates (L2-PEG$_{12}$-EC20, L2-PEG$_{36}$-EC20, L2-Pro$_3$-PEG12-EC20 and L3-PEG$_{12}$-EC20) bound with $^{99m}$Tc in the presence or absence of 100-fold excess CA IX inhibitors L1, L2 or L3, where appropriate. After incubating for 1 h at 37° C., cells were rinsed twice with 1 mL of medium and 1 mL of tris buffer. After dissolving in 0.5 mL of 0.25 M NaOH (aq), cells were transferred into individual γ-counter tubes and radioactivity was counted using a γ-counter (Packard, Packard Instrument Company). Apparent K$_D$ was calculated by plotting bound radioactivity versus the concentration of radiotracer using GraphPad Prism 4. Results are shown in Table 1.

TABLE 1

| Conjugate | Binding Affinity (nM) |
| --- | --- |
| L2-PEG$_{12}$-EC20 | 54 |
| L2-PEG$_{36}$-EC20 | 57 |
| L2-Pro$_3$-PEG12-EC20 | 67 |
| L3-PEG$_{12}$-EC20 | 146 |

L2-PEG$_{12}$-EC20 and L3-PEG$_{12}$-EC20 exhibited binding affinities of 54 and 146 nM, respectively. The reported K$_i$ of the original ligands L2 and L3 were 7.8 and 0.9 nM, respectively (See Rami et al. and Pacchiano et al. cited herein) meaning the addition of the PEG$_{12}$-EC20 decreased the binding by ~7- and 162-fold, respectively.

As the binding affinity for L2 was not as severely impacted by the addition of the linker, two additional conjugates using a PEG$_{36}$ and a Proline$_3$-PEG$_{12}$ linker were synthesized to explore the effect of different linkers on binding. The binding affinity for the two newly synthesized conjugates was 57 and 67 nM respectively,; essentially the same as the L2-PEG$_{12}$-EC20 conjugate.

Example 8

Binding of Hypoxyfluor to HT-29 Cells

HT-29 cells ($10^5$) were seeded into 24-well BD purecoat amine plates and allowed to grow to confluence over 48-72 hr. Spent medium was replaced with 0.5 mL of fresh medium containing 0.5% bovine serum albumin, and various concentrations of the dye conjugate alone or the dye conjugate plus 100-fold excess CA IX ligand were added. After incubation for 1 hour at 37° C., cells were rinsed with incubation solution (2×1.0 mL) to remove unbound fluorescence and dissolved in 0.5 mL of 1% aqueous sodium dodecyl sulfate. Cell associated fluorescence was then measured using an excitation of 745 nm and emission of 790 nm. All experiments were performed in triplicate. The dissociation constant (K$_D$) was calculated from a plot of cell bound fluorescence (RFU) versus the concentration of fluorescent conjugate added using the program, Graphpad Prism, and assuming a noncooperative single site binding equilibrium.

Figure 4:
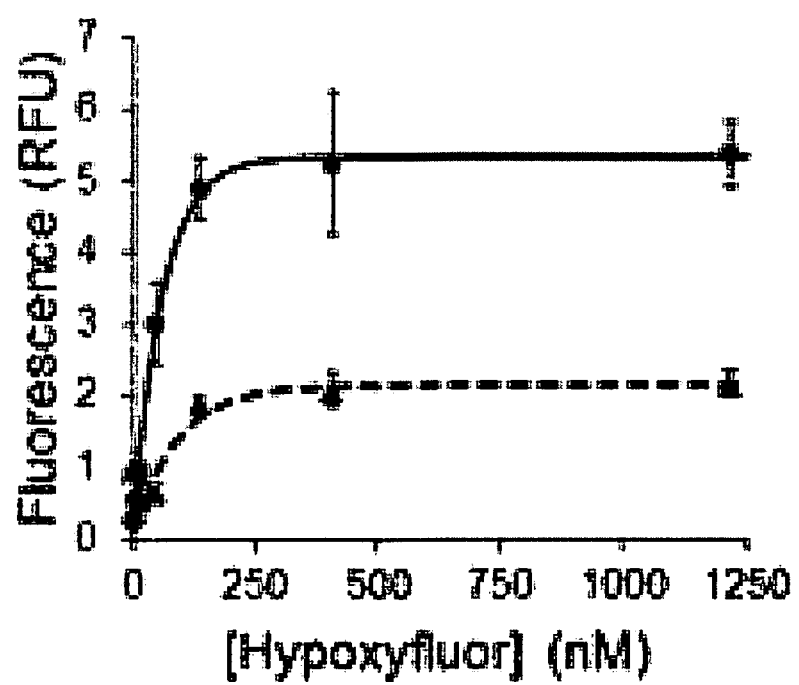
FIG. 4 shows HT-29 cells incubated with various concentrations of Hypoxyfluor in the presence or absence of 100-fold excess CA IX inhibitor. After washing, the remaining fluorescence was quantitated by fluorescence spectroscopy. Error bars represent standard deviation.

Hypoxyfluor binding was found to be saturable with an apparent dissociation constant of 45 nM (FIG. 4). Since the reported K$_I$ of the unmodified original ligand was 7.8 nM (See Rami, et. al.), attachment of the PEG linker and fluorophore only moderately attenuates CA IX binding affinity. When a 100-fold excess of the unconjugated ligand was pre-incubated with the HT-29 cells, most of the Hypoxyfluor or CA IX-Rhodamine binding was competed, demonstrating that the majority of cell uptake was receptor specific In Vivo Experiments

Example 9

Animal Husbandry

Athymic nu/nu mice were purchased from Harlan Laboratories, housed in a sterile environment on a standard 12 hour lightdark cycle and maintained on normal rodent chow. All animal procedures were approved by the Purdue Animal Care and Use Committee in accordance with National Institutes of Health guidelines.

Example 10

$^{99m}$Tc-L2-PEG$_{36}$-EC20 In Vivo Imaging and Biodistribution

Five-week-old male nu/nu mice were inoculated subcutaneously with HT-29 cells ($5.0 \times 10^6$/mouse) on their shoulders. Growth of the tumors was measured in two perpendicular directions every 2 days using a caliper (body weights were monitored on the same schedule), and the volumes of the tumors were calculated as $0.5 \times L \times W^2$ (L=longest axis and W=axis perpendicular to L in millimeters). Once tumors reached between 400 and 500 mm$^3$ in volume, animals were administered $^{99m}$Tc-bound conjugate L2-PEG$_{36}$-EC20 (10 nmol, 150 µCi) in saline (100 µL) via tail vein injection. At various times, animals were sacrificed by CO$_2$ asphyxiation. Images were acquired by shielding the kidneys via a Kodak Imaging Station (In-Vivo FX, Eastman Kodak Company) in combination with CCD camera and Kodak molecular imaging software (version 4.0). Radioimages: illumination source=radio isotope, acquisition time=3 min, f-stop=4, focal plane=5, FOV=160, binning=4. White light images: illumination source=white light transillumination, acquisition time=0.05 s, f-stop=16, focal plane=5, FOV=160 with no binning. Following imaging, animals were dissected and selected tissues were collected to preweighed γ-counter tubes. Radioactivity of preweighed tissues and $^{99m}$Tc-bound conjugates (10 nmol, 150 µCi) in saline (100 µL) was counted in a γ-counter. CPM values were decay corrected, and results were calculated as % injected dose (ID)/gram of wet tissue. Results of images at 4, 9 and 24 hours are shown in FIGS. 5, 6 and 7.

Figure 5A:
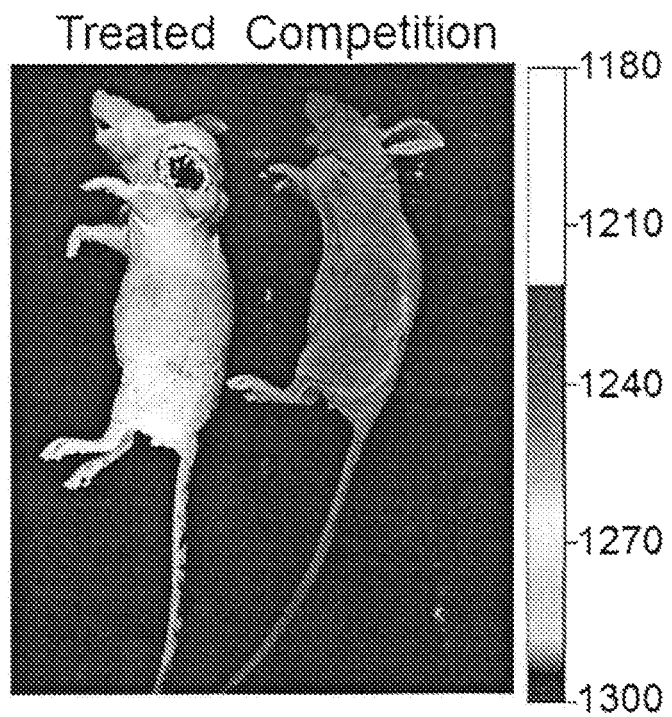
FIG. 5A shows images of mice bearing HT-29 xenograft tumors that were administered $^{99m}$Tc coordinated L2-PEG$_{36}$-EC20 (10 nmol) via tail vein injection (left mouse in panel) or 100 nmol unlabeled L2 ligand (right mouse in panel). Whole animal images were taken 4 hours post-injection.
Figure 5B:
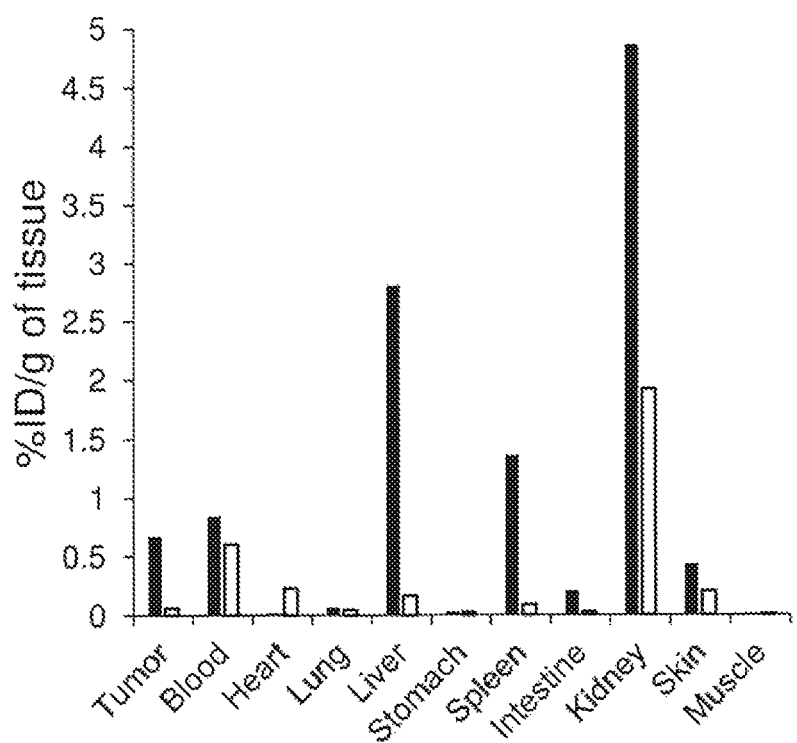
FIG. 5B shows biodistribution after organs were excised, washed, weighed and the amount of radioactivity present was determined at 4 hours post-injection. The percentage of the injected dose per gram of tissue was determined and plotted. Error bars represent standard deviation. (□) Competition; (■) L2-PEG$_{36}$-EC20.
Figure 6A:
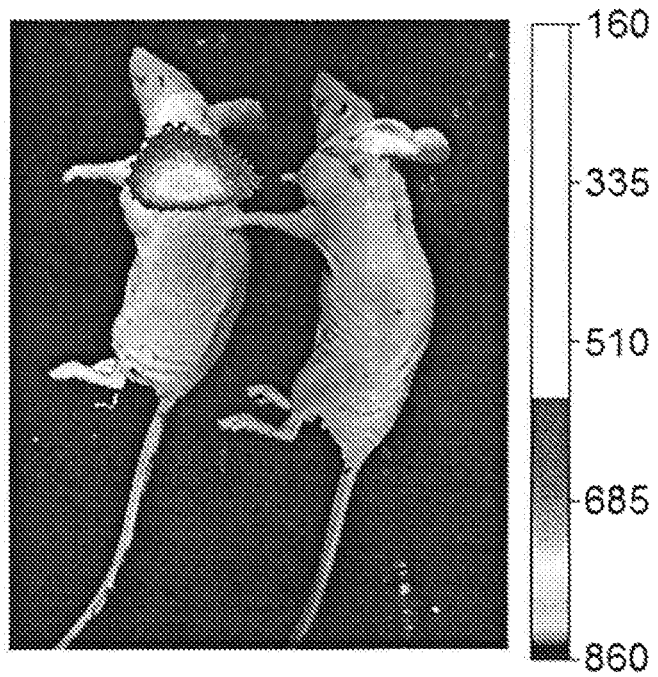
FIG. 6A shows images of mice bearing HT-29 xenograft tumors that were administered $^{99m}$Tc coordinated L2-PEG$_{36}$-EC20 (10 nmol) via tail vein injection (left mouse in panel) or 100 nmol unlabeled L2 ligand (right mouse in panel). Whole animal images were taken 9 hours post-injection.
Figure 6B:
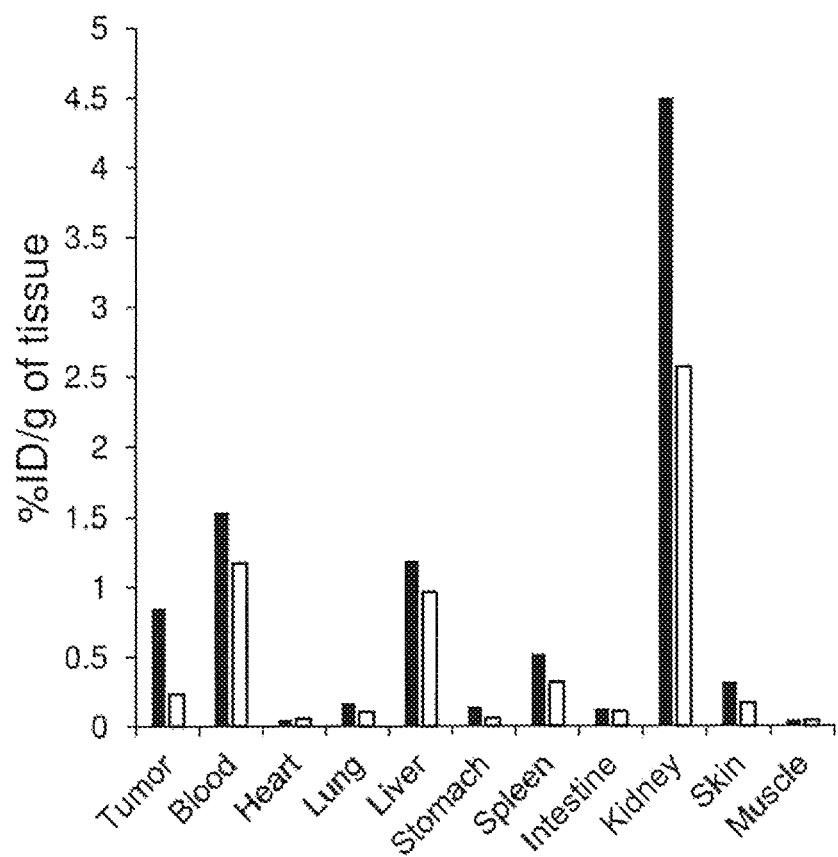
FIG. 6B shows biodistribution after organs were excised, washed, weighed and the amount of radioactivity present was determined at 9 hours post-injection. The percentage of the injected dose per gram of tissue was determined and plotted. Error bars represent standard deviation. (□) Competition; (■) L2-PEG$_{36}$-EC20.
Figure 7A:
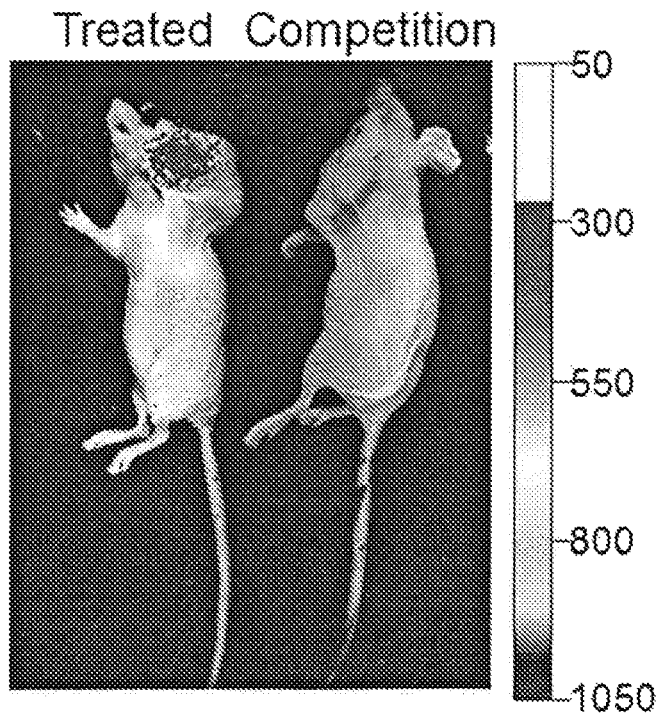
FIG. 7A shows images of mice bearing HT-29 xenograft tumors that were administered $^{99m}$Tc coordinated L2-PEG$_{36}$-EC20 (10 nmol) via tail vein injection (left mouse in panel) or 100 nmol unlabeled L2 ligand (right mouse in panel). Whole animal images were taken 24 hours post-injection.
Figure 7B:
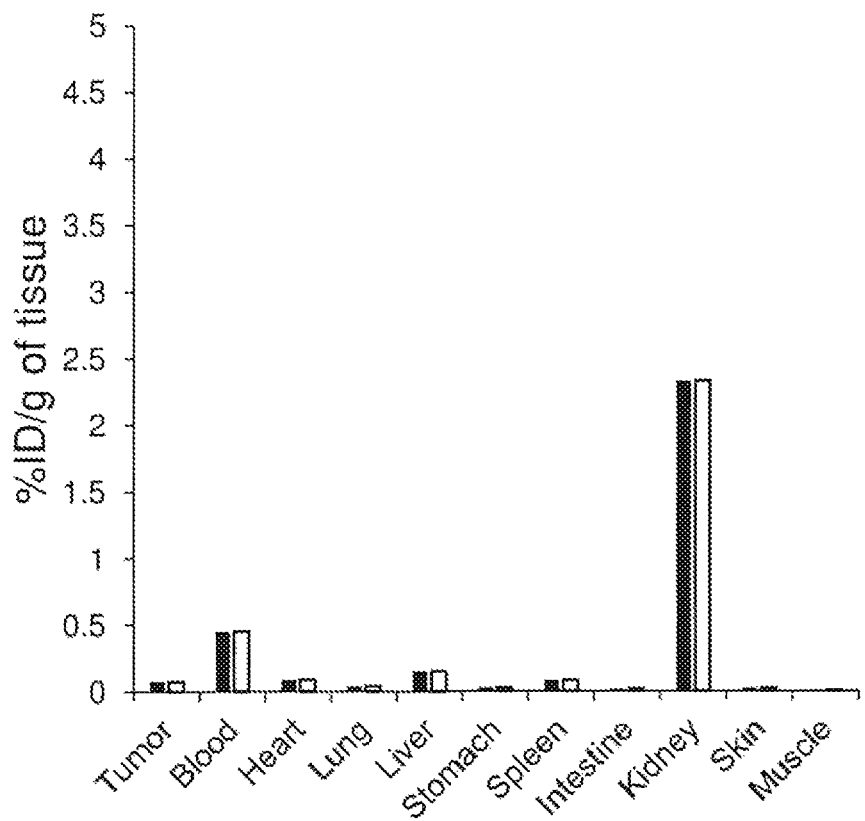
FIG. 7B shows biodistribution after organs were excised, washed, weighed and the amount of radioactivity present was determined at 24 hours post-injection. The percentage of the injected dose per gram of tissue was determined and plotted. Error bars represent standard deviation. (□) Competition; (■) L2-PEG$_{36}$-EC20.
Figure 8A:
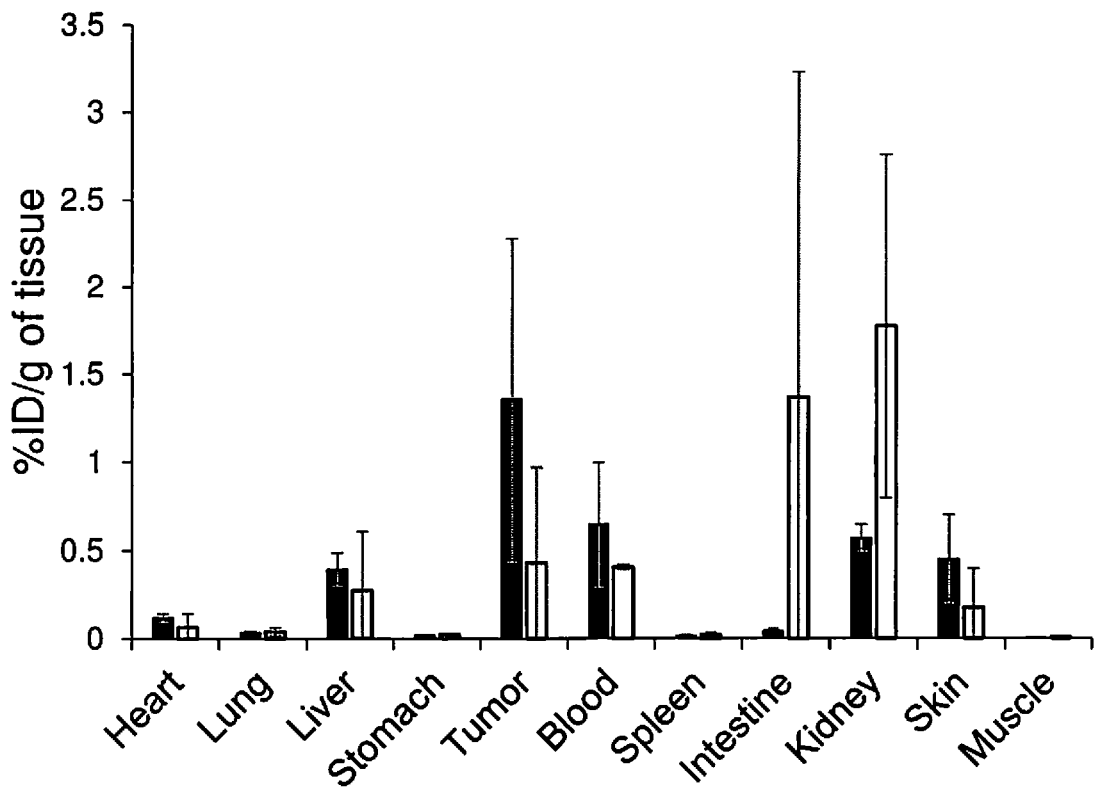
FIG. 8A: (□) Competition; (■) L2-PEG$_{12}$-EC20.
Figure 8B:
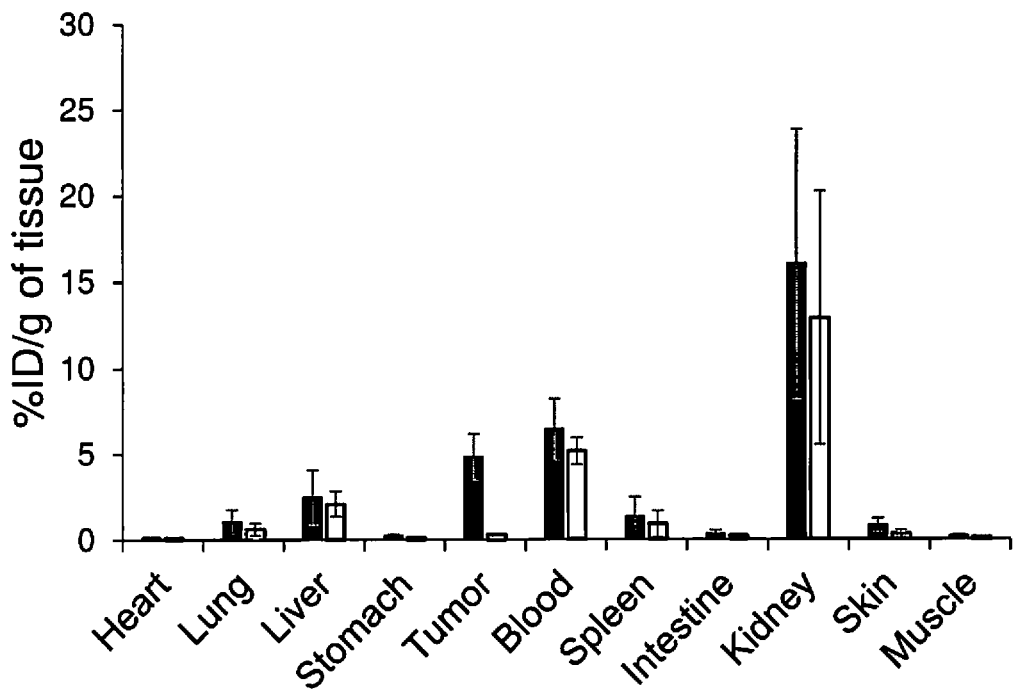
FIG. 8B: (□) Competition; (■) L2-PEG$_{36}$-EC20.
Figure 8C:
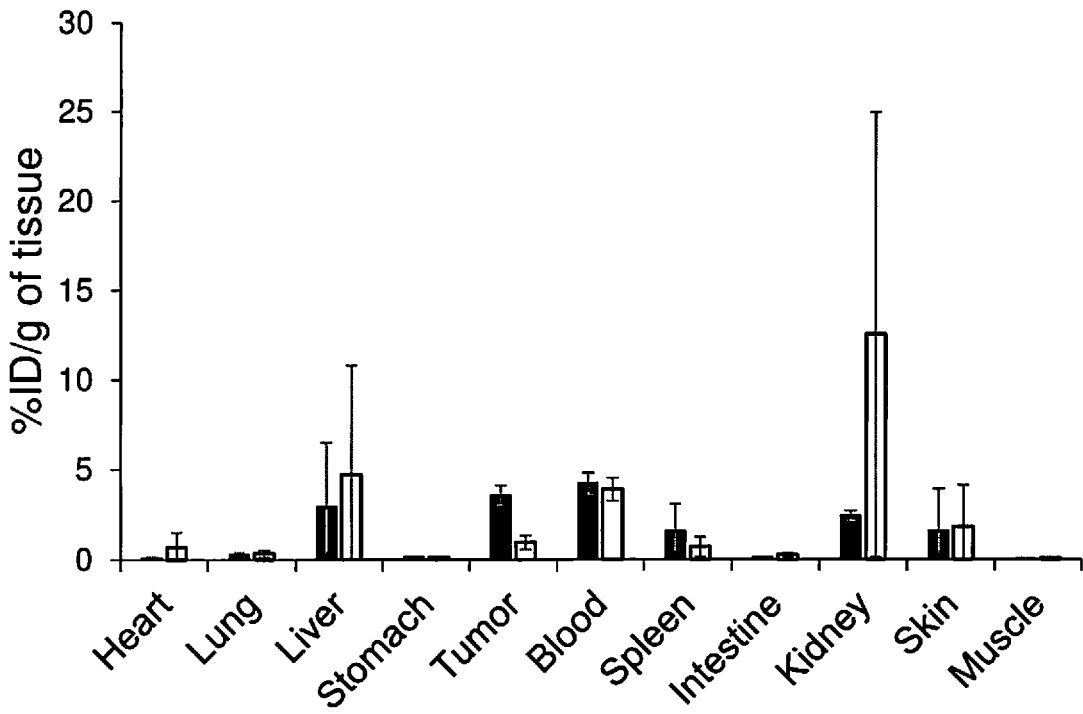
FIG. 8C: (□) Competition; (■) L2-Pro$_3$-PEG12-EC20.
Figure 8D:
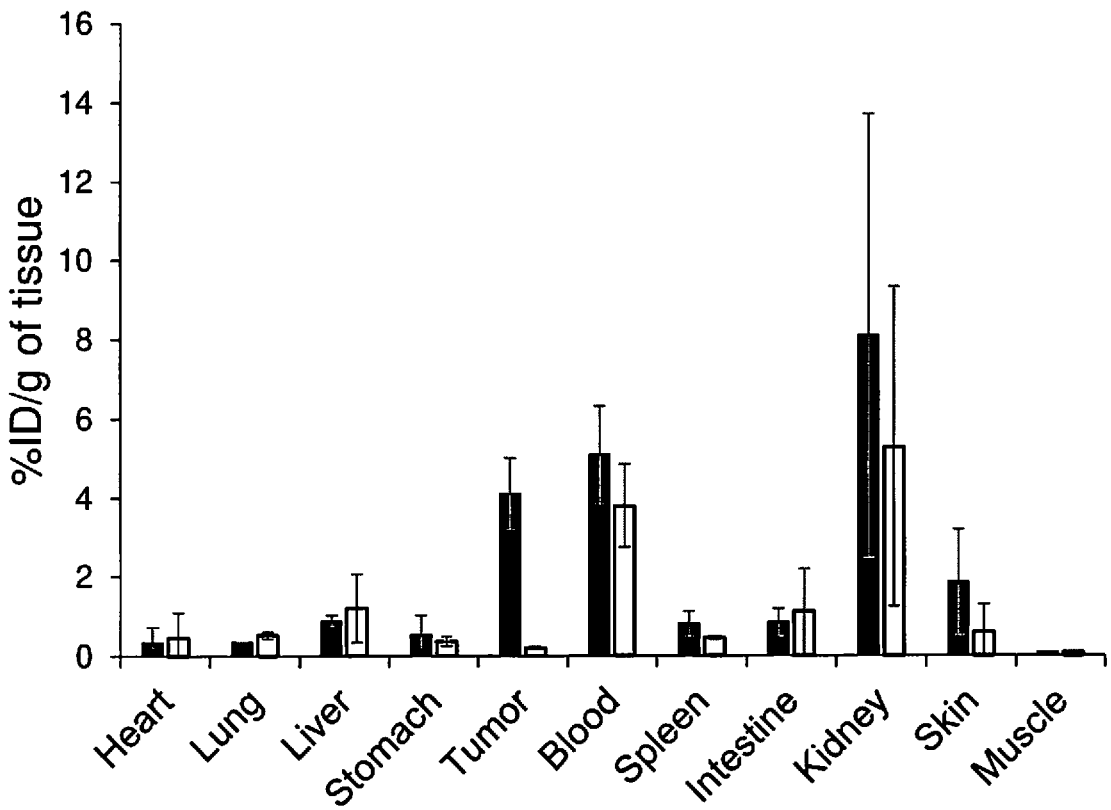
FIG. 8D: (□) Competition; (■)L3-PEG$_{12}$-EC20.

Three mice bearing HT-29 xenografts were administered 10 nmol of conjugate via tail vein injection while an additional three mice also received 100-fold excess unconjugated inhibitor. A single mouse from each of the two groups was sacrificed for whole animal imaging and tissue/organ biodistribution analysis at 4, 9 and 24 hours post injection. As shown in FIGS. 5A, 6A and 7A when the kidneys were shielded, radioactive intensity was localized to the tumor with relative average intensities of ~1300, 750 and 350 at 4, 9 and 24 hours, respectively. Importantly, all mice concurrently injected with 100-fold excess unconjugated inhibitor did not exhibit any intensity in the tumor, indicative of receptor-dependent binding/uptake. Overall, the biodistribution (FIGS. 5B, 6B and 7B) also shows a decrease in the amount of conjugate in all tissues over time with clearance in the liver and spleen particularly quickly between the 4 and 9 hour timepoints.

Example 11

Biodistribution of $^{99m}$Tc Conjugates

To determine the uptake of the various $^{99m}$Tc-bound conjugates in CA IX expressing tumors, 10 nmol of each of the four conjugates L2-PEG$_{12}$-EC20, L2-PEG$_{36}$-EC20, L2-Pro$_3$-PEG$_{12}$-EC20 and L3-PEG$_{12}$-EC20 were injected into mice bearing HT-29 xenografts in the presence or absence 100-fold excess of the appropriate unconjugated CA IX inhibitor L2 or L3. These experiments were conducted according to the methodology described in Example 7. As shown in FIGS. 8A, 8B, 8C and 8D, the tumor was the only tissue that showed lower binding of all four conjugates when competing inhibitor was co-administered, indicating that no other tissue binding was CA IX receptor mediated. Overall, the four conjugates exhibited fairly similar biodistribution profiles. However, L2-PEG$_{12}$-EC20 did show a somewhat lower overall percentage of the injected dose being retained in the tissues. Otherwise, all conjugates appear to not be rapidly cleared from the bloodstream as measurable activity is still apparent in the blood after 4 hours. High activity located in the kidneys is most likely due to excretion, suggesting the renal system being the primary excretion route. However, the liver may also remove a portion of these conjugates from the bloodstream as some activity was also present in the liver.

Example 12

In Vitro Cytotoxicity of L2-Tubulysin B

Figure 9:
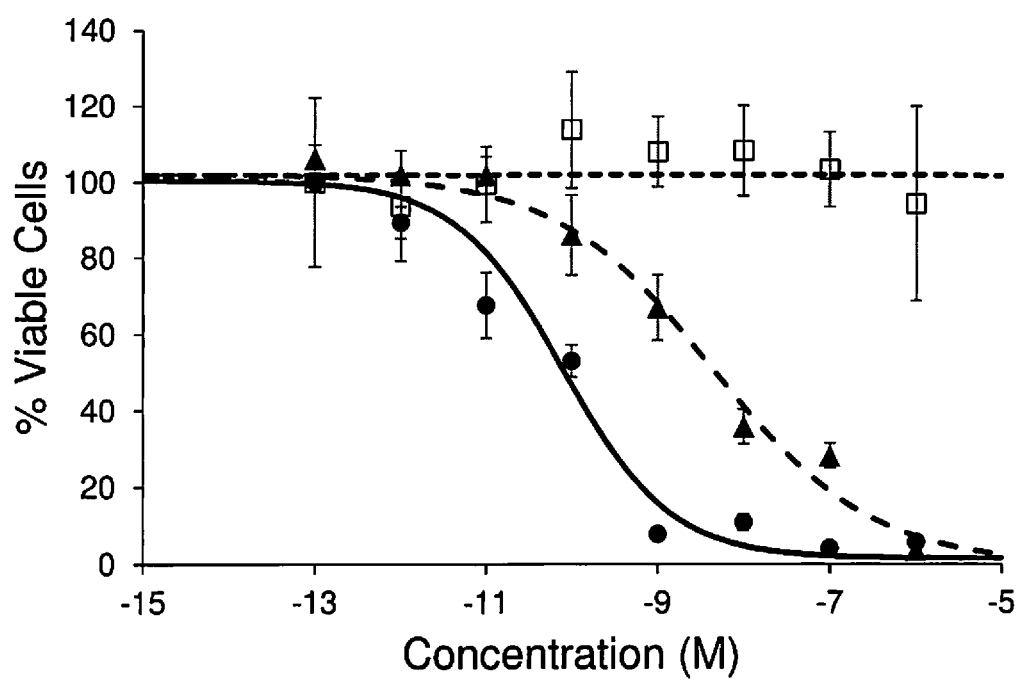
FIG. 9 shows in vitro HT-29 cytotoxicity and in vivo maximum tolerated dose of L2-Tubulysin B. Various concentrations of L2-Tubulysin B with or without 100-fold excess CA IX ligand L2 were incubated with HT-29 cells for 1 hour. After washing, the cells were incubated for 24 hours and their viability was determined via $^3$H-thymidine uptake.

HT-29 cells were seeded on amine-coated 24-well plates and allowed to form monolayers. The spent medium in each well was replaced with fresh medium (0.5 mL) containing various concentrations of Tubulysin B or L2-Tubulysin B in the presence or absence of 100-fold excess CA IX inhibitor L2. After incubating for 2 h at 37° C., cells were rinsed 3 times with fresh medium and then incubated an additional 66 h at 37° C. in fresh medium. Spent medium in each well was again replaced with fresh medium (0.5 mL) containing $^3$H-thymidine (1 µCi/ml) and the cells were incubated for an additional 4 h. After washing the cells 3 times with medium, they were dissolved in 0.5 mL of 0.25 M NaOH. Thymidine incorporation was then determined by counting cell-associated radioactivity using a scintillation counter (Packard, Packard Instrument Company). The IC$_{50}$ value was derived from a plot of the percent of $^3$H-thymidine incorporation versus log concentration using Graph Pad Prism 4 and TableCurve 2D software. Results are shown in FIG. 9 As shown in FIG. 9, the IC$_{50}$ for the conjugate was 4.4 nM while the unconjugated Tubulysin B was 0.08 nM. When the conjugate was competed with 100-fold excess of the unconjugated inhibitor, the cytotoxic effect was completely abrogated, demonstrating the requirement of receptor binding for cytotoxicity.

Maximum tolerated dose. Various concentrations of L2-Tubulysin B were administered to male nu/nu mice thrice weekly via tail vein injection. Visibly sick mice were recorded and if necessary euthanized before the end of the experiment. Three treatment groups consisting of three mice per group were treated with increasing concentrations of CA IX-Tubulysin B. As shown in Table 2, no adverse events were identified when 1 µmol/kg CA IX-Tubulysin B was administered. However, at the highest dose, 5 mol/kg, all mice showed signs of toxicity. Therefore, a dose of 2 µmol/kg was used for further in vivo efficacy studies.

TABLE 2

| Dose (µmol/kg) | Healthy | Sick | Euthanized |
|---|---|---|---|
| 1 | 3 | 0 | 0 |
| 3 | 2 | 1 | 0 |
| 5 | 0 | 1 | 2 |

Figure 10A:
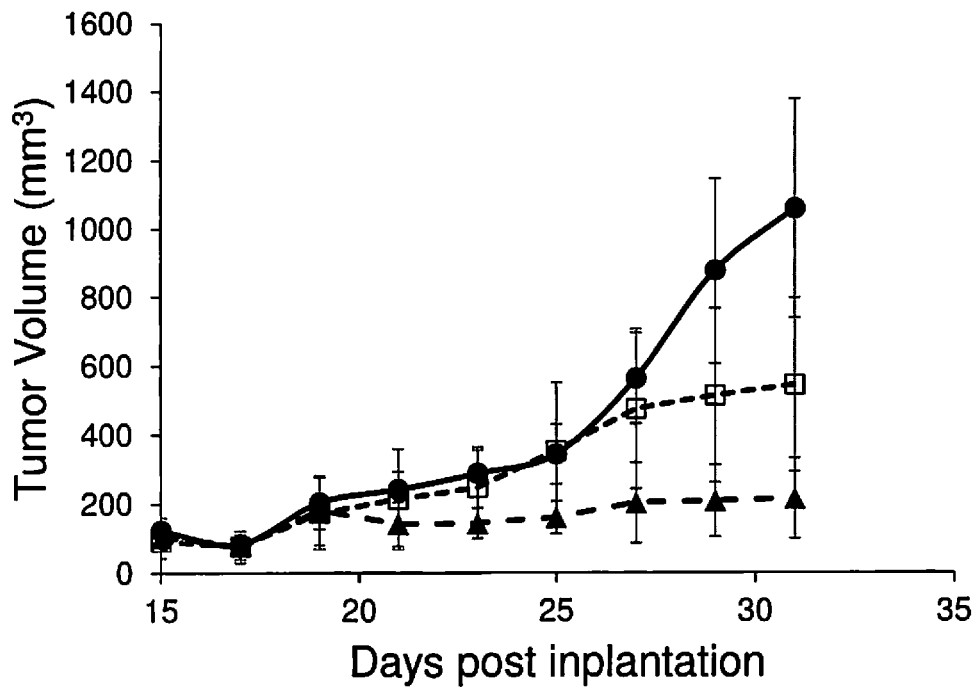
FIG. 10A: (●) PBS Control, (▲) L2-Tubulysin B, (□) Competition.
Figure 10B:
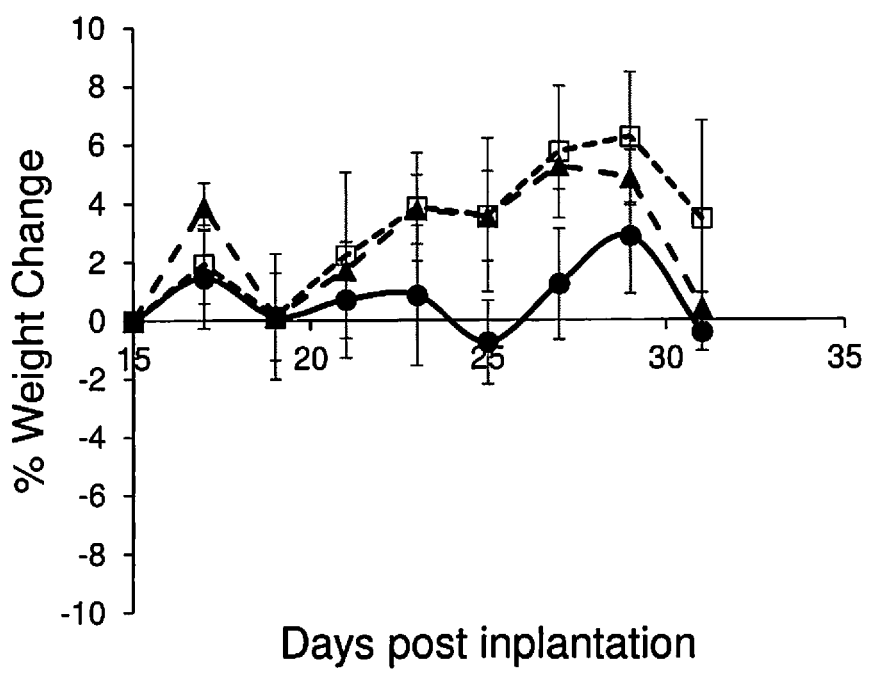
FIG. 10B: (●) PBS Control, (▲) L2-Tubulysin B, (□) Competition.
Figure 11A:
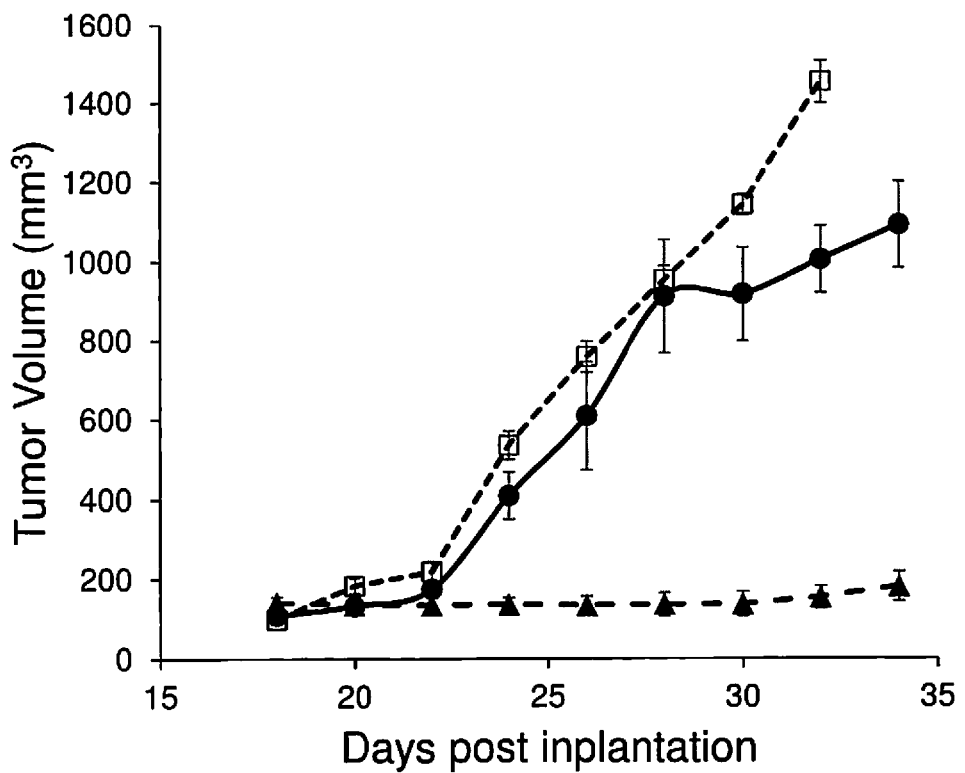
FIG. 11A: (●) PBS Control, (▲) L2-Tubulysin B, (□) Competition.
Figure 11B:
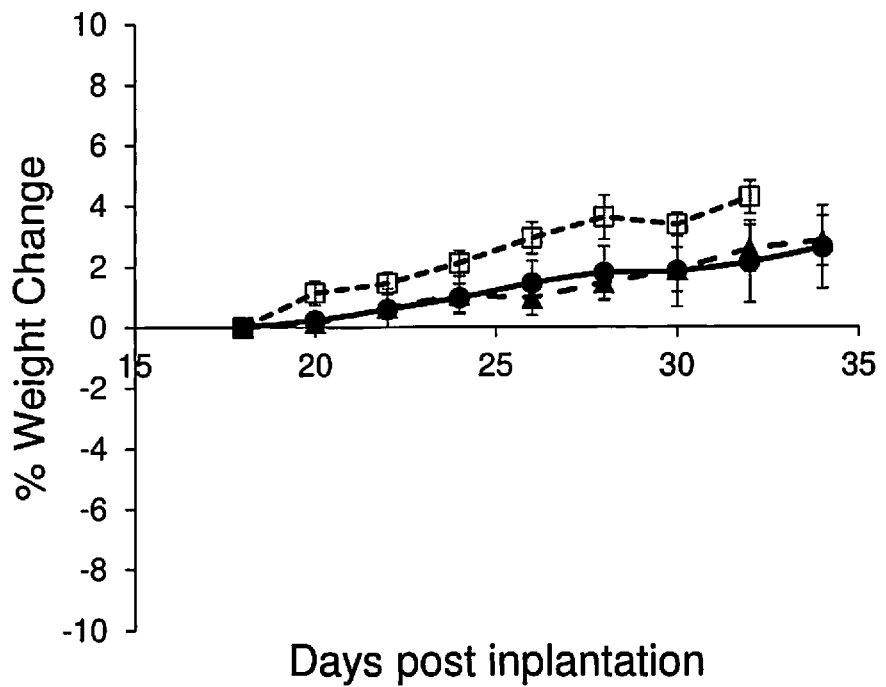
FIG. 11B: (●) PBS Control, (▲) L2-Tubulysin B, (□) Competition.

In vivo xenograft tumor efficacy of L2-Tubulysin B. HT29 cells (5.0×10⁶) were injected into the shoulders of 5-6 week old female nu/nu mice. Tumors were measured in two perpendicular directions thrice weekly with vernier calipers and their volumes were calculated as 0.5×L×W², where L is the longest axis (in millimeters), and W is the axis perpendicular to L (in millimeters). Dosing of L2-Tubulysin B in the presence or absence of 100-fold excess CA IX inhibitor L2 was initiated when the subcutaneous tumors reached ~100 mm³ in volume. Dosing solutions were prepared in saline and filtered through a 0.22 µm filter. Solutions were administered via tail vein injection or intraperitoneally. Each mouse received 2 µmol/kg L2-Tubulysin B per injection. Injections were given thrice weekly for 3 weeks and the mice were weighed concurrently. Results are shown in FIG. 10 and FIG. 11. As shown in FIG. 10A and FIG. 11A, both administration routes essentially halted tumor growth. Importantly, when the cytotoxic conjugate was administered in conjunction with 100-fold excess CA IX inhibitor L2, the growth of the tumors was similar to the control group, further demonstrating the receptor-dependence on activity. In all cases, no gross toxicity was observed and no loss of weight was observed at this dosing level (see FIG. 10B and FIG. 11B).

Example 13

Fluorescence Imaging and Biodistribution of Hypoxyfluor

Using a 25-gauge needle, six-week-old female nu/nu mice were inoculated subcutaneously in their shoulders with HT-29 cells in RPMI1640 medium (5.0×10⁶ cells per mouse). Tumor growth was measured in 2 perpendicular directions every 2 days with a caliper. Tumor volumes were calculated using the formula 0.5×L×W², where L is the measurement of the longest axis and W is the measurement of the axis perpendicular to L. Tumor bearing mice were treated via tail vein injection with different concentrations of Hypoxyfluor in the presence or absence of 100-fold CA IX ligand to block all unoccupied CA IX binding sites. Mice were imaged 4 hours post injection using a Caliper IVIS Lumina II Imaging station coupled to an ISOON5160 Andor Nikon camera equipped with Living Image Software Version 4.0. Image acquisition settings were as follows: lamp level, high; excitation, 745 nM; emission, ICG; epi illumination; binning (M) 4; FOV, 12.5; f-stop, 4; acquisition time, 1 s.

Figure 12A:
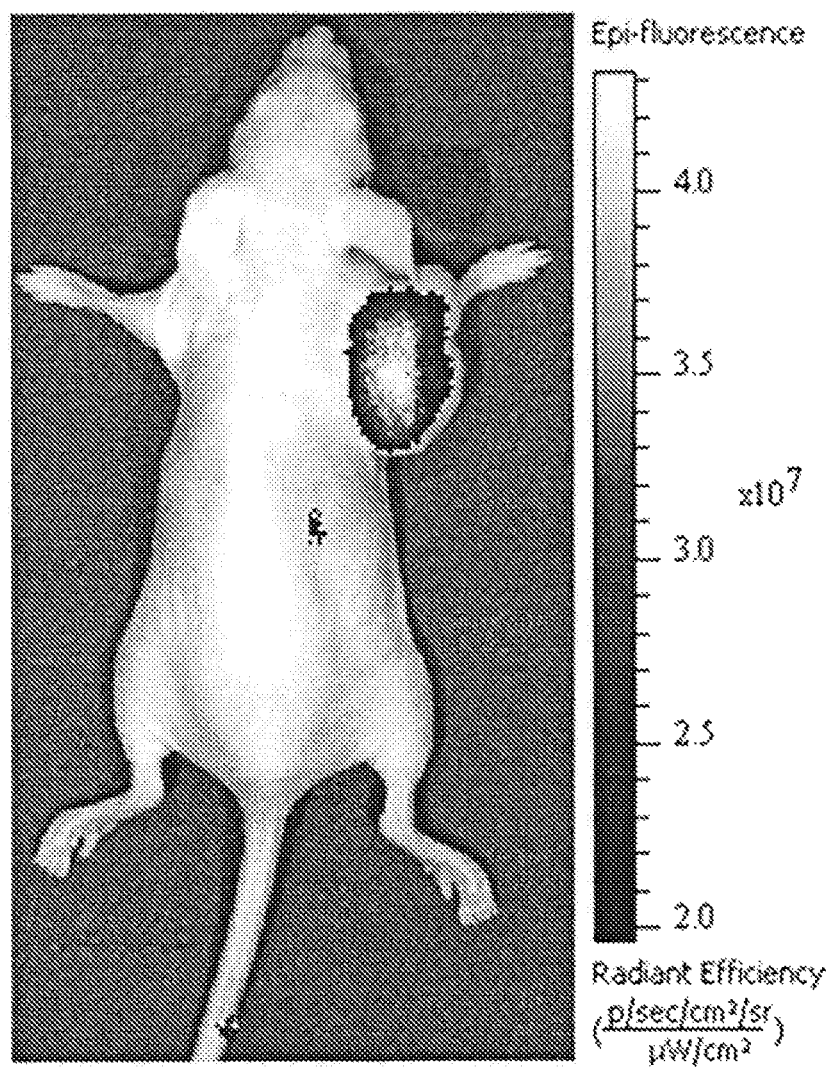
FIG. 12 shows representative images of Hypoxyfluor treated HT-29 tumor bearing mice. Mice bearing HT-29 tumors were injected via tail vein with 4 nmol Hypoxyfluor alone or in combination with 100-fold excess CA IX inhibitor. Fluorescence images were acquired 4 hours post injection.
Figure 12B:
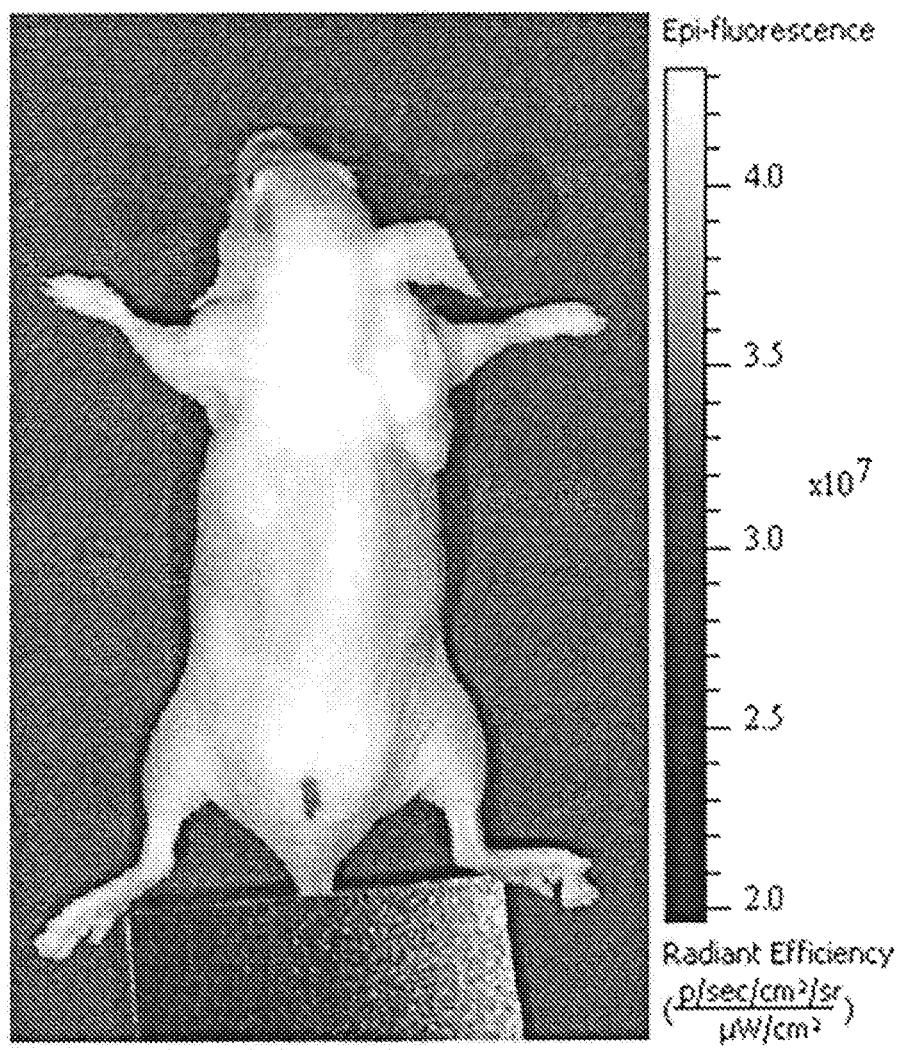

Results: Mice bearing HT-29 tumor xenografts were injected via tail vein with 4 nmol of Hypoxyfluor and imaged 4 hours later. As shown in FIG. 12, Hypoxyfluor conjugate fluorescence was predominately detected in the tumor (See FIG. 12A). Moreover, when 400 nmol of the CA IX ligand was injected together with the 4 nmol of Hypoxyfluor, no fluorescent signal could be detected in the whole animal images, suggesting that tumor cell uptake was also CA IX receptor specific in vivo (See FIG. 12B).

Figure 13A:
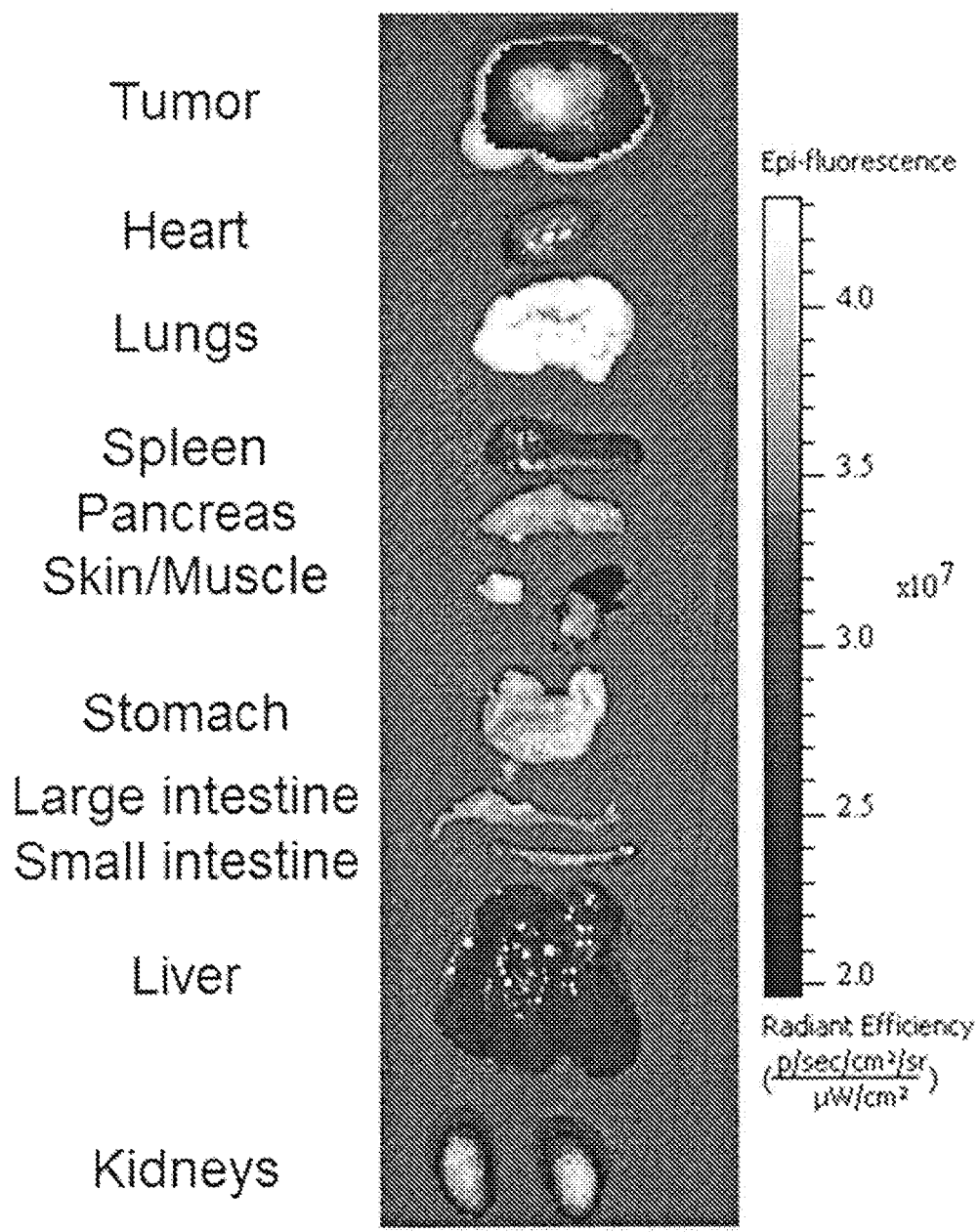
FIG. 13 shows accumulation of Hypoxyfluor in internal tissues and organs of mice from FIG. 12. Tissues and organs were excised after whole animal imaging and the fluorescence images of the isolated tissues were acquired.
Figure 13B:
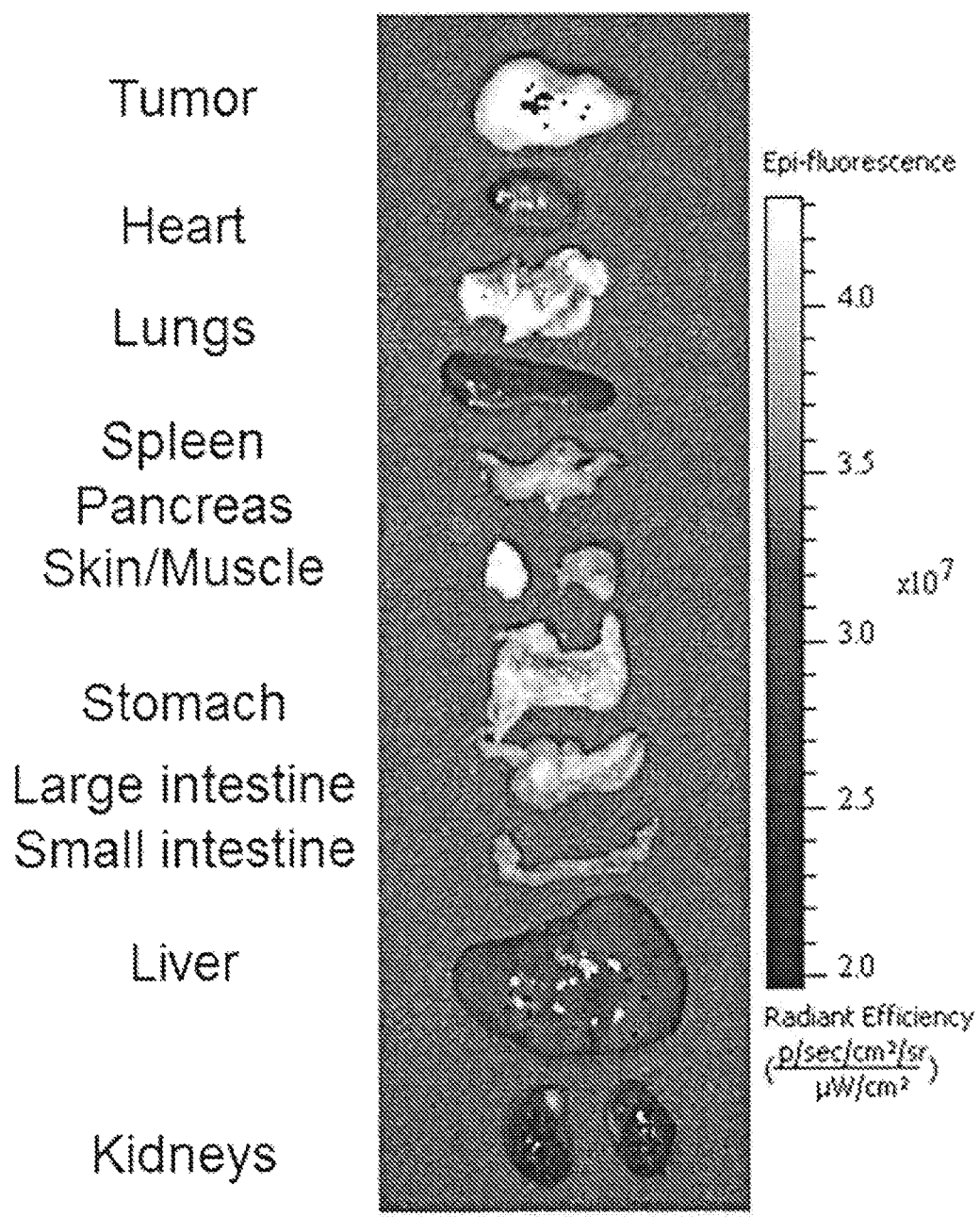

Major organs/tissues were removed and examined for fluorescence 4 hours post-injection. As shown in FIG. 13, fluorescence was apparent in the tumor and kidneys with very little or no signal observed in any other tissues. Similar to whole animal images, little fluorescence was observed in any tissues when Hypoxyfluor uptake was measured upon concurrent injection of excess unconjugated ligand (See FIG. 13A v FIG. 13B).

Figure 14A:
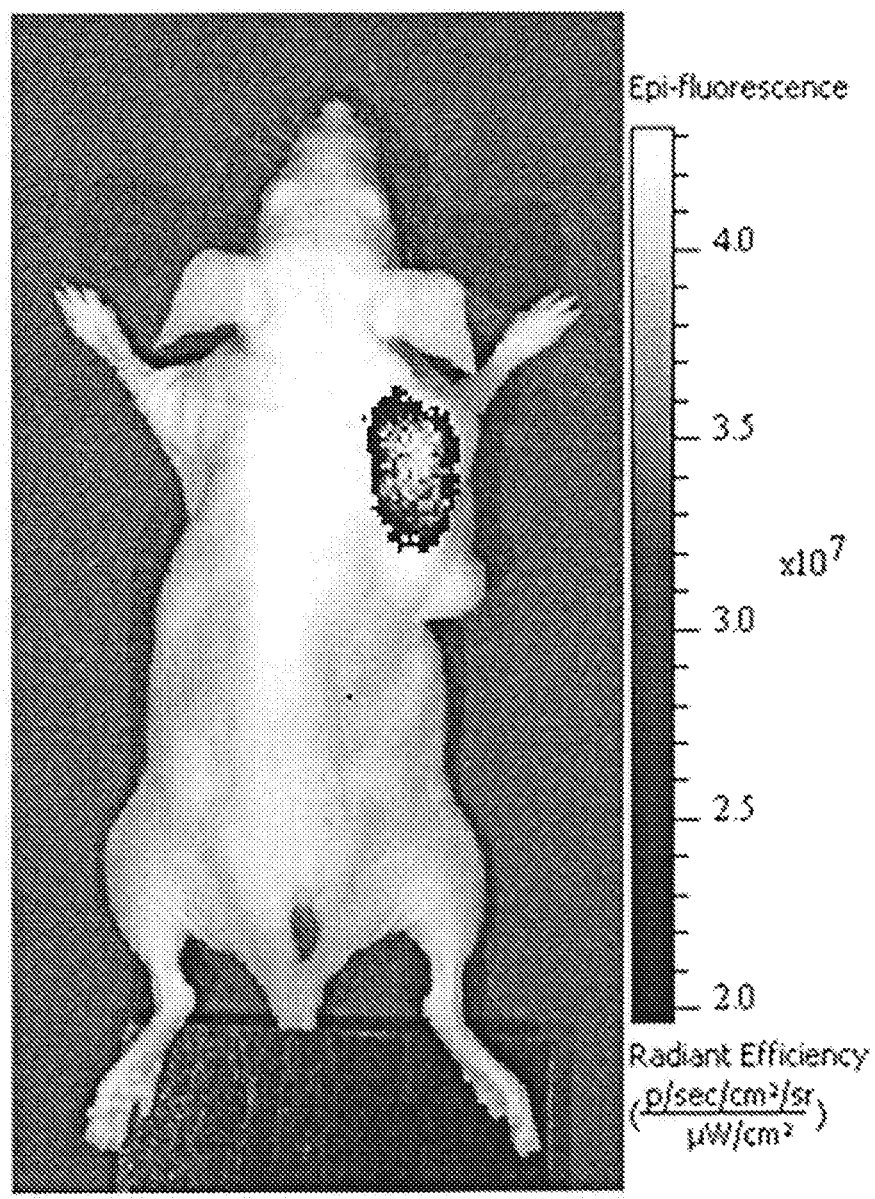
FIG. 14 shows representative in vivo images of HT-29 tumor-bearing mice treated with increasing doses of Hypoxyfluor. Mice bearing HT-29 tumors were injected via tail vein with the indicated concentrations of Hypoxyfluor and fluorescence images were acquired 4 hours post injection.
Figure 14B:
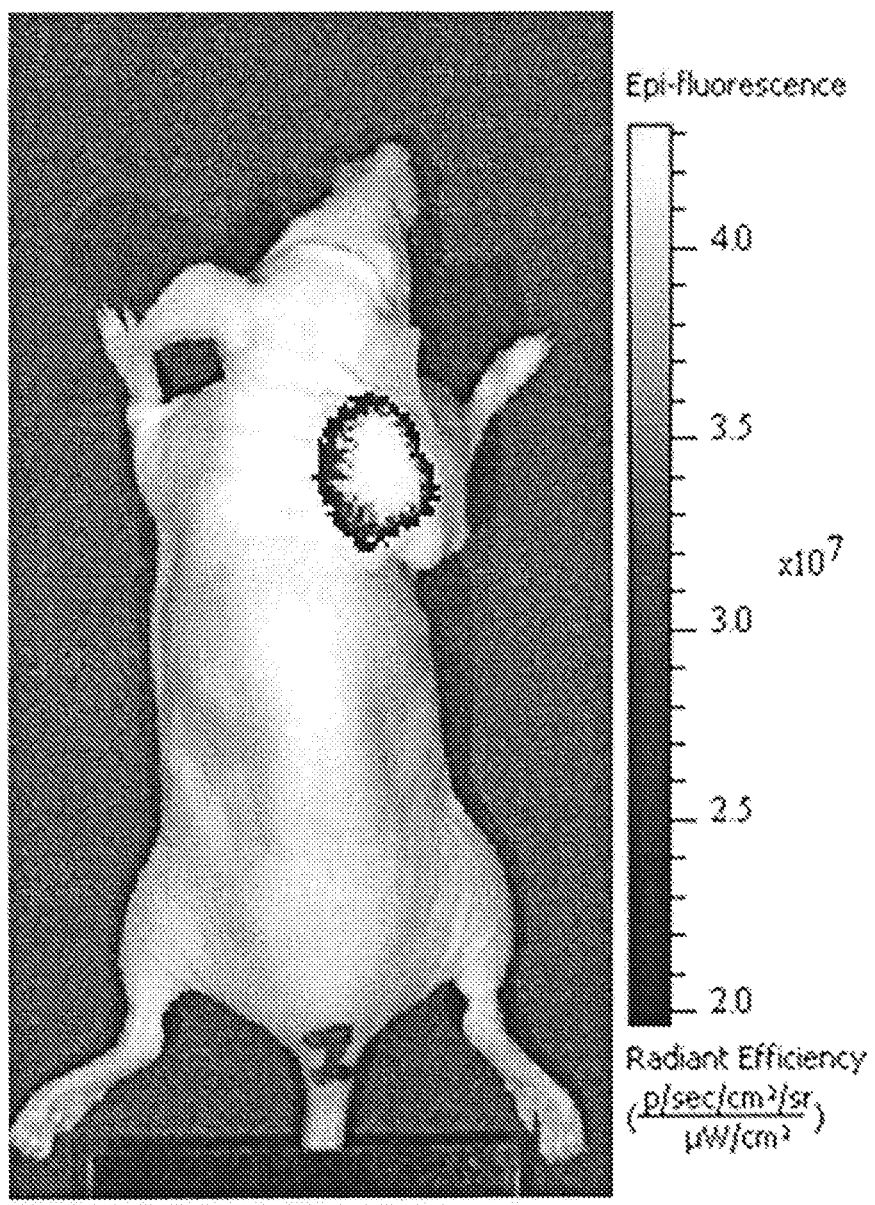
Figure 14C:
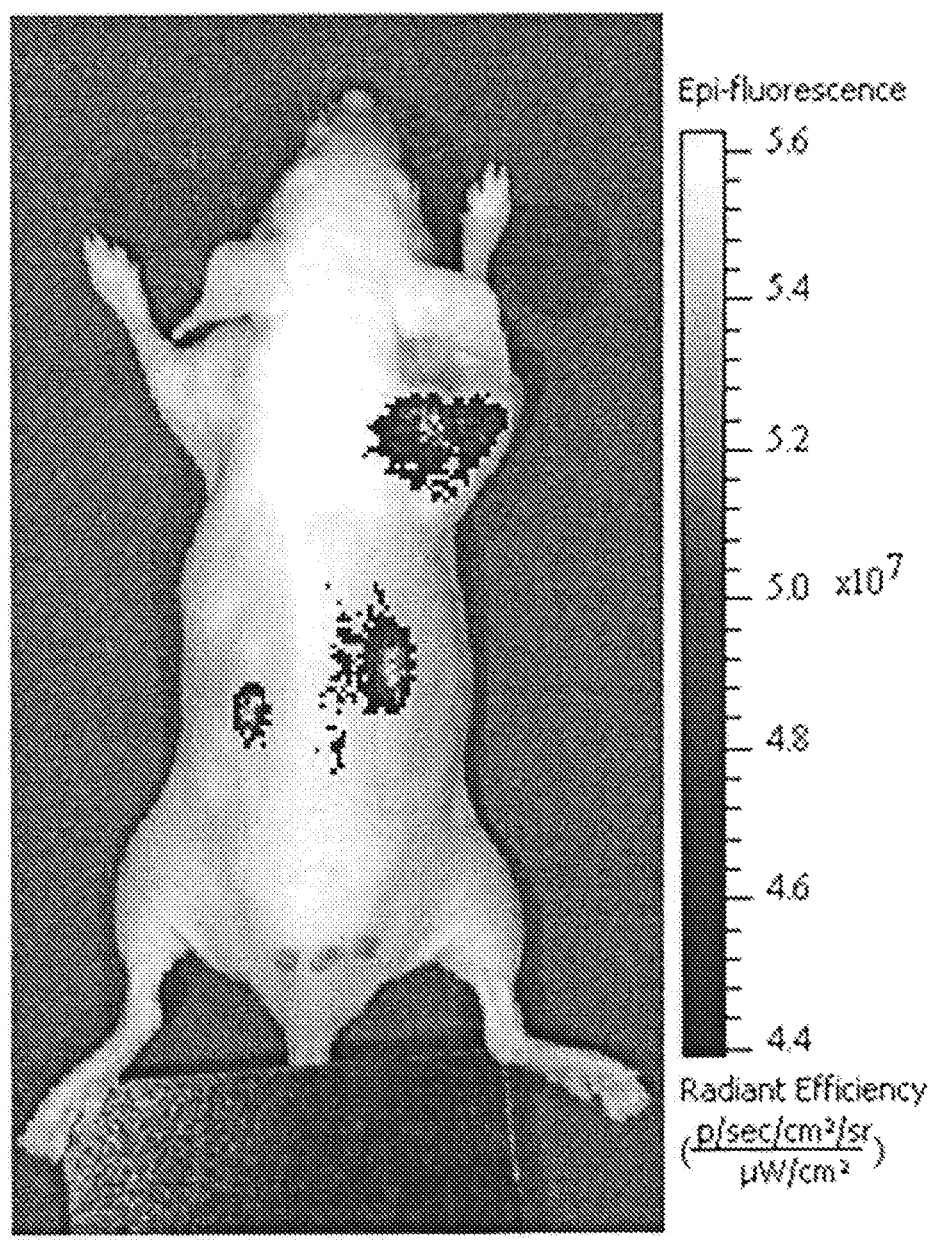
Figure 15A:
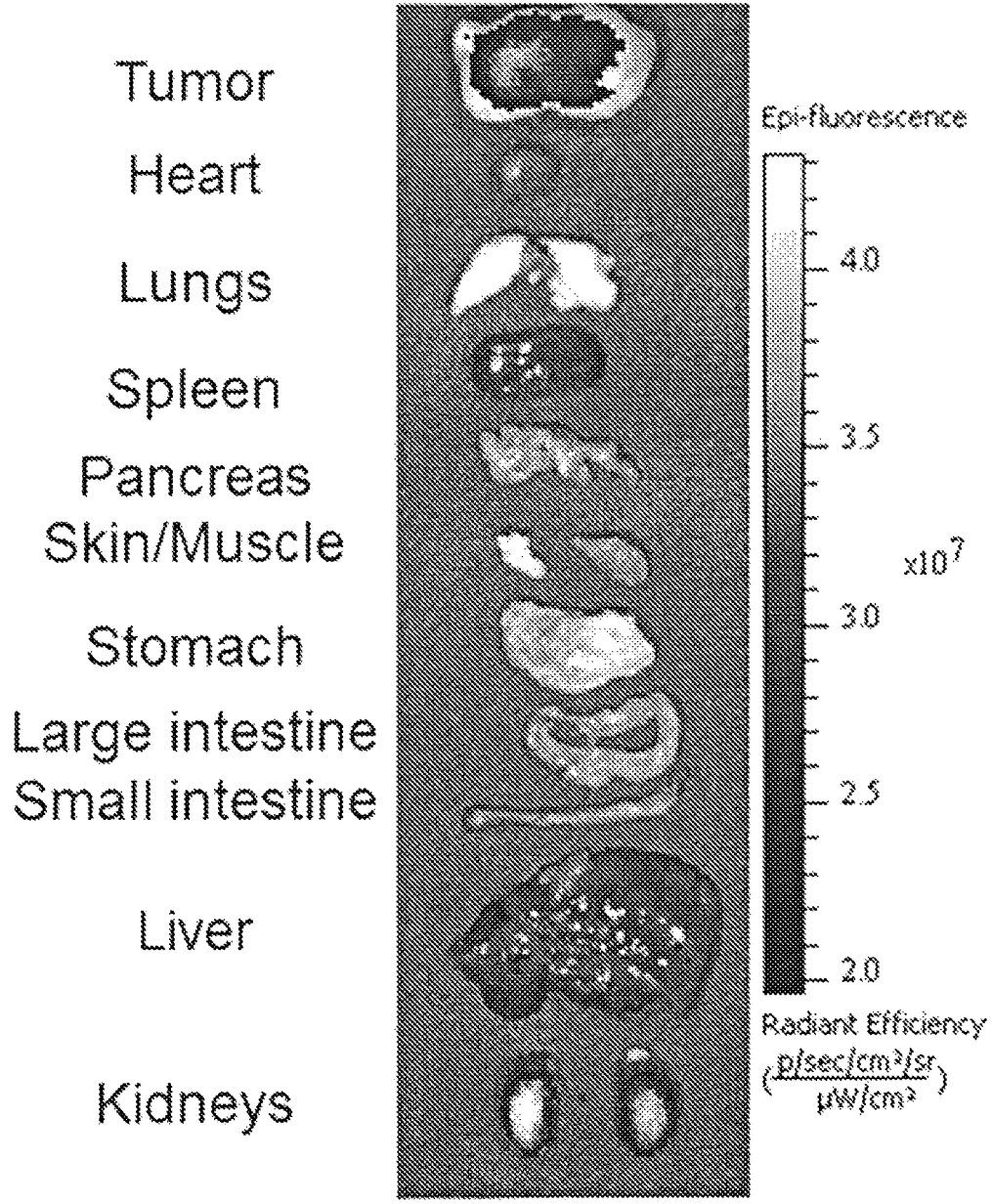
FIG. 15 shows accumulation of Hypoxyfluor in internal tissues and organs of mice from FIG. 14. Tissues and organs were excised after whole animal imaging and the fluorescence images of the isolated tissues were acquired.
Figure 15B:
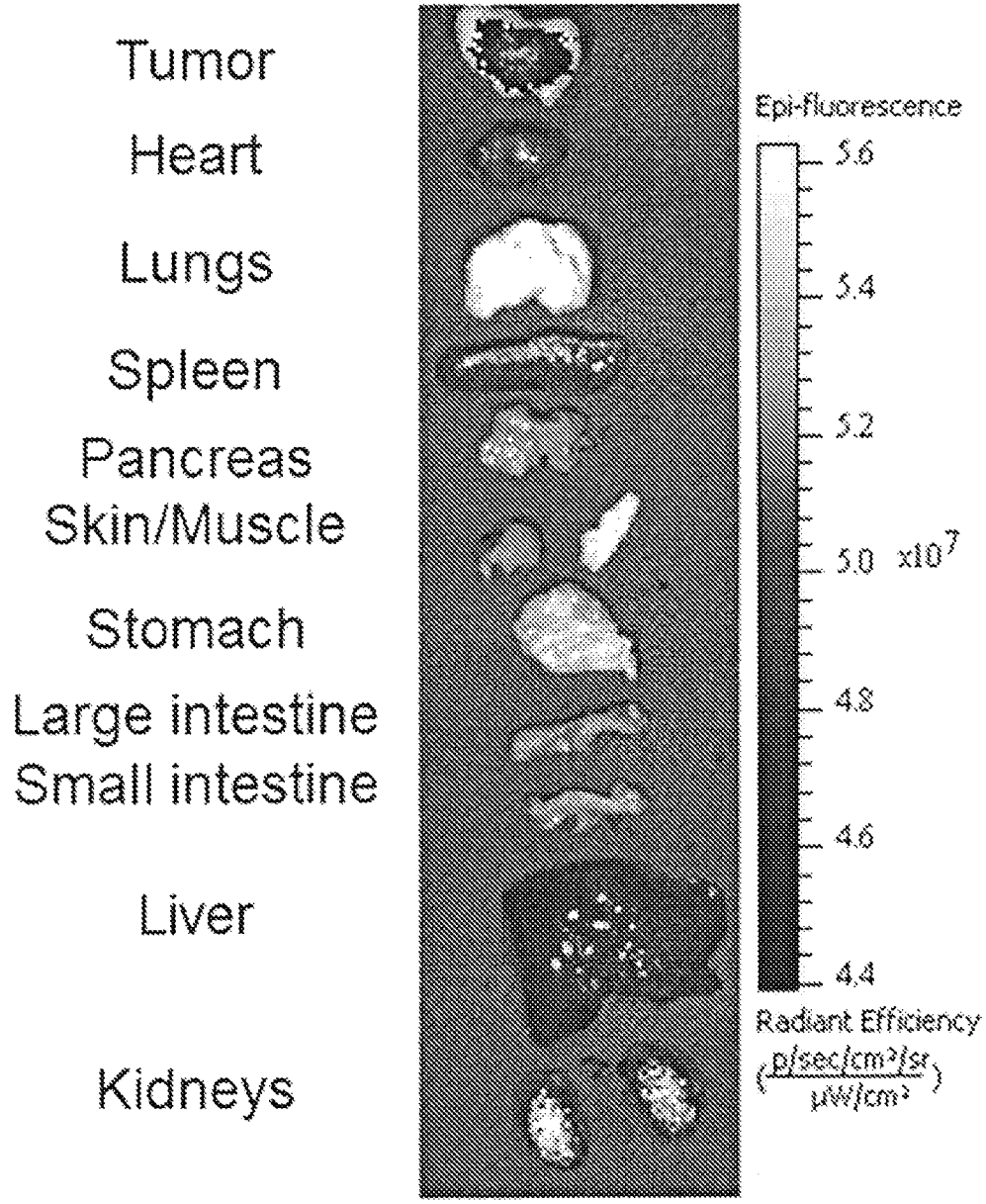
Figure 15C:
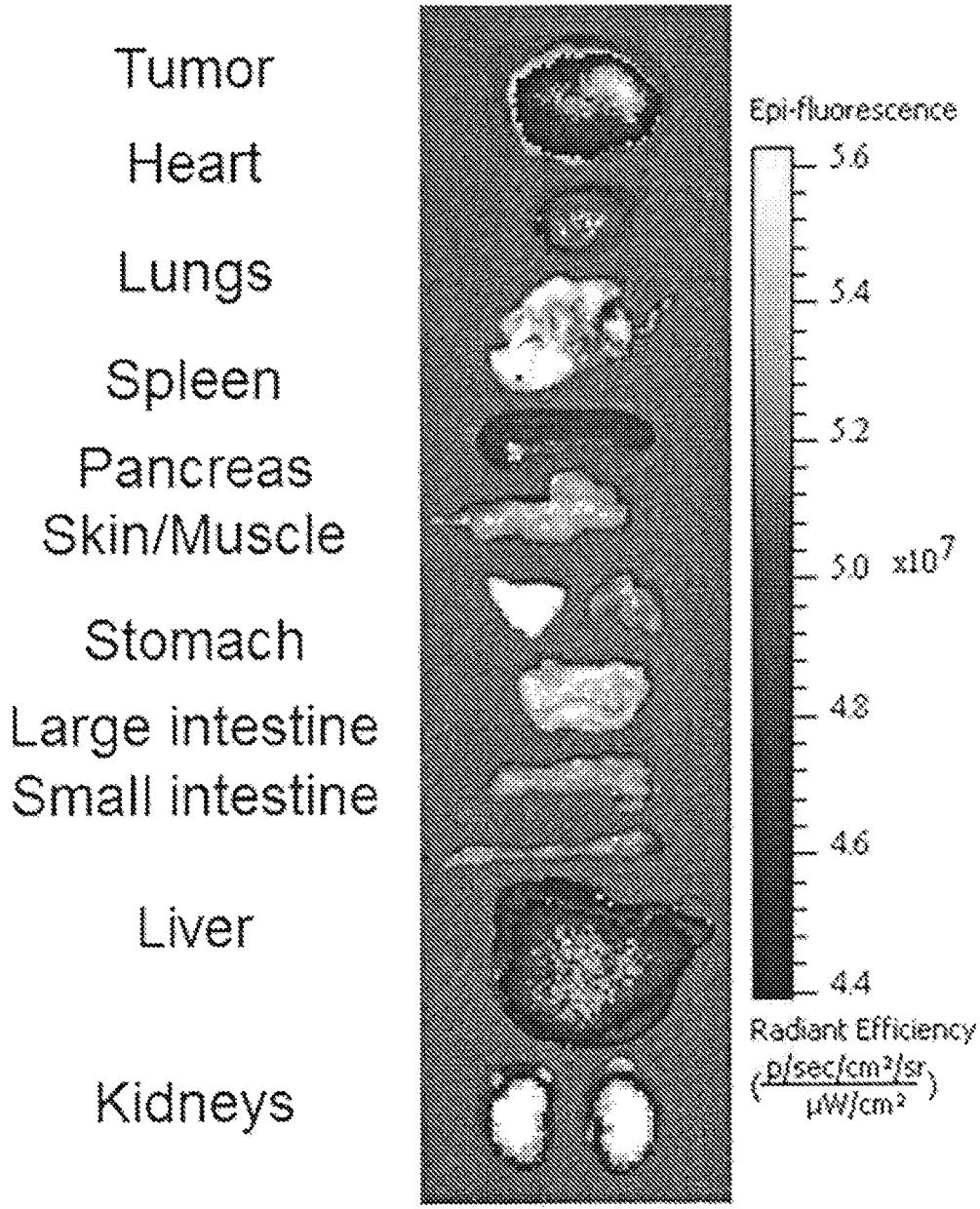

A dose escalation study of Hypoxyfluor was performed, where 3, 13 and 40 nmol of Hypoxyfluor conjugate were injected via tail vein in HT-29 tumor-bearing mice. As shown in FIG. 14, fluorescence was restricted to the tumor when low and intermediate doses were administered (See FIGS. 14A and 14B). In contrast, following injection of 40 nmol/mouse, nontumor associated fluorescence became apparent in whole body images (See FIG. 14C). When major organs and tissues were removed and imaged, additional fluorescence was seen in the liver at 40 nmol/mouse (See FIG. 15C), while no such fluorescence was observed at 3 nmol and 13 nmol (See FIGS. 15A and 15B). This result suggests that at high injection doses, Hypoxyfluor may be partially cleared through the liver.

What is claimed is:
1. A conjugate of the formula B-L-A, wherein B is a binding ligand of carbonic anhydrase IX (CA IX) having the formula

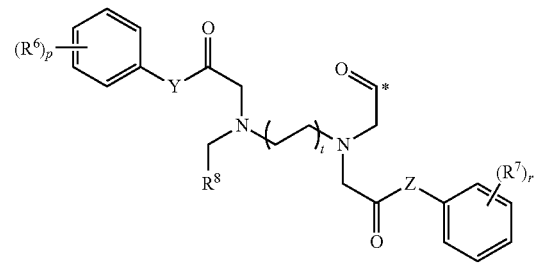

wherein
wherein each R⁶ and R⁷ is independently selected from the group consisting of H, OR⁹, —OC(O)R⁹, —OC(O)NR⁹R¹⁰, —OS(O)R⁹, —OS(O)₂R⁹, —SR⁹, —S(O)R⁹, —S(O)₂R⁹, —S(O)NR⁹R¹⁰, S(O)₂NR⁹R¹⁰, —OS(O)NR⁹R¹⁰, —OS(O)₂NR⁹R¹⁰, —NR⁹R¹⁰, —NR⁹C(O)R¹⁰, —NR⁹C(O)OR¹⁰, —NR⁹C(O)NR⁹R¹⁰, —NR⁹S(O)R¹⁰, —NR⁹S(O)₂R¹⁰, —NR⁹S(O)NR⁹R¹⁰, —NR⁹S(O)₂NR⁹R¹⁰, —C(O)R⁹, —C(O)OR⁹, and —C(O)NR⁹R¹⁰;
R⁸ is selected from the group consisting of H, C₁-C₆ alkyl, C₂-C₆ alkenyl, and C₂-C₆ alkynyl, —C(O)R¹¹, —C(O)OR¹¹, and —C(O)NR¹¹R¹²;
Y is —NR⁹'—;
Z is —NR¹⁰'—;
each R⁹, R¹⁰, R⁹', R¹⁰' R¹¹ and R¹² is independently selected from the group consisting of H, C₁-C₆ alkyl, C₂-C₆ alkenyl, and C₂-C₆ alkynyl;
p is an integer from 1 to 4;
r is an integer from 0 to 4;
t is an integer from 1 to 3; and
* represents a covalent bond to L;
wherein L is a linker of 2 to 100 atoms in length covalently attached to B and A, and
wherein A is a therapeutic agent, or an imaging agent selected from a rhodamine dye and a single-photon emission computed tomography (SPECT) imaging agent, and A is covalently attached to L.

2. The conjugate of claim 1, or a pharmaceutically acceptable salt thereof, wherein B is of the formula

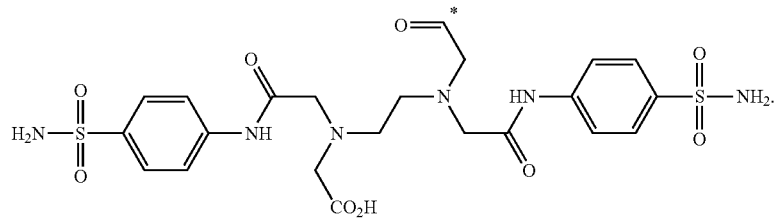 [SMILES: NS(=O)(=O)c1ccc(NC(=O)CN(CC=O)CCN(CC(=O)O)CC(=O)Nc2ccc(S(N)(=O)=O)cc2)cc1]

3. The conjugate of claim 1, or a pharmaceutically acceptable salt thereof, wherein L is a linker of 2 to 100 atoms in length covalently attached to B and A and comprises a portion selected from the group consisting of —C(O)(C$_1$-C$_{12}$ alkyl)C(O)—, —NH—C$_1$-C$_{12}$ alkyl-NH—, —N(C$_1$-C$_6$ alkyl)-C$_1$-C$_{12}$ alkyl-N(C$_1$-C$_6$ alkyl)-, —C(O)CH$_2$CH$_2$(OCH$_2$CH$_2$)$_q$NH—, —C(O)CH$_2$CH$_2$(OCH$_2$CH$_2$)$_{q1}$N(C$_1$-C$_6$ alkyl)-, —NH(CH$_2$CH$_2$O)$_{q2}$CH$_2$CH$_2$C(O)—, and —N(C$_1$-C$_6$ alkyl)(CH$_2$CH$_2$O)$_{q3}$CH$_2$CH$_2$C(O)—; wherein each of q, q1, q2 and q3 is an integer from 1 to 40.

4. The conjugate of claim 3, or a pharmaceutically acceptable salt thereof, comprising the formula

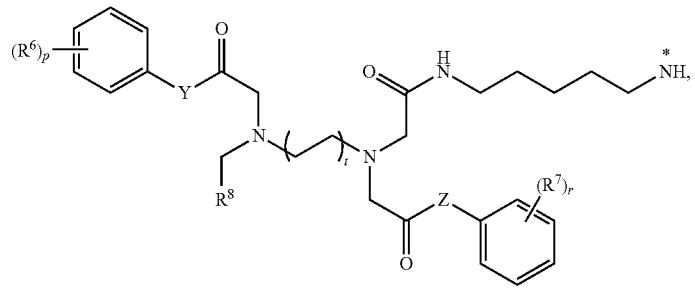

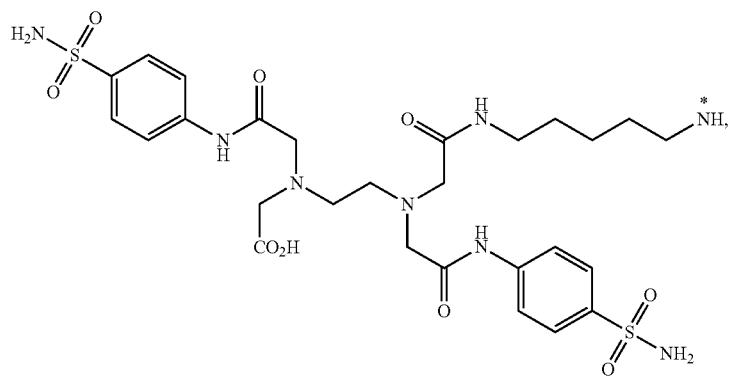

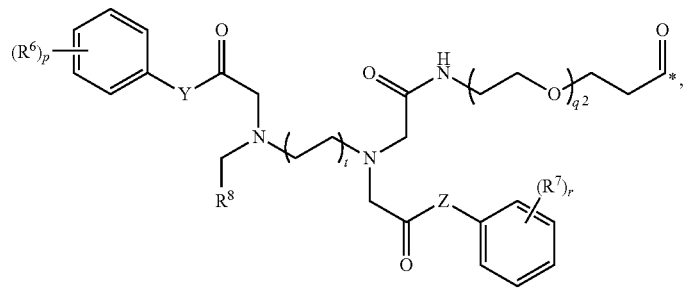

-continued

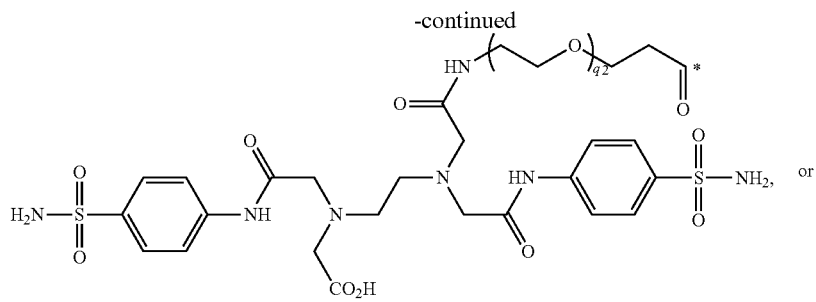

or

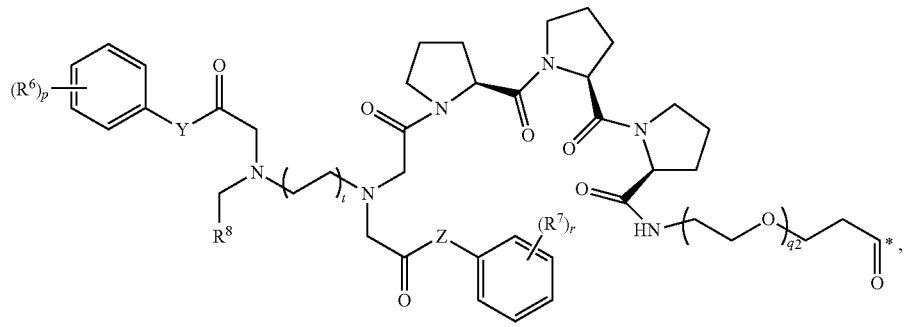

,

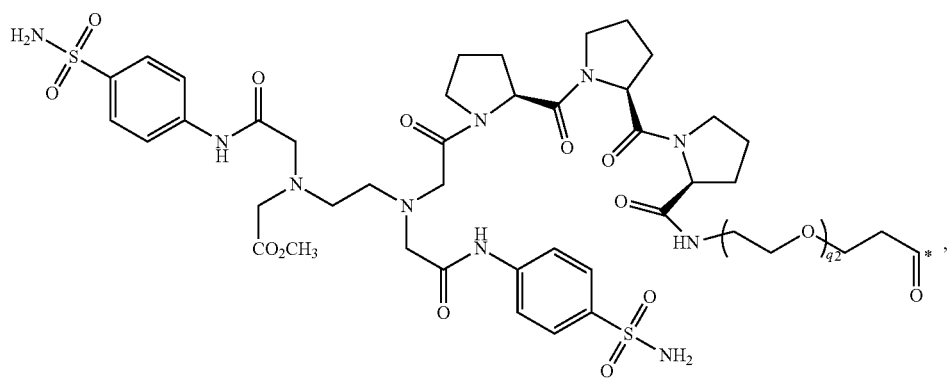

, wherein * represents a covalent bond to the rest of the conjugate and q and q2 are integers from 1 to 40.

5. The conjugate of claim 1, or a pharmaceutically acceptable salt thereof, wherein L is a linker —N(H)—$C_1$-$C_{12}$ alkyl—N(H)—C(O)—.

6. The conjugate of claim 1, or a pharmaceutically acceptable salt thereof, wherein L is a linker —N(H)—$C_1$-$C_{12}$ alkyl—N(H)—C(O)—and A is a rhodamine dye, or a SPECT imaging agent of the formula

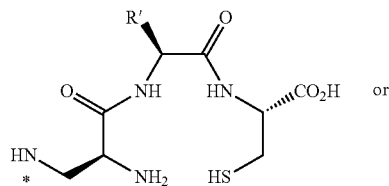

or

-continued

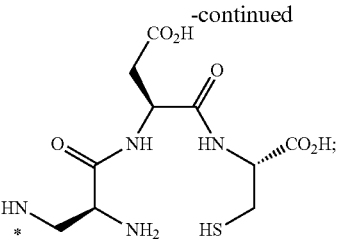

;

wherein R' is selected from the group consisting of H, is $C_1$-$C_6$ alkyl, amino-$C_1$-$C_6$ alkyl, carboxy-$C_1$-$C_6$ alkyl, hydroxyl-$C_1$-$C_6$ alkyl, $C_1$-$C_6$ heteroalkyl, $C_6$-$C_{10}$ aryl, $C_6$-$C_{10}$ aryl-$C_1$-$C_6$ alkyl $C_5$-$C_{10}$ heteroaryl-$C_1$-$C_6$ alkyl; and * represents a covalent bond to the rest of the conjugate.

7. The conjugate of claim 6, or a pharmaceutically acceptable salt thereof, wherein a radionuclei is bound to the conjugate.

8. The conjugate of claim 7, or a pharmaceutically acceptable salt thereof, wherein the radionuclei is selected from the group consisting of an isotope of gallium, an isotope of indium, an isotope of copper, an isotope of technetium, and an isotope of rhenium.

9. A conjugate selected from the group consisting of
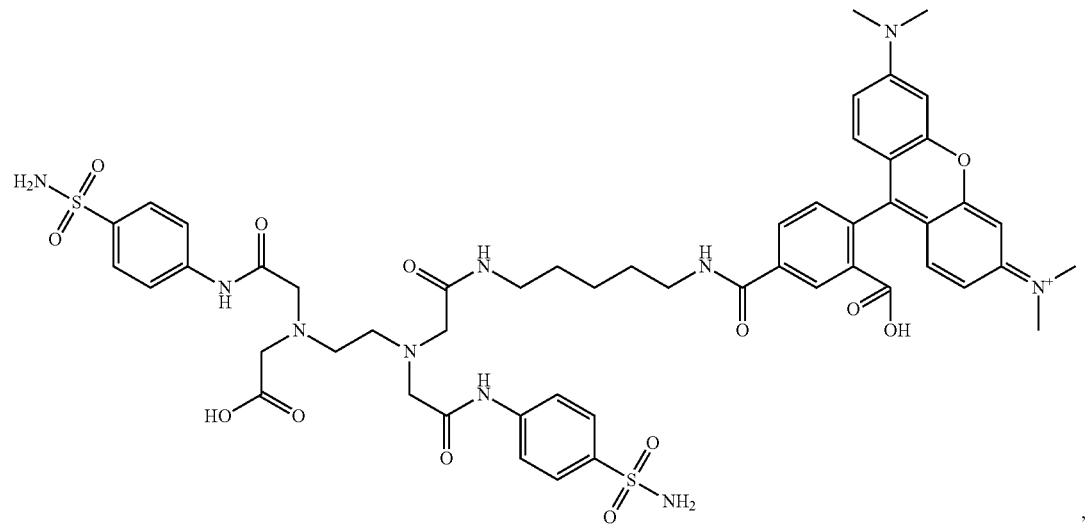
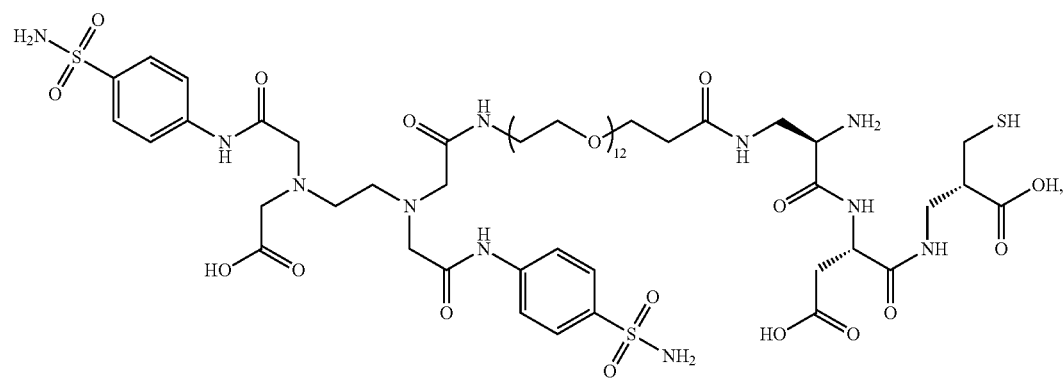
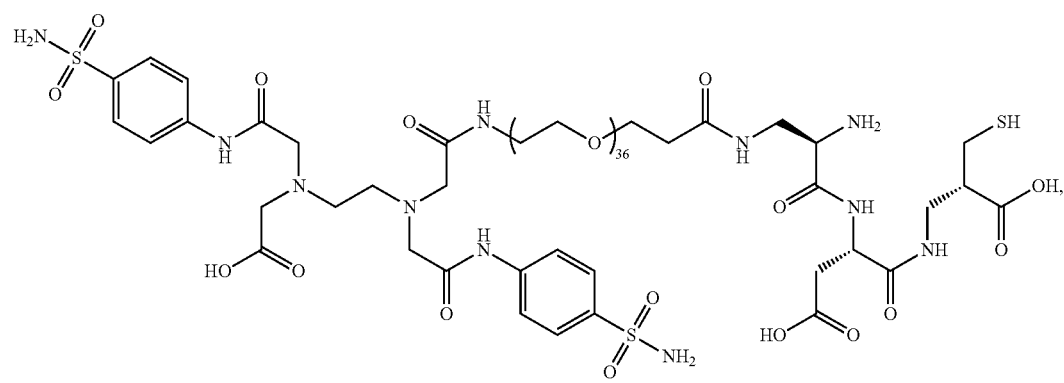
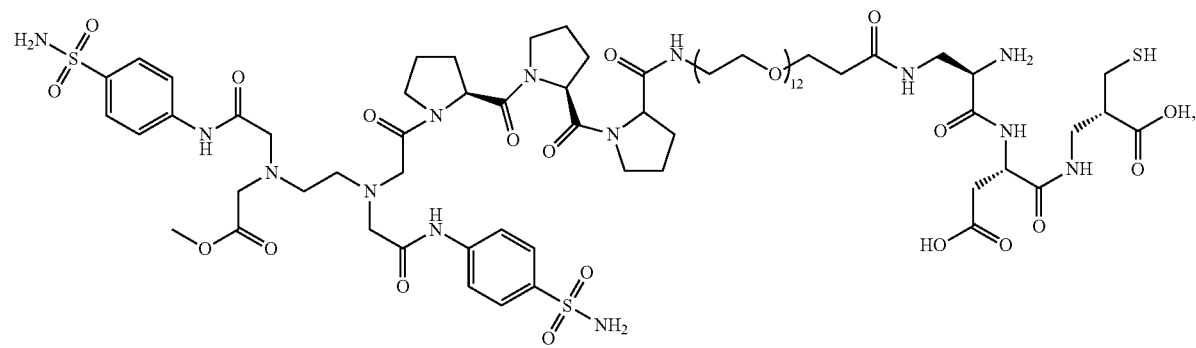

87
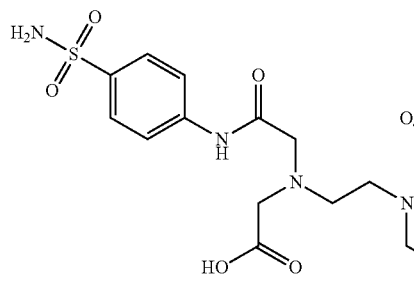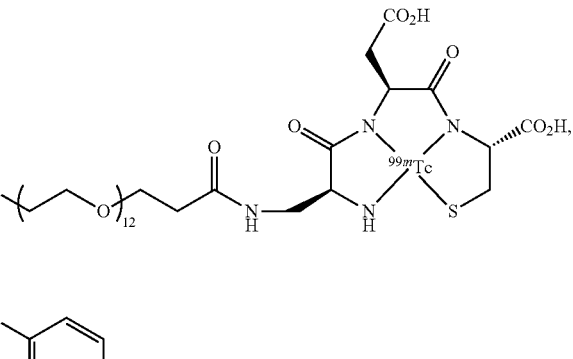
-continued
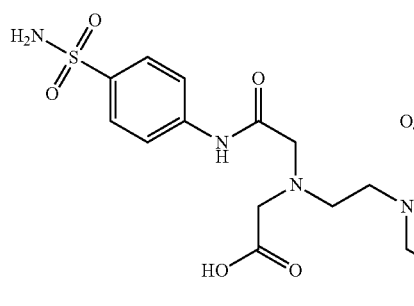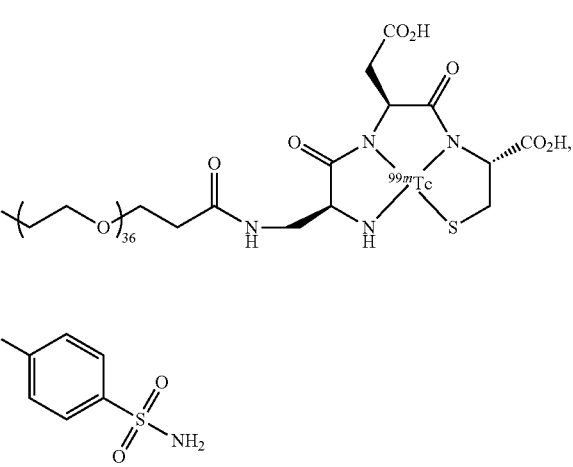
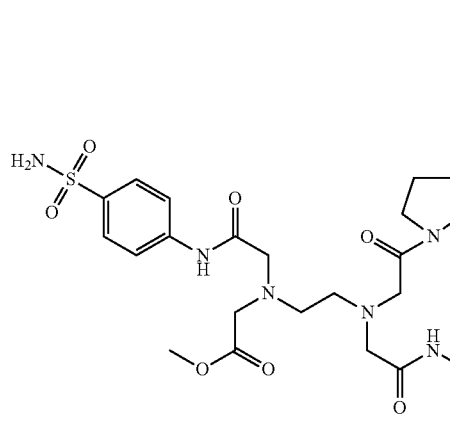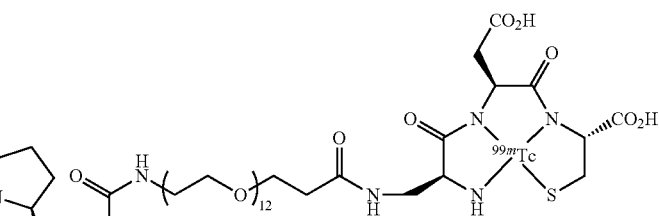
and -continued
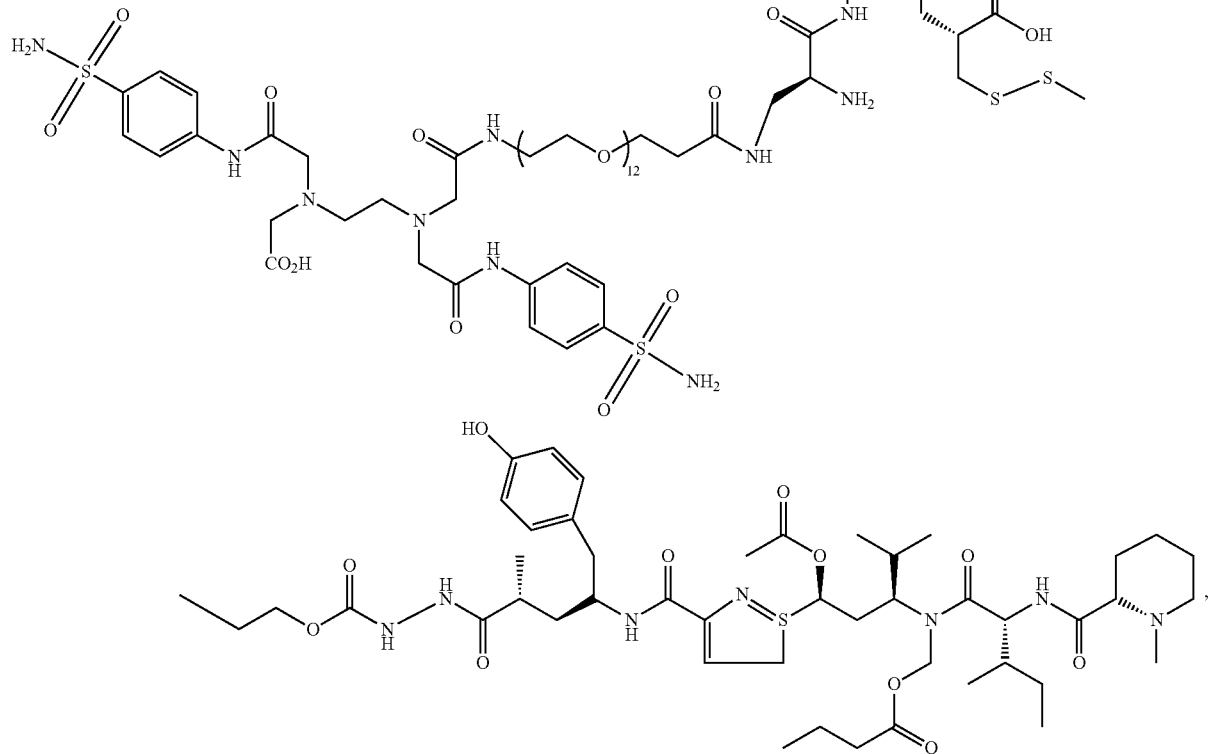
10. A composition comprising a conjugate according to claim 1, or a pharmaceutically acceptable salt thereof, and optionally at least one pharmaceutically acceptable excipient.
* * * * *